US007394923B2

(12) United States Patent
Zou et al.

(10) Patent No.: US 7,394,923 B2
(45) Date of Patent: Jul. 1, 2008

(54) IMAGING SYSTEM FOR GENERATING A SUBSTANTIALLY EXACT RECONSTRUCTION OF A REGION OF INTEREST

(75) Inventors: Yu Zou, Naperville, IL (US); Xiaochuan M. Pan, Chicago, IL (US)

(73) Assignee: The University of Chicago, Chicago, IL (US)

( * ) Notice: Subject to any disclaimer, the term of this patent is extended or adjusted under 35 U.S.C. 154(b) by 321 days.

(21) Appl. No.: 11/054,788

(22) Filed: Feb. 10, 2005

(65) Prior Publication Data

US 2005/0249432 A1 Nov. 10, 2005

Related U.S. Application Data

(60) Provisional application No. 60/630,624, filed on Nov. 24, 2004, provisional application No. 60/543,331, filed on Feb. 10, 2004.

(51) Int. Cl.
*G06K 9/46* (2006.01)
(52) U.S. Cl. .......................................... 382/131; 378/4
(58) Field of Classification Search ........................ None
See application file for complete search history.

(56) References Cited

U.S. PATENT DOCUMENTS 5,165,100 A 11/1992 Hsieh et al.
5,225,980 A 7/1993 Hsieh et al.
6,535,821 B2 3/2003 Wang et al.
2003/0058994 A1* 3/2003 Sembritzki .................. 378/108
2006/0140335 A1* 6/2006 Heuscher et al. ............... 378/4

OTHER PUBLICATIONS

Bushberg, "The Essential Physics of Medical Imaging", 1994, Williams & Wilkins p. 275, 276.*
Danielsson, P.E., et al., "Towards Exact 3D-reconstruction for Helical Cone-Beam scanning of Long Objects. A New Detector Arrangement and a New Completeness Condition," Proceedings of the 1997 International Meeting on Fully-Three-dimensional Image Reconstruction in Radiology and Nuclear Medicine, Jun. 25-28, 1997, Pittsburgh, PA, 4 pages.
Palamodov, V.P., "Reconstruction from ray integrals with sources on a curve," 2004 IOP Publishing Ltd., UK, pp. 239-242.
Zou, Y., et al., "Exact image reconstruction on PI-lines from minimum data in helical cone-beam CT," 2004 IOP Publishing Ltd., UK, pp. 941-959.

* cited by examiner

*Primary Examiner*—Vikkram Bali
*Assistant Examiner*—Thomas M Redding
(74) *Attorney, Agent, or Firm*—Brinks Hofer Gilson & Lione

(57) ABSTRACT

A method and apparatus for reconstruction of a region of interest for an object is provided. The reconstruction of the object may be based on chords which may fill a part, all, or more than all of the region of interest. Using chords for reconstruction may allow for reducing data acquired and/or processing for reconstructing a substantially exact image of the ROI. Moreover, various methodologies may be used in reconstructing the image, such as backprojection-filtration, and modified filtration backprojection.

50 Claims, 29 Drawing Sheets

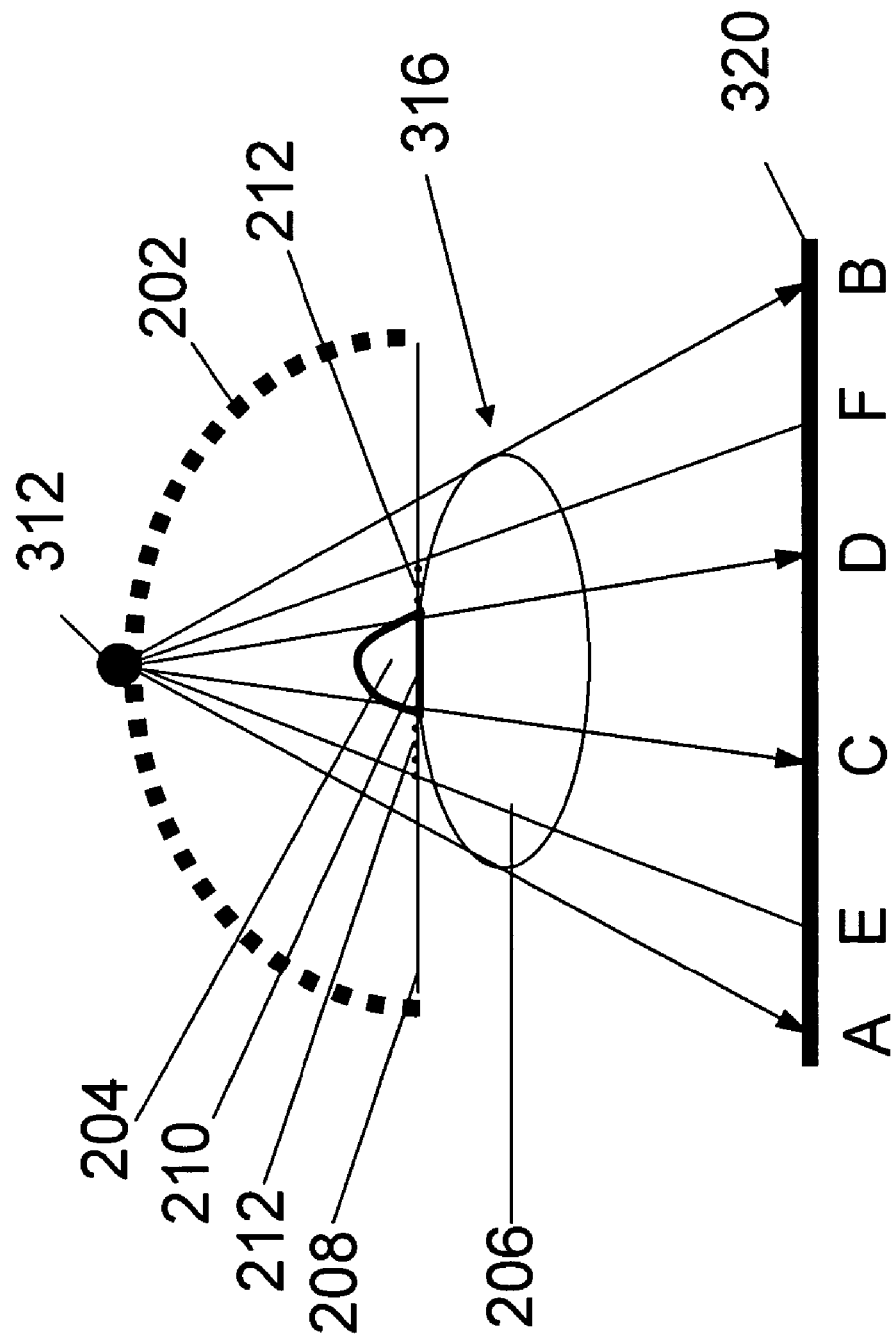

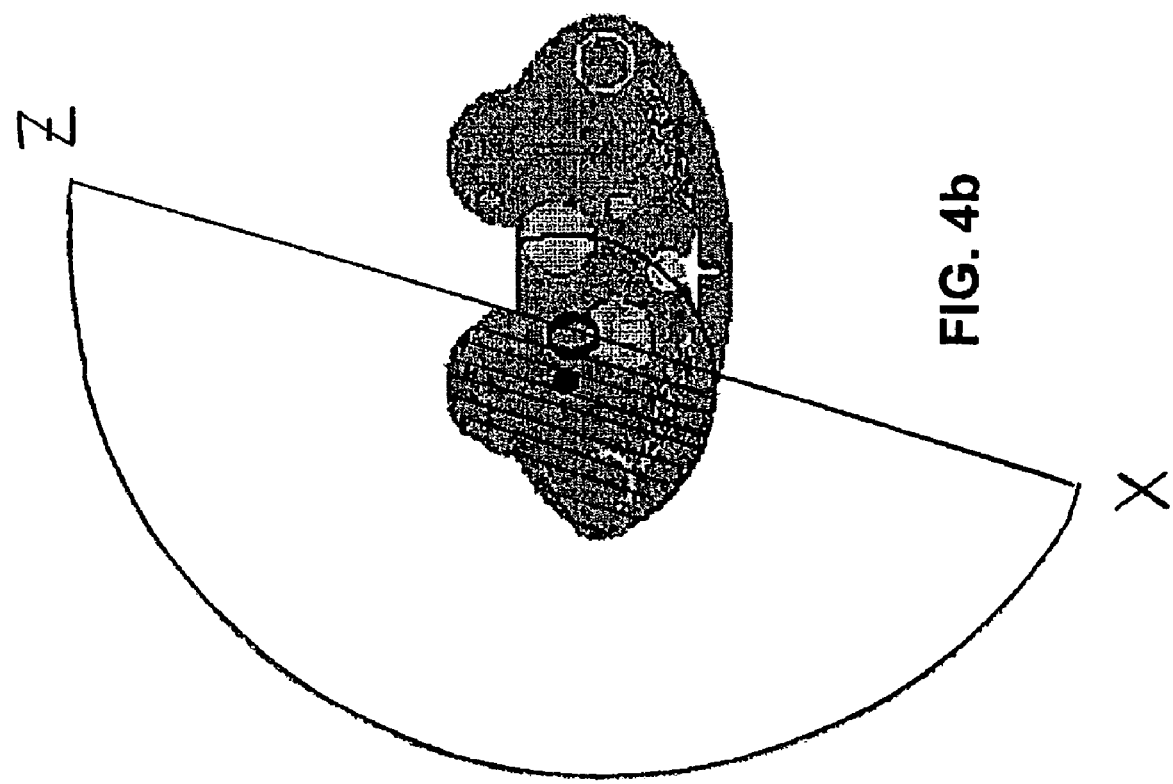

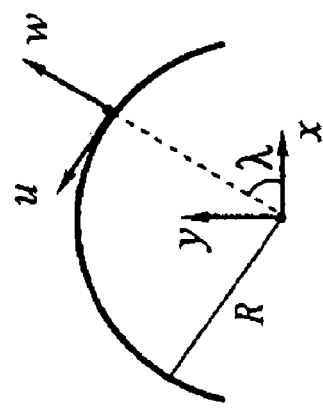
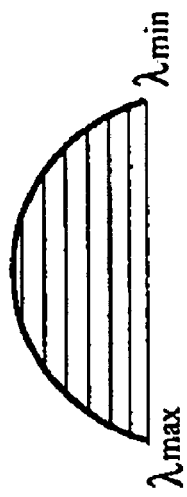
FIG. 7c
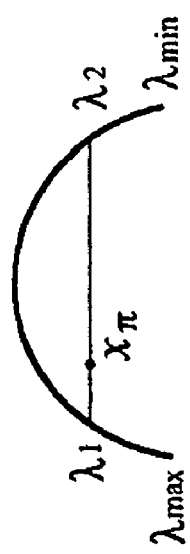
FIG. 7b
FIG. 7a

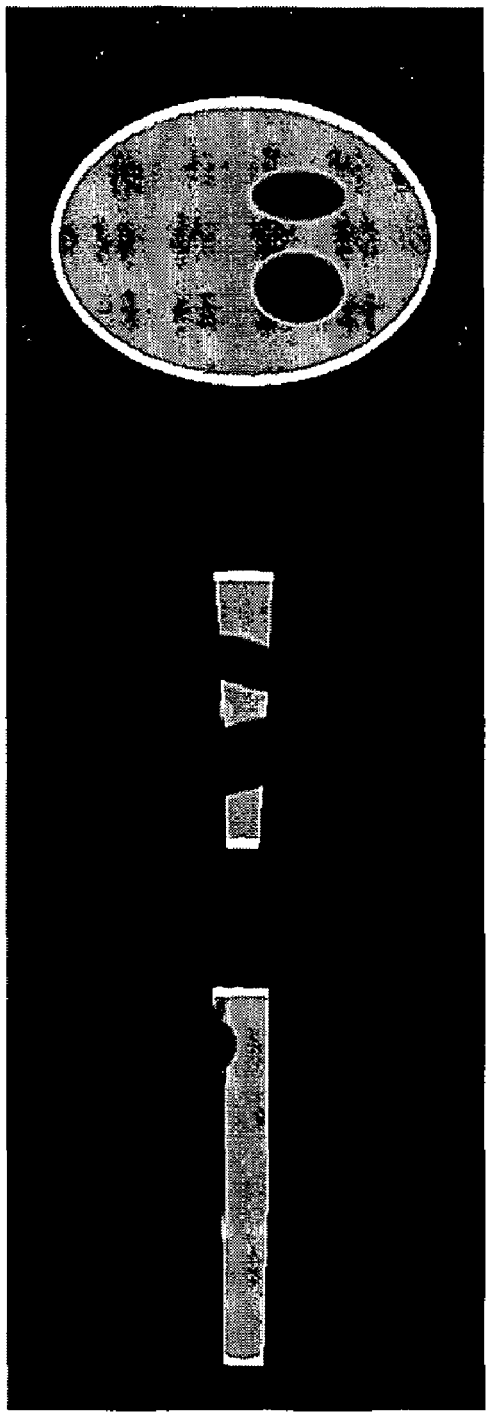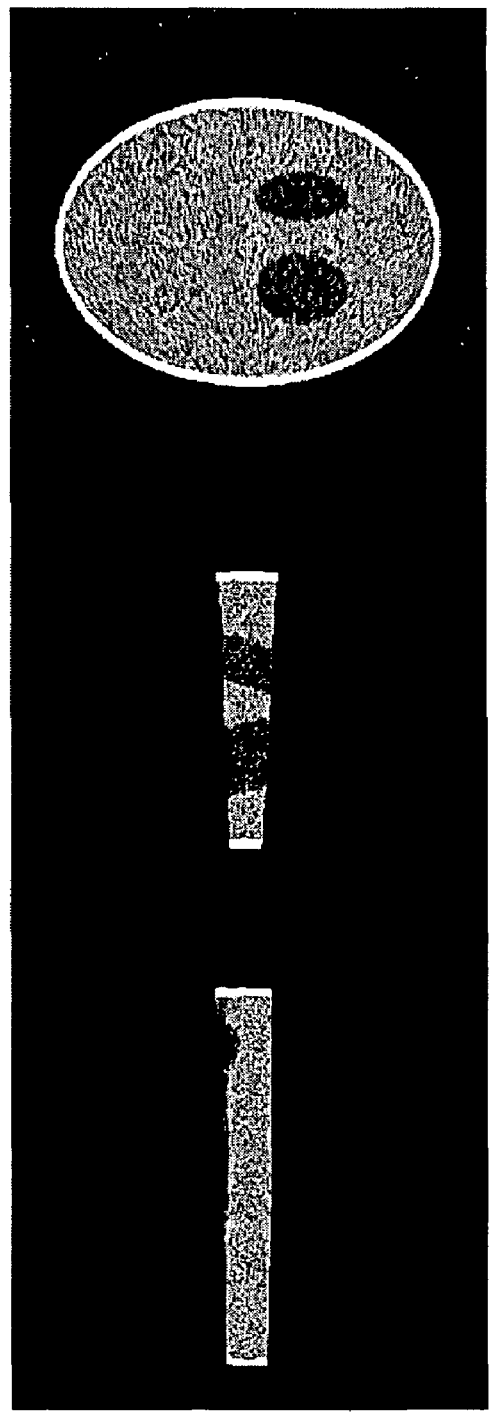

IMAGING SYSTEM FOR GENERATING A SUBSTANTIALLY EXACT RECONSTRUCTION OF A REGION OF INTEREST

REFERENCE TO RELATED APPLICATIONS

This application claims the benefit of U.S. Application Ser. No. 60/543,331 filed on Feb. 10, 2004, and claims the benefit of U.S. Application Ser. No. 60/630,624 filed on Nov. 24, 2004. U.S. Application Ser. No. 60/543,331 is incorporated by reference herein in its entirety. U.S. Application Ser. No. 60/630,624 is incorporated by reference herein in its entirety.

GOVERNMENT LICENSE RIGHTS

The U.S. Government has a paid-up license in this invention and the right in limited circumstances to require the patent owner to license others on reasonable terms as provided for by the terms of Grant Numbers EB000225, EB002765 awarded by the National Institutes of Health.

FIELD OF THE INVENTION

The present invention relates to a method and apparatus for imaging an object. More particularly, the present invention relates to a method and apparatus for imaging an interior of a part, or all, of a living or non-living object.

BACKGROUND

Imaging techniques typically comprise detecting a signal from an object and constructing an image based on the detected signal. The detected signal may include any detectable datum from the sample, such as an electromagnetic signal from any frequency range, a magnetic signal, an ionization signal, heat, particles (electron, proton, neutron, etc.), or the like.

The imaged object may comprise any portion of a living organism (e.g., human or animal) or a non-living object. For example, the portion may comprise an internal or an external portion, or may comprise the entire internal or external portion of the object. There are a wide variety of techniques for imaging of the object. Examples of imaging techniques include, but are not limited to: computed tomography (CT), positron emission tomography (PET), single-photon emission computed tomography (SPECT), magnetic resonance imaging (MRI), electron paramagnetic resonance imaging (EPRI), wave imaging (such as phase contrast imaging, thermacoustic imaging, and thermoptical imaging), and particle imaging. Further, various imaging techniques may be combined. For example, CT imaging and PET imaging may be combined to generate an image.

CT is an X-ray procedure in which the X-ray beam may move around the object, taking pictures from different angles. These images may be combined by a computer to produce a cross-sectional picture of the inside of the object. PET is a diagnostic imaging procedure that may assess the level of metabolic activity and perfusion in various organ systems of an object, such as a human body. A positron camera (tomograph) may be used to produce cross-sectional tomographic images, which may be obtained from positron emitting radioactive tracer substances (radiopharmaceuticals), such as 2-[F-18] Fluoro-D-Glucose (FDG), that may be administered intravenously to the object. SPECT scans and PET scans are part of the nuclear imaging family. The SPECT scan is capable of revealing information about the object, such as blood flow to tissue. For example, radionuclide may be given intravenously, with the tissues absorbing the radionuclides (diseased tissue absorbs at a different rate), and the rotating camera picking up images of these particles, which may then be transferred to a computer. The images may be translated onto film as cross sections and can be viewed in a 3-D format. Moreover, MRI and EPRI are imaging techniques that use a magnetic field and radiofrequency radiation to generate information, such as anatomical information.

To create an exact reconstruction of an image, prior systems have used a filtration-backprojection (FBP) methodology. This methodology requires that data be acquired for an entire section of an object and that all the acquired data be processed, even if an image of only a subsection of the object is sought. For example, if a CT image is sought of a single breast, the FBP methodology required scanning of the entire chest region, including not only the single breast, but the second breast, torso, etc. This is shown in FIG. 1a, which is a cross section of a portion of the scan with a source, an object and a detector. The FBP methodology required that data be acquired sufficient to image the entire section (such as the entire cross-section of the chest region). Thus, the beam of the source must be wide enough to expose the entire torso to X-rays, as shown in FIG. 1a. Further, as shown in FIG. 1a, the detector used in the prior systems must be large enough to obtain the data for the entire chest region. For a 3-dimensional image, the object must be scanned to acquire data for the entire section of the object, even though only image of a subsection is sought. This is shown in FIG. 1b, which includes a second cross-section of portion of the scan with a source, an object, and a detector at an angle different from that shown in FIG. 1a. Prior systems using the FBP methodology also required the data from the entire section (such as an entire chest region) be subject to data processing for reconstruction of the image. Specifically, the data from the entire chest region was subject to filtration. These requirements of the prior FBP methodology made data acquisition and data processing difficult.

SUMMARY

The invention comprises a method and apparatus for acquiring data for an imaging system. One aspect of the invention comprises a system and method for reconstructing an image based on chords. The chord-based reconstruction may be used in a variety of types of imaging including, without limitation, computed tomography (CT), positron emission tomography (PET), single-photon emission computed tomography (SPECT), magnetic resonance imaging (MRI), electron paramagnetic resonance imaging (EPRI), tomosynthesis, and wave imaging (such as phase contrast imaging, thermacoutic imaging, and thermoptical imaging). The chords used for reconstruction may fill at least a portion (such as all) of a region of interest (ROI). The ROI may be 2-dimensional, 3-dimensional, or n-dimensional. The chords used for reconstruction may be a connection between two points, such as a straight line or a section of a curve. The points which define the chords may be based on any aspect related to imaging, examples of which may include, without limitation, the trajectory of the source or the Cartesian coordinate system, as described in more detail below. By decomposing at least a portion of the ROI, such as the entire ROI, into chords, the image may be reconstructed based on the set of chords. For example, various methodologies, such as may use the chords to reconstruct a 2-dimensional or 3-dimensional ROI, such as backprojection-filtration (BPF), Minimum Filtration Backprojection (MFBP), and Filtration Backprojection (FBP).

One application of using the chord reconstruction methodology allows for reducing data acquired and/or processing for reconstructing a substantially exact image of the ROI. For example, an ROI which is less than an object support may be substantially exactly reconstructed by acquiring data which is less than required to substantially reconstruct the entire object support, and without requiring processing of data acquired from the entire object support. An object support may be defined as a domain in space within which the object function could be non-zero, and outside of which is certainly zero. Chords that may define at least a part (all, or more than all) of the ROI may also define less than the entire object support.

Using various parameters of data acquisition, such as the source trajectory or control of the source, data may be acquired which is less than the data required to image the entire object support. For example, a trajectory is determined of a source relative to an object (e.g., the source moving with the object stationary, the source stationary and the object moving, or the source and object both moving relative to one another). Some imaging systems generate data by moving a source relative to an object sought to be imaged, and by detecting the data using a detector. The data may thereafter be used to reconstruct an image of a part or all of the object. A suitable trajectory (or multiple suitable trajectories) of the source relative to the object may be selected based on the region of interest (ROI). A suitable trajectory (or multiple suitable trajectories) may include one wherein a set of segments of chords defined by the trajectory fills the ROI. If multiple trajectories are suitable, an optimal trajectory may be selected from the multiple trajectories depending on certain factors, such as reducing or minimizing exposure to a region or regions that are not of interest (non-ROI) from the source and reducing imaging effort.

As another example, at least one characteristic of the source is modified so that data may be acquired which is less than the data required to image the entire object support. The characteristic of the source may be modified during the source trajectory or may be constant during the source trajectory. Characteristics of the source that may be controlled or modified include any aspect of the source which may affect the signal received by the detector including, but not limited to: illumination coverage (e.g., aperture setting of beam, width of beam, modification of cone beam coverage, etc.); intensity of beam; and spectral distribution of beam. Modifying the characteristic of the source may depend on any criterion of data acquisition including, but not limited to: the ROI, and/or non-ROI. For example, the illumination coverage of the source may be modified as the source travels relative to the object so that the illumination coverage is substantially directed to the ROI and substantially not directed to non-ROI.

The invention also comprises a method and apparatus for processing data to reconstruct an image. One aspect of the invention comprises a system and method for reconstructing an image based on a non-fixed coordinate system. In one embodiment, the non-fixed coordinate system may be defined, at least in part, by the source trajectory or how the source travels relative to the object. After the image is reconstructed based on the non-fixed coordinate system, the image may be converted into a fixed coordinate system, such as a Cartesian coordinate system. In another embodiment, the image may be reconstructed using chords defined by the source trajectory. For example, two points along the source trajectory may define a chord. A portion or all of the ROI, either for a 2-Dimensional or 3-Dimensional ROI, may be defined by points along the chords defined by the source trajectory. A variety of methodologies, including filtered-backprojection (FBP), backprojection-filtration (BPF), and Minimum Filtration Backprojection (MFBP), may be used to reconstruct the image based on chords.

Another aspect of the invention comprises a method and apparatus for reconstructing an image based on backprojection filtration (BPF). The BPF methodology reconstructs an image within an ROI by first backprojecting the data (such as backprojecting weighted data) and then performing filtering (such as shift-invariant filtering) of the backprojection. A variety of data acquisition methodologies may be used to generate data for the BPF methodology. The BPF methodology may exactly reconstruct an image within a given ROI directly from reduced-scan data that contain truncations or from data that does not contain truncations.

Another aspect of the invention comprises a method and apparatus for substantially exactly reconstructing an image with truncated data. In one embodiment, the BPF methodology may substantially exactly reconstruct the image using truncated data. In another embodiment, the MFBP methodology may substantially exactly reconstruct the image using truncated data. The MFBP methodology differs fundamentally from existing FBP methodologies because, like the BPF methodology, the MFBP methodology admits reconstruction from truncated data. Specifically, the MFBP methodology may exactly reconstruct an image within a given ROI directly from reduced-scan data that contain truncations. The MFBP methodology may also exactly reconstruct an image from data that does not contain truncations.

Another aspect of the invention comprises a method and apparatus for reconstructing an image with redundant data. Data may be considered redundant if the source trajectory generates chords which are unnecessary to reconstruct the ROI (e.g., chords that do not fill the region of interest). Instead of simply discarding the redundant data, the redundant data may be used to modify, such as improve, a selected characteristic of the image. Any characteristic of the image may be modified using the redundant data including, but not limited to: noise, bias, texture, resolution, and variance.

Still another aspect of the invention comprises a method and apparatus for reconstructing an image for positron emission tomography. The data collected may be organized to perform a chord based reconstruction. Viewing the collected data as being generated by a virtual source traveling a virtual source trajectory, the collected data may be organized for the chord based reconstruction. A variety of virtual source trajectories may be used.

BRIEF DESCRIPTION OF THE DRAWINGS

FIGS. 2a-c show three cross-sections of a source, object, and detector when scanning a torso to acquire data for use in imaging wherein the data obtained is less than that required to reconstruct a substantially exact image of the entire object support.

FIG. 4b shows a cross-section of a chest including breasts with a trajectory from "X" to "Z."

FIG. 7a shows a chord-segment joining two points, labeled $\lambda_1$ and $\lambda_2$ on the source trajectory with a starting angle of $\lambda_{min}$ and an ending angle of $\lambda_{max}$.

FIG. 7b shows the region $\Omega_R$ enclosed by the source trajectory and the PI-line segment specified by $\lambda_{min}$ and $\lambda_{max}$ shown in FIG. 6a.

FIG. 7c shows a fixed-coordinate system (x, y) with its origin on the center of rotation of the source, the rotation-coordinate system {u, w} with its origin on the source point, and a radius R of the source trajectory.

FIG. 17b illustrates a reconstruction image of the Shepp-Logan phantom on chords comprising the surface shown in FIG. 17a.

FIG. 17c shows a profile of the reconstructed (solid line) and true (dashed line) images along the chord indicated in FIG. 17a.

FIGS. 19a-b illustrate images of the Shepp-Logan phantom reconstructed using the minimum filtration backprojection methodology from the generated (in FIG. 19a) and noisy (in FIG. 19b) 3-PI data using chords, respectively.

DETAILED DESCRIPTION OF THE PRESENTLY PREFERRED EMBODIMENTS

Figure 1A:
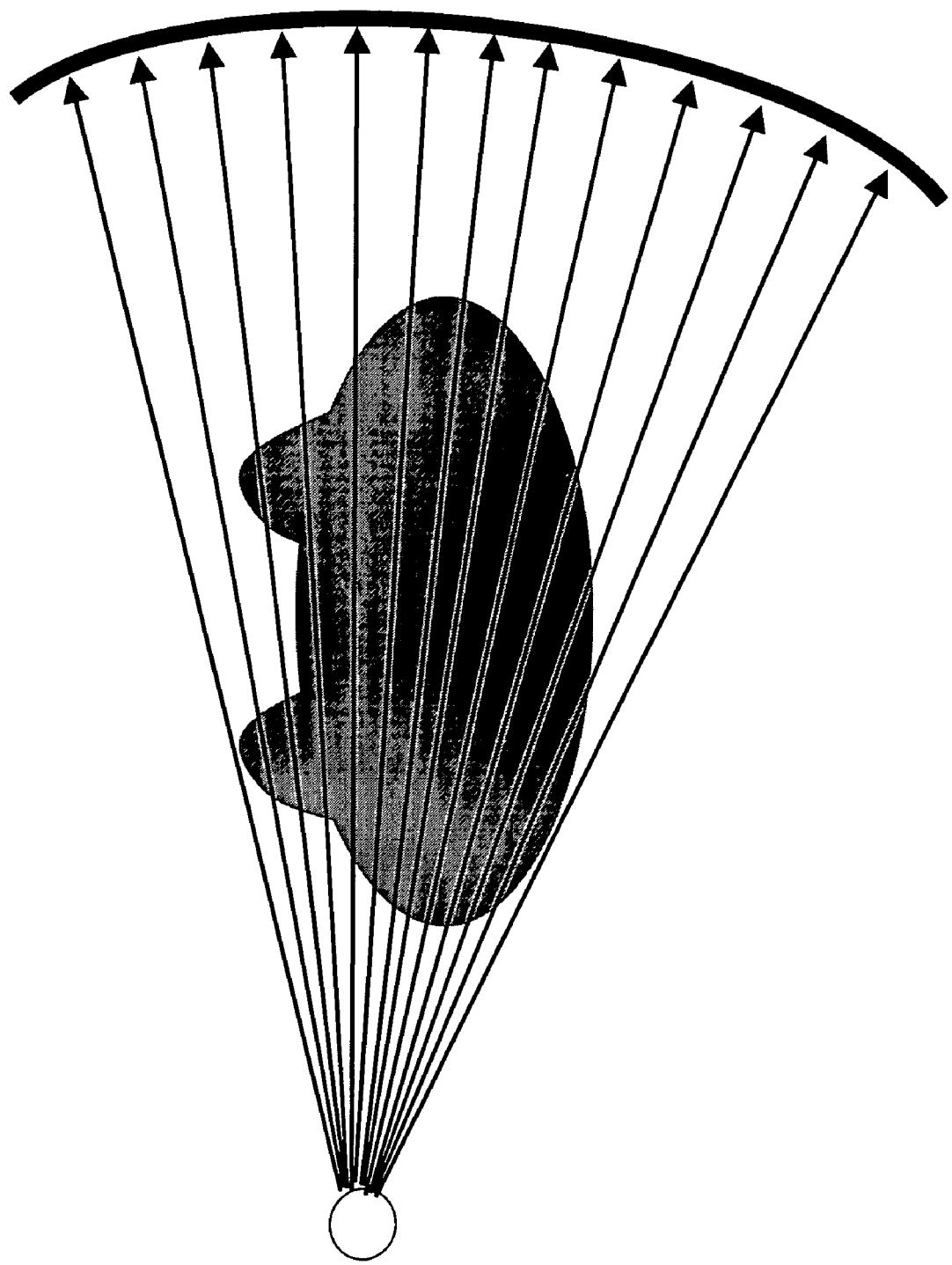
FIGS. 1a and 1b show two cross-sections of a source, object, and detector when scanning a torso to acquire data for use in imaging using an FBP methodology.
Figure 1B:
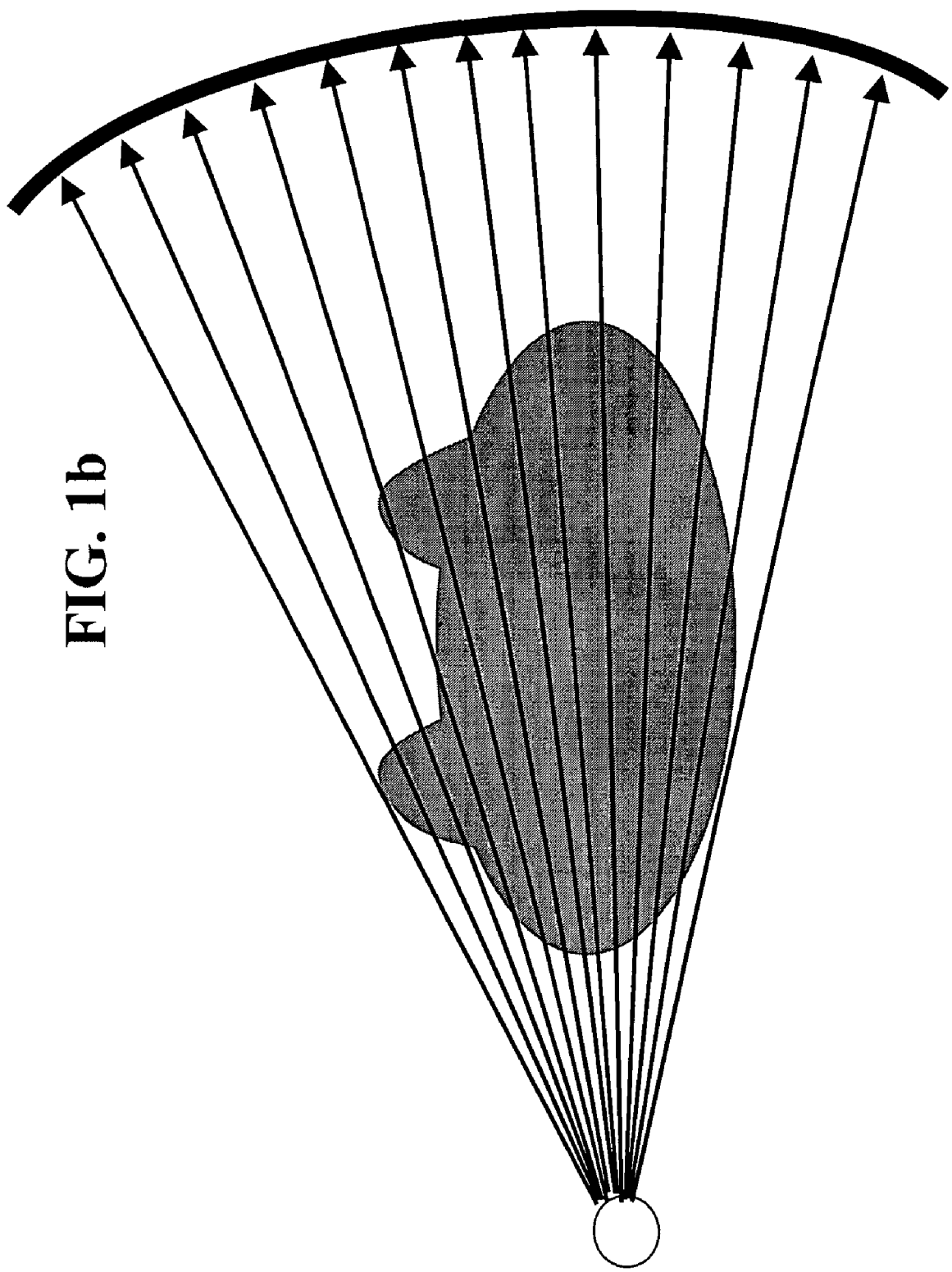

In order to address the deficiencies of the prior art, a method and apparatus is described below for imaging of an object. The imaging of an object may be based on chords that fill at least a portion of the object support such as all, or more than all of a region of interest (ROI). The ROI may be 2-dimensional, 3-dimensional, or n-dimensional. The chords used for reconstruction may be a connection between two points, such as a straight line or a section of a curve. The points which define the chords may be based on any aspect related to imaging, examples of which may include, without limitation, the trajectory of the source or the Cartesian coordinate system, as described in more detail below. By decomposing the ROI, into chords, the image may be reconstructed based on the set of chords. For example, various methodologies, such as may use the chords to reconstruct a 2-dimensional or 3-dimensional ROI, include backprojection-filtration (BPF), Minimum Filtration Backprojection (MFBP), and Filtration Backprojection (FBP). For example, the various points along the chords which fill at least a portion (or all) of the ROI may be exactly reconstructed to image the ROI.

One application of using the chord reconstruction methodology allows for reducing the amount of data acquired and/or processed in order to reconstruct a substantially exact image of the ROI. For example, an ROI which is less than an object support may be substantially exactly reconstructed by acquiring data which is less than required to substantially reconstruct the entire object support, and without requiring processing of data acquired from the entire object support. An object support may be defined as a domain in space within which the object function could be non-zero, and outside of which is certainly zero. As discussed in more detail below, an example of a 2-dimensional object support comprises a cross section of a chest, with the region inside the cross-section of the chest comprising the object support (which may have non-zero data values) and the section outside of the cross-section being outside of the object support (which certainly has a zero value). If the ROI comprises a portion of the object support, such as a cross-section of one of the breasts in the section of the torso, data may be acquired and processed which is less than that for the entire object support in order to substantially exactly reconstruct the cross-section of the breast. For example, data associated with support segments which define the ROI may be used to exactly reconstruct the cross-section of the breast. Support segments may be defined as chords with values on the segments that may be non-zero, and values for the object function outside the segments that are certainly zero. Therefore, unlike previous methodologies, data related to the support segments, rather than data for the entire object support, need only be acquired in order to substantially exactly reconstruct the ROI. Similarly, an example of a 3-dimensional object support comprises a section of the torso, such as a volume from the stomach to the neck. If the ROI comprises a sub-volume of the object support, such as a volume of one of the breasts in the section of the torso, data may be acquired and processed which is less than that for the entire object support in order to substantially exactly reconstruct the volume of the breast. In the 3-dimensional example, data may be acquired which is less than the entire torso in order to image the volume of a single breast. For example, data associated with support segments that define the volume of the breast may be obtained in order to image the single breast.

Chords may be used to define at least a part (all, or more than all) of the ROI. Further, the chords may be used to define less than the entire object support. Using various parameters of data acquisition, such as the source trajectory or control of the source or detector, data may be acquired which is less than the data required to image the entire object support. For example, when seeking to create a substantially exact reconstruction of a 2-dimensional cross-section, the method and apparatus in one aspect of the invention does not require data acquisition for the entire contiguous cross-section when only an image of a portion of the cross-section is sought. Similarly, when seeking to create a substantially exact reconstruction of a 3-dimensional volume, the method and apparatus in one aspect of the invention does not require data acquisition for an entire volume when only a portion of the object support is sought to be imaged.

In the drawings where like reference numerals refer to like elements, FIG. 2a shows one illustration of a cross section of a source 312, object 316, and detector 320. As discussed in more detail below, the source may travel relative to the object via a trajectory, designated by the dashed line in FIG. 2a. A portion 204 of the entire cross-section 206 is sought to be substantially exactly reconstructed (as shown in a bold outline). In prior imaging systems, it was required to obtain a sufficient amount of data to image the entire cross-section 206. Thus, the source trajectory had to be sufficient to obtain data for the entire cross-section, such as a trajectory which encircled cross-section 206. At the various points in the trajectory, the source 312 was required to have a beam wide enough to cover the entire cross-section 206. Further, the detector 320 had to be large enough so that data from point "A" to point "B" was registered. Moreover, the data from point "A" to point "B" had to be processed, at least in part, if only portion 204 was sought to be exactly reconstructed.

By contrast, in one aspect of the invention, if portion 204 is sought to be substantially reconstructed, data less than that sufficient to image the entire cross-section 206 (which includes portion 204 and an additional section) may be obtained. As discussed in more detail below, various methodologies, such as backprojection-filtration (BPF), and Minimum Filtration Backprojection (MFBP), do not require data sufficient to image the entire cross-section 206 if portion 204 is sought to be imaged. Rather, data less than that sufficient to image the entire cross-section 206 may be used. For example, data sufficient to image only portion 204 may be used, such as data for support segments which define portion 204.

Because data less than that sufficient to image the entire cross-section is required, various aspect of the data acquisition, such as selection of the trajectory, control of the source or detector, etc. may be modified and may be different from that used in previous imaging systems. For example, the relative trajectory of the source may be selected which acquires data that is less than that sufficient to image the entire cross-section. As shown in FIG. 2a, the trajectory is semi-circular in order to generate a set of chords to fill the portion 204 (as discussed in more detail below). These set of chords may be defined as support segments since beyond the support segments, the object function is zero. This is in contrast to a prior art trajectory which would completely encircle cross-section 206. The trajectory shown in FIG. 2a is merely an example. Other trajectories may be used, as discussed in more detail below. For example, trajectories which are greater than the semi-circular trajectory shown in FIG. 2a but are less than a 360° trajectory may be used. In this manner, data which is less than that sufficient to image the entire cross-section may be obtained. Similarly, if a 3-dimensional image is sought, data which is less than that sufficient to image the entire 3-dimensional volume may be obtained if the sought image is less than the entire 3-dimensional volume.

As another example, the source may be modified so that data acquired by the detector is less than that sufficient to image the entire cross-section. For example, the characteristics of the source may be modified such that data may be acquired at least sufficient to image the ROI, but less than that sufficient to image the entire cross-section. Any characteristic of the source may be modified to affect the data which is detected by the detector. Example characteristics, discussed in more detail below, include illumination coverage (e.g., aperture setting of beam, width of beam, modification of cone beam coverage, etc.); intensity of beam; and spectral distribution of beam. For example, the width of the beam of the source may be modified so that the beam covers the entire portion 204. The detector 320 thus may acquire data between points "C" and "D". Alternatively, the beam width of the source may be in a range that is less than the entire cross-section (e.g., less than from points "A" and "B") to a range that includes portion 204 (e.g., greater than or equal to points "C" and "D.") For example, the beam width may be such that data is acquired at the detector 320 between points "E" and "F."

Figure 2B:
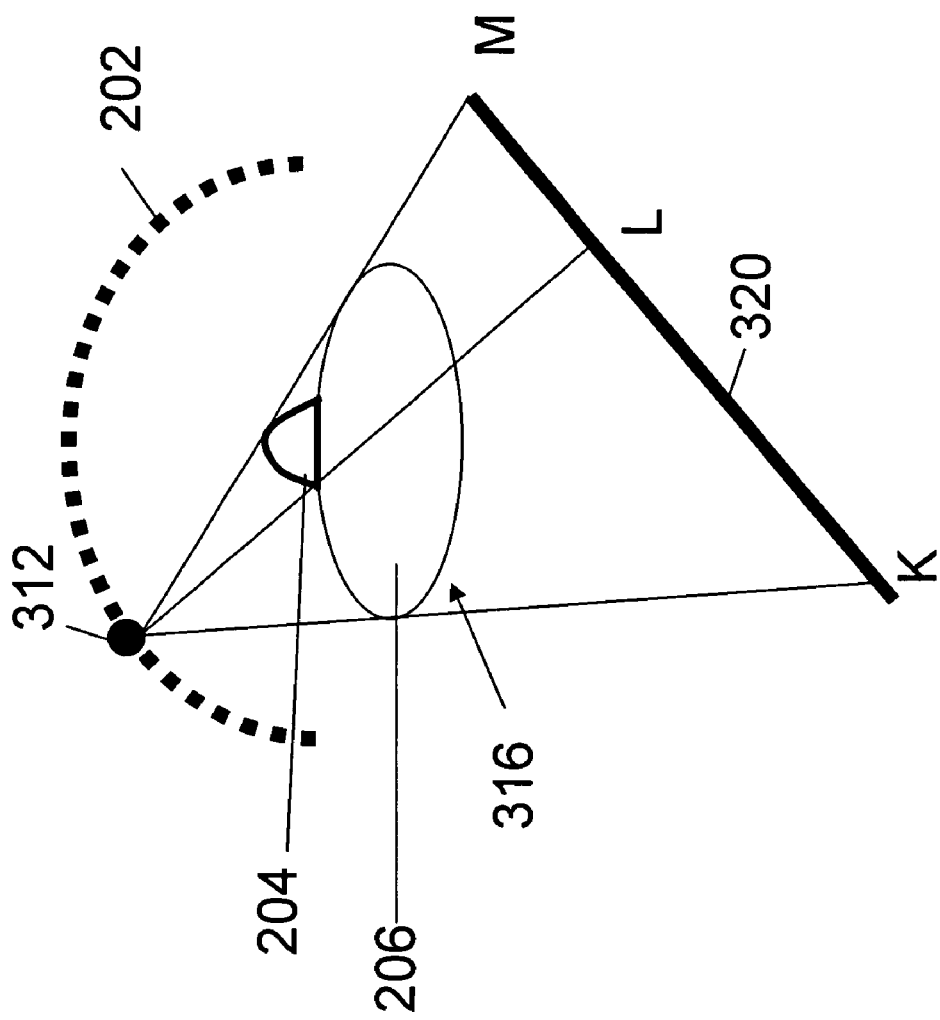

As the source travels relative to the object, the characteristics of the source may remain constant or may change. For example, the characteristics of the source may remain constant such that data may be acquired at least sufficient to image the ROI, but less than that sufficient to image the entire cross-section. Or, the characteristics of the source may change at least once during the trajectory such that data may be acquired at least sufficient to image the ROI, but less than that sufficient to image the entire cross-section. FIG. 2b shows a cross section of a source 312, object 316, and detector 320, where source 312 is at a different position than that shown in FIG. 2a. As discussed in more detail below, the characteristics of the source selected may depend on the ROI selected. As shown in FIG. 2b, the beam width may change such that it may be widened or narrowed such that at least the ROI is included in the beam. Or, the beam width may be selected so that it includes the ROI but is not wide enough to cover the entire cross-section 206. Controlling any aspect of the source may reduce illumination of the object, while still allowing for sufficient illumination of portion 204 for imaging. For example, controlling the source may still allow for data acquisition of support segments which may include portion 204.

Figure 2C:
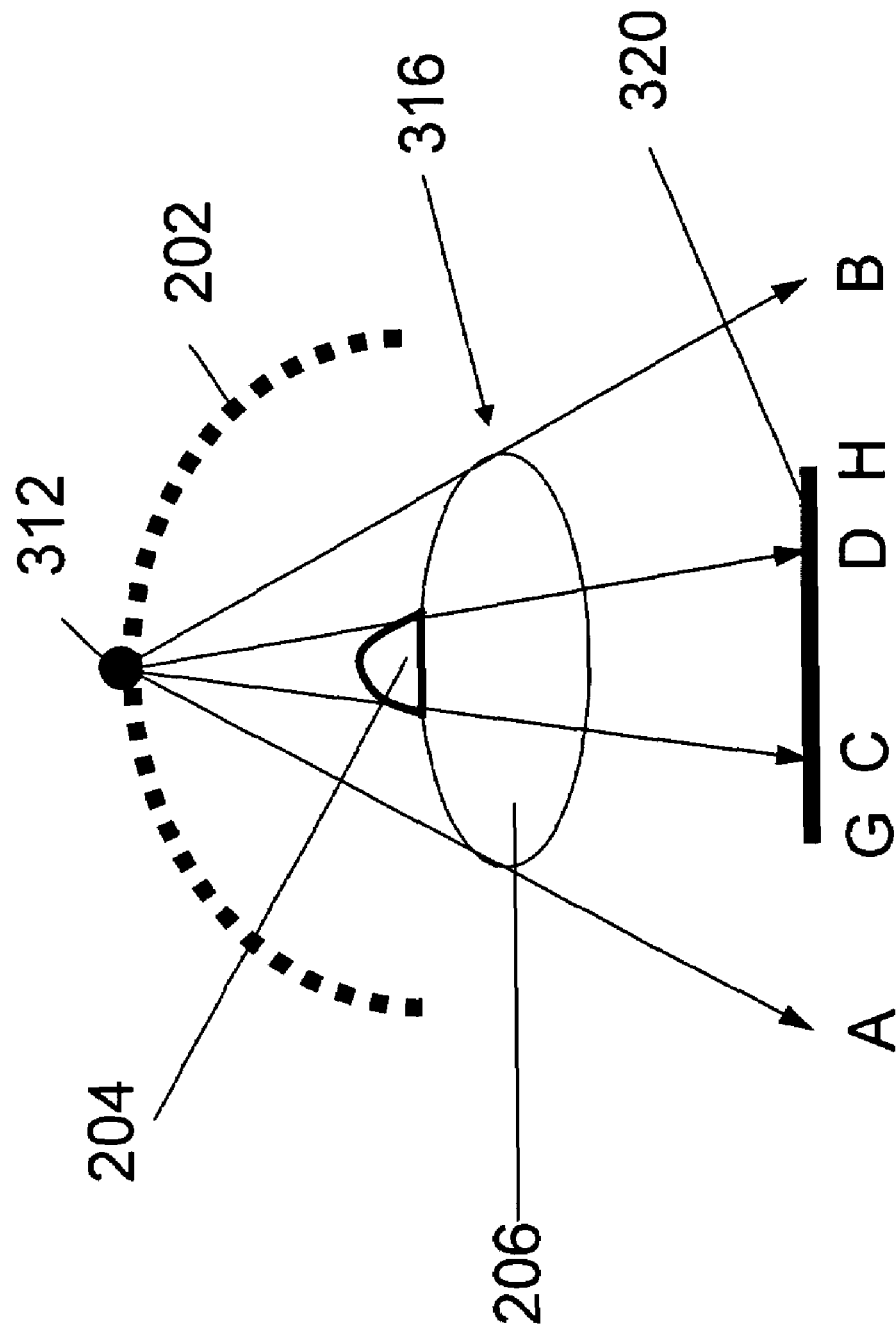

Because the methodologies do not require data sufficient to image the entire cross-section or an entire volume, truncated data (e.g., data which is less than that sufficient to image the entire cross-section or which may image a truncated portion) may be obtained. For example, as shown in FIG. 2c, the detector is shown as spanning from point "G" to point "H," which includes data regarding the ROI, between points "C" and "D." Under the prior art methodologies, the detector 320 had to be larger to be able to obtain data sufficient to image the entire cross-section. By contrast, the detector 320 shown in FIG. 2c may be smaller, and may be such that a truncated portion of the cross-section is imaged. Further, reduced data (e.g., data which is less than that sufficient to image the entire cross-section) may be obtained. A smaller detector may be advantageous as it may be less expensive to manufacture, and/or, if it is designed to move during data acquisition, may require less energy to move.

As discussed above, prior methodologies acquired additional data which was not required to substantially exactly reconstruct an ROI. This additional data may not improve the reconstruction of the ROI, and may reduce the quality of the reconstruction. For example, if there is motion or noise in the data related to the object support which is outside of the ROI, this data may degrade the image if used to reconstruct the ROI.

Another aspect of the invention is a method and apparatus for processing data to generate an image, such as a substantially exact image. In one embodiment, the image is reconstructed based at least in part on chords. A part, all, or more than all of the ROI may be decomposed into chords. The chords may be defined by two points, with a connection between the two points, such as a straight line or a curve. For example, an entire 2-dimensional or 3-dimensional ROI may be defined by a set of chords. The ROI may be reconstructed based on the chords, such as by a point by point reconstruction along segments of the chords.

The chords used for reconstruction may be defined by any aspect related to imaging. For example, the two endpoints which may define a chord may be based on the source trajectory, as discussed in more detail below. As another example, chords may be defined by the Cartesian coordinate system. Various methodologies may be used to reconstruct the imager based on chords defined by the source trajectory including FBP, BPF, and MFBP. In another embodiment, the image may be reconstructed based on data which is less than that sufficient to image an entire portion (e.g., in imaging a portion of a cross-section, data which is less than that sufficient to image the entire cross-section may be used). Various methodologies may be used to reconstruct an image using data which is less than that sufficient to image an entire portion including, without limitation, BPF and MFBP.

Figure 3:
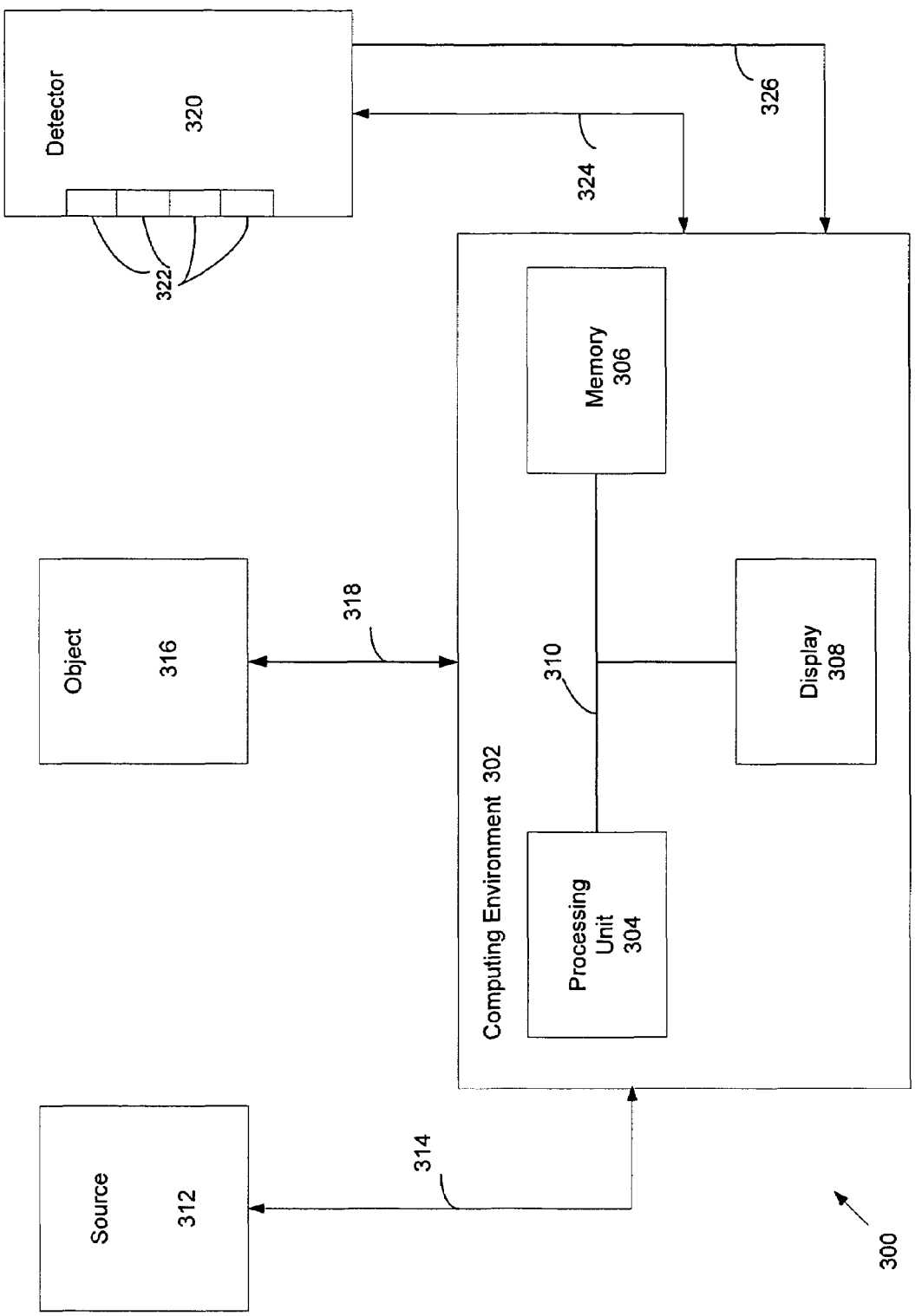
FIG. 3 shows a block diagram of an exemplary imaging system.

FIG. 3 shows a block diagram of an imaging system 300 according to an embodiment of the present invention. The system may include any type of imaging system. Examples of types of imaging systems include, but are not limited to: computed tomography (CT), positron emission tomography (PET), single-photon emission computed tomography (SPECT), magnetic resonance imaging (MRI), electron paramagnetic resonance imaging (EPRI), tomosynthesis (such as if a trajectory is used which creates chords which pass through the portion to be imaged, as discussed below), and wave imaging (such as phase contrast imaging, thermacoutic imaging, and thermoptical imaging). Moreover, the imaging systems may include a single type of imaging, or multiple types of imaging. For example, the imaging system may comprise CT imaging. Alternatively, the imaging system may comprise multiple modality imaging, such as CT and PET imaging in combination. Further, the imaging system may be used in combination with another system. For example, the imaging system may be integrated with a therapeutic system, such as a radiation therapy delivery system. The two systems may work in combination with the imaging system providing imaging for guidance (such as CT imaging) and radiation therapy for treatment.

With reference to FIG. 3, an exemplary imaging system 300 for implementing the invention includes a general purpose computing device in the form of a computing environment 302, including a processing unit 304, a system memory 306, and display 308. A system bus, 310, may couple various system components of the computing environment 302, including the processing unit, 304, the system memory 306, and the display 308. The processing unit 304 may perform arithmetic, logic and/or control operations by accessing system memory 306. For example, the processing unit 304 may control the various system components to acquire data for imaging and may process the acquired data to generate an image. Alternatively, different system processors, or different devices may control the various system components to acquire data for imaging and may process the acquired data to generate an image.

The system memory 306 may store information and/or instructions for use in combination with processing unit 304. For example, the system memory 306 may store computer readable instructions, data structures, program modules or the like for operation of the imaging system 300, including, for example, control of movement of any of the source, object, and detector and control of the functionality of the source and the detector, as discussed below. Further, the system memory 306 may store data obtained from detector 320 and may process the data for display on the display 308, as discussed in more detail below. The system memory 306 may include volatile and non-volatile memory, such as random access memory (RAM) and read only memory (ROM). It should be appreciated by those skilled in the art that other types of computer readable media which can store data that is accessible by a computer, such as magnetic cassettes, flash memory cards, random access memories, read only memories, and the like, may also be used in the exemplary computer environment. A user may enter commands and/or information, as discussed below, into the computing environment 302 through input devices such as a mouse and keyboard, not shown. The commands and/or information may be used to control operation of the imaging system, including acquisition of data and processing of data.

FIG. 3 further shows source 312 communicating with computing environment 302 via line 314. Line 314 may comprise a control line whereby the processing unit may control at least one characteristic of source 312. Characteristics of the source which may be controlled comprise any aspect of the source including, but not limited to: illumination coverage (e.g., aperture setting of beam, width of beam, modification of cone beam coverage, etc.); intensity of beam; and spectral distribution of beam. Source 312 may be stationary or may move relative to any one, or both, of object 316 and detector 320. Line 314 may also control movement of source 312, such as by sending commands to a motor (not shown) to move all or a part of source 312. For example, if the source 312 is an X-ray tube, the motor may move the entire X-ray tube relative to one, or both of, object 316 and detector 320. Alternatively, the X-ray tube may remain stationary with a reflector revolving using the motor. In this manner, the beam emanating from the X-ray tube may be moved by bouncing the beam off the revolving reflector.

The source 312 may comprise any device which generates any signal that may be received from detector 320. The source 312 selected for imaging system 300 may depend on the type of imaging performed by imaging system 300. For example, source 312 may generate electromagnetic radiation in any frequency range, such as gamma rays, x-rays, visible light, microwaves, and radio/tv waves. Specifically, source 312 may comprise an X-ray source and generate X-rays or may comprise a radio frequency (RF) source and generate radio waves. Source 312 may also generate other types of signals such as magnetic fields, mechanical waves (e.g., sound waves), heat, particle (e.g., electron, proton, neutron), or the like. Though depicted in imaging system 300, certain types of imaging systems do not require a source (such as source 312). For example, PET scanning does not require an external source, as discussed in more detail below.

FIG. 3 also shows object 316. Object 316 may comprise anything which is capable of being scanned, such as a living organism (e.g., human or animal) or a non-living object (e.g., a piece of luggage, a cargo container, food, an ocean, underground the earth, etc.). The position of the object may be stationary or may move relative to any one, or both, of source 312 and detector 320. Line 318 may control movement of object 316, such as by sending commands to a motor (not shown) to move object 316. Any part, or all, of object 316 may be imaged using imaging system 300. Further, the object may ingest or be injected with a substance, such as a contrast agent, which may assist in imaging a part or all of object 316. As shown in FIG. 3, source 312 is external to object 316. Alternatively, source 312 may be internal to object 316.

FIG. 3 further shows detector 320 communicating with computing environment 302 via lines 324 and 326. Line 324 may comprise a control line whereby the processing unit may control at least one characteristic of detector 320. Characteristics of the detector which may be controlled include any aspect of the detector including, but not limited to activation/deactivation of sections 322 of the detector or sensitivity of the detector. Line 326 may comprise a data line whereby data sensed from the detectors may be sent to computing environment 302 for processing by processing unit 304, as discussed below. Detector 320 may comprise any type of detector which senses any datum, such as electromagnetic radiation from any frequency range (such as X-rays), magnetic fields, sound waves, heat, or the like. For example, for a 2-dimensional detector (flat-panel imager), detector 320 may comprise one row of detectors for fan beam geometry, four rows of detectors for quasi-fan-beam geometry, or more than four rows of detectors for cone-beam geometry. Detector 320 may be stationary or may move relative to any one, or both, of source 312 and object 316. Line 324 may control movement of detector 320, such as by sending commands to a motor (not shown) to move all or a part of detector 320. As shown in FIG. 3, detector 320 is external to object 316. Alternatively, detector 320 may be internal to object 316. Thus, both source 312 and detector 320 may be internal or external to the object. Moreover, source 312 may be internal and detector 320 may be external to object 316, or source 312 may be external and detector 320 may be internal to object 316. For example a dental image of a patient may be acquired with an external source and a detector held in the mouth of a patient.

Various scans of the object may be generated based on the movement of one, some or all of source 312, object 316, and detector 320. For example, a line scan may be generated by subjecting object 316 to translational movement while keeping source 312 and detector 320 stationary. As another example, a circular scan may be generated by rotating source 312 and detector 320 in synch while keeping object 316 stationary. In still another example, a helical scan may be generated by rotating source 312 and detector 320 in synch while subjecting object 316 to translational movement. Line, circular and helical scans are merely exemplary. Other scans may be generated, as discussed in more detail below.

The object 316 may include a region of interest (ROI) for imaging by imaging system 300. The ROI may include a 2-dimensional cross-section or may be 3-dimensional volume of the object. For example, a 2-dimensional image may comprise a projection or a transverse image. As another example, a 3-dimensional image may comprise a sagittal or a coronal image. Further, the ROI may be a single portion, multiple portions, or all of object 316. For example, the ROI may be an entire volume of a single breast (either right or left breast) or may be an entire volume of both the right and left breast. Alternatively, the ROI may be a cross-section of a single breast.

Selecting a Trajectory for Imaging

As discussed above, typical imaging systems required that data be acquired for an entire object support and that all the acquired data be processed, even if an image of only a subsection of the object support is sought. In one aspect of the invention, if an image of a subpart of an object support is sought (such as an ROI which is a part of a cross section or a volume), the relative trajectory of the source may be selected which acquires data that is less than that sufficient to image the entire object support (such as the entire cross-section or entire volume), but which acquires data that is at least sufficient to image the ROI. For example, using a typical imaging system, if the ROI were a single breast, a trajectory would be selected which would completely encircle the entire chest region. For example, if a helical scan were used, the source would rotate an entire 360° around the chest region in order to obtain data regarding a single breast. This results in a significant amount of over-scanning of the object and in unnecessary over-exposure of the object to source 312. This over-exposure may be problematic if one seeks to limit the amount of exposure to source 312, such as may be the case with an X-ray source. Over-scanning may also be undesirable if the speed of acquisition is a priority.

In one aspect of the invention, a suitable trajectory (or multiple suitable trajectories) of the source relative to the object may be selected based on the ROI. A suitable trajectory (or multiple suitable trajectories) may include one wherein a set of support segments of chords defined by the trajectory fills the ROI. If multiple trajectories are suitable, an optimal trajectory may be selected from the multiple trajectories depending on certain factors, as discussed below.

Figure 4A:
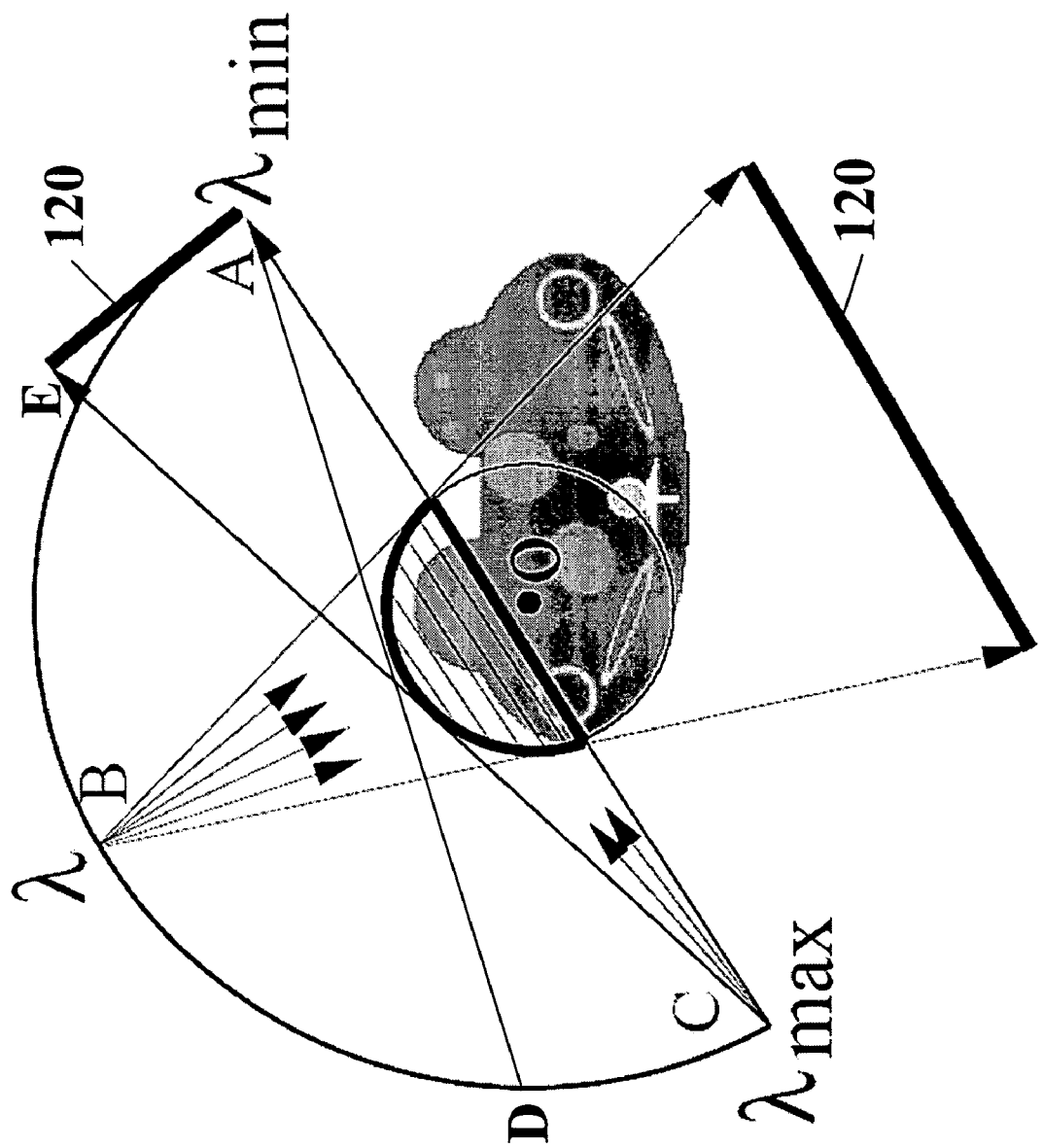
FIG. 4a shows a cross-section of a chest including breasts with a trajectory from "A" to "C."

The ROI may be 2-dimensional or 3-dimensional. One example of a 2-dimensional ROI (a cross-section of a single breast) and a suitable trajectory from point "A" to point "C" is shown in FIG. 4a. FIG. 4a shows a diagram of a chest cross-section including breasts. The region enclosed by the thick curve indicates the peripheral ROI for imaging. The parallel line segments in the ROI depict the support-segments, which are the portions of the parallel PI-line segments within the ROI. As shown in FIG. 4a, the values of the object function along the supports segments may be non-zero, whereas the values outside the supports segments are certainly zero. Points on the "A" to "C" trajectory may define chords. Specifically, a chord may be defined as a straight line connecting two points along the trajectory. In the example shown in FIG. 4a, one chord is defined by points "A" and "C" on the trajectory. As shown on this "A-C" chord, at least a part of the chord (in bold in FIG. 4a) is a segment of the chord that passes through the object to be scanned. A specific trajectory is suitable for imaging if segments of chords defined by the trajectory fill the ROI.

Multiple sets of chords may define a single ROI. In the 2-dimensional example shown in FIG. 4a, the "A" to "C" trajectory is suitable since there is a set of support segments, defined by chords from the trajectory, which fill the area of the region of interest. For example, a set of chords, each parallel to the "A" to "C" chord may fill the area of interest, as shown in FIG. 4a. Another example is a set of chords with the first point of each chord being defined by point "A" on the trajectory and the second point of each chord being defined in a range from point "C" to point "D." Another example of a set of chords that fills the area of interest is with the first point of each chord being defined by point "C" on the trajectory and the second point of each chord being defined in a range from point "A" to point "E." Thus, multiple sets of chords may fill an area of interest, depending on the points selected along the trajectory.

Further, more than one trajectory may be suitable for an ROI. Another example of an ROI of the single breast, with a suitable trajectory from point "X" to point "Z," is shown in FIG. 4b. Similar to the trajectory shown in FIG. 4a, the "X" to "Z" trajectory may define a set of segments of chords that fills the ROI of the single breast.

One may select a preferred trajectory from the multiple suitable trajectories based on a single criterion or multiple criteria. Examples of criteria include, but are not limited to: (1) reducing or minimizing exposure to non-ROI portions from the source; and (2) reducing imaging effort. First, there are instances where exposure from the source should be reduced or minimized. For example, in CT scanning which uses an X-ray source, the trajectory may be selected so that the exposure of the source's X-rays to the regions outside of the region of interest (non-ROI) is reduced or minimized. FIGS. 4a and 4b provide examples of trajectories that are suitable for an ROI of a single breast. One manner in which to evaluate the multiple suitable trajectories is to determine the amount of exposure of the source to non-ROI. In the 2-dimensional examples of FIGS. 4a and 4b, the amount of exposure may be determined by calculating the area outside of the ROI which is exposed to source (i.e., the non-ROI which is subjected to the source). Comparing the figures, trajectory "X" to "Z" exposes more non-ROI area to the source than trajectory "A" to "C." Therefore, trajectory "A" to "C" is considered a better trajectory than trajectory "X" to "Z" based on this single criterion.

The 2-dimensional examples shown in FIGS. 4a and 4b are merely for illustrative purposes. In a 3-dimensional region of interest, exposure of the source to a volume (as opposed to an area) of the object may be calculated. A trajectory with a smaller non-ROI volume may be preferred over a trajectory with a greater non-ROI volume. Further, in the example given for FIGS. 4a and 4b, the non-ROI areas are given equal weight. Though, if a part of an object may be considered particularly sensitive to exposure by the source, exposure of the source to that sensitive part of the object may be accounted for by assigning a greater weight. For example, a part of the object which is more sensitive to exposure to the source may be weighted greater than other less sensitive parts of the objects.

Further, a trajectory may be selected from multiple suitable trajectories based on imaging effort. Examples of imaging effort include, but are not limited to, imaging time and ability to image. For example, a trajectory which requires a greater time to obtain the data may be less desirable than a trajectory which may obtain the data quicker. As another example, depending on the configuration of the object, certain trajectories may be more difficult to image.

Trajectories may be selected to scan for an ROI for a specific object or may be selected to scan for an ROI for a generalized object. For example, a trajectory may be selected to scan a right breast for a specific patient. The trajectory may thus be tailored for the shape of the right breast of the specific patient to meet certain factors, such as minimizing exposure to source. Alternatively, a trajectory may be selected for scanning a single breast of any patient (or a group of patients with a certain weight, height, etc.). Thus, logic may be used to determine a preferred trajectory for an ROI for a generalized object, and the trajectory may thereafter be programmed into imaging system 300 so that the trajectory need not be re-calculated for every patient. In another embodiment, if a trajectory is fixed, the method and system may determine which ROI may be imaged using the fixed trajectory. Specifically, an ROI or multiple ROIs may be determined that may be imaged from data generated with a source traveling via the fixed trajectory. For example, for a fixed trajectory, portions of an object which allows for support segments to fill a region may be identified so that the region may be images.

The following is an example of trajectories which may be used for imaging. Let the support of the image function $f(\vec{r})$ under consideration be confined within a cylinder of a radius $\rho_s$ and height $z_s$, and let the central axis of this cylinder coincide with the z-axis of the fixed-coordinate system. One may use $\vec{r}$ to denote a spatial vector, which may be written as $\vec{r} = (x, y, z)$ in the fixed-coordinate system. Therefore, one may assume that:

$$f(\vec{r}) = 0 \; x^2 + y^2 > \rho_s^2, \; z<0, \; \text{or} \; z>z_s. \tag{1}$$

Consider a general scanning trajectory displayed in FIGS. 4a and 4b, which is assumed to be characterized by a vector $\vec{r}_0(s)$ that is a function of the path length s, defined implicitly by:

$$\left| \frac{d\vec{r}_0(s)}{ds} \right| = 1. \tag{2}$$

The path length provides one parameter with which points along the trajectory can be identified. The reconstruction theory discussed in detail below may make use of derivatives of the source position along the trajectory, and employing the path length as a parameter, may avoid coordinate singularities and multivaluedness. In the fixed, Cartesian coordinate system, one may write $\vec{r}_o(s)=(x_o(s), y_o(s), z_o(s))$. The distance between a point on the trajectory and the z-axis is thus given by:

$$\rho(s)=\sqrt{x_o^2(s)+y_o^2(s)} \quad (3)$$

and the distance from the origin to a point on the trajectory may be given by:

$$R(s)=\sqrt{x_o^2(s)+y_o^2(s)+z_o^2(s)} \quad (4)$$

The detector, identified as element 320 in FIG. 3, is specified with a flat-panel geometry and assumed to rotate and translate so that the line from the source spot to the midpoint of the detector remains perpendicular to the detector plane. As discussed above, detector 320 and source 312 may rotate and translate with one another. Though the detector has a flat-panel geometry in the present example, detector 320 may be curved, or may comprise sections 322 which may move independently of one another. Further, the distance S(s) between the source spot and the detector plane may vary with path length.

Figure 5B:
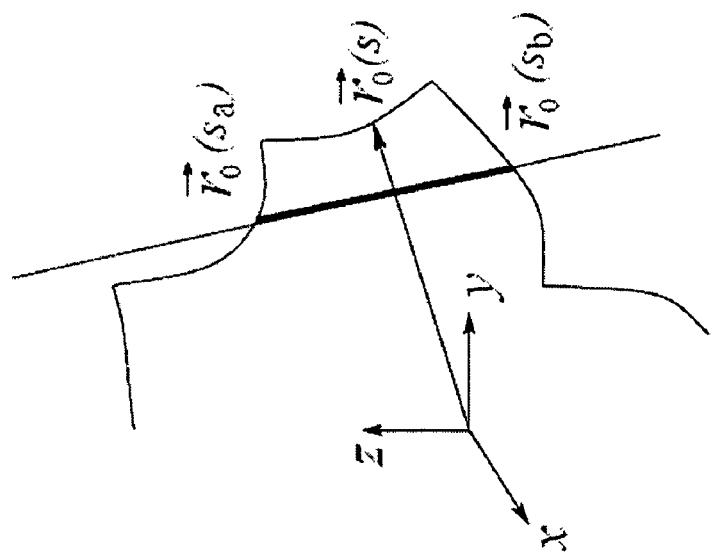
FIG. 5b is a side view of the general trajectory $\vec{r}_0(s)$ shown in FIG. 5a with a chord-line shown.
Figure 5A:
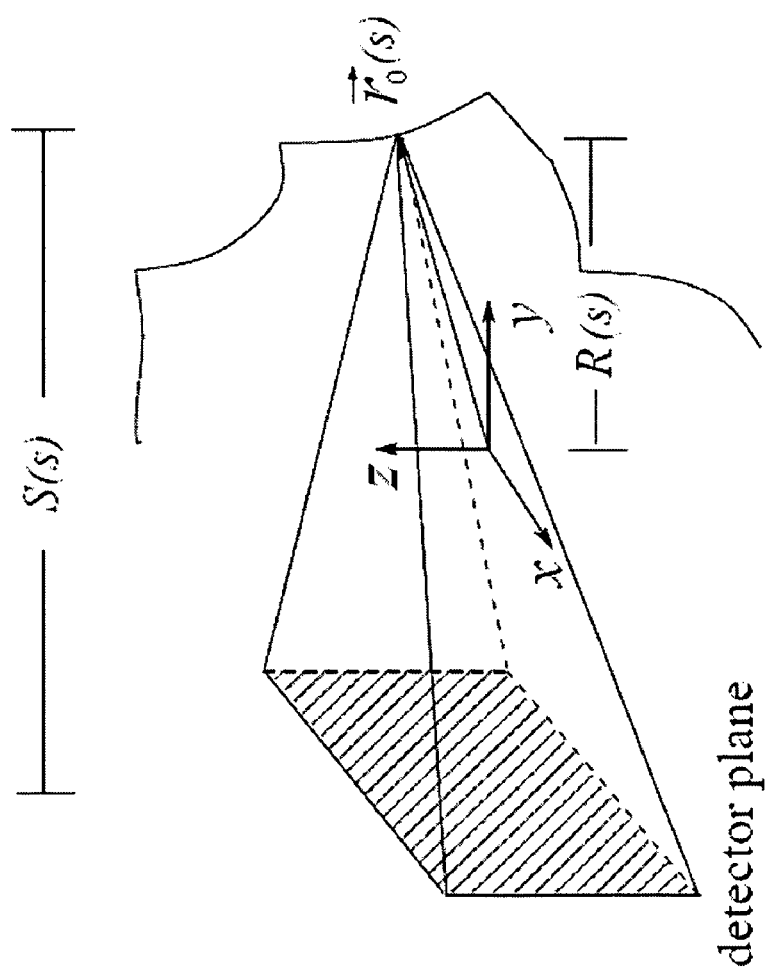
FIG. 5a is a side view of a general trajectory $\vec{r}_0(s)$ and a detector plane.

Referring to FIG. 5a, there is shown a general trajectory characterized by $\vec{r}_0(s)$. R(s) (or S(s)), shown in FIG. 5a, may denote the distance between point s on the trajectory and the z-axis (or the detector plane). Referring to FIG. 5b, there is shown a straight line (in bold) intersecting the trajectory at $s_a$ and $s_b$. This straight line is an example of a chord-line, and the portion of the chord-line between $\vec{r}_0(s_a)$ and $\vec{r}_0(s_b)$, which is indicated as the bold thick line segment, may be referred to as the chord. The general trajectory shown in FIGS. 5a and 5b includes a finite number of kinks at which it may not differentiable. Without the loss of generality, it is assumed that $s_a \leq s_b$. The segment of the trajectory, $s \in [s_a, s_b]$ may be referred to as a trajectory segment. One may use the following equation to denote the direction of the chord-line:

$$\hat{e}_c = \frac{\vec{r}_0(s_b) - \vec{r}_0(s_a)}{|\vec{r}_0(s_b) - \vec{r}_0(s_a)|} \quad (5)$$

Any point $\vec{r}$ on the chord-line may be expressed as:

$$\vec{r} = \frac{1}{2}[\vec{r}_0(s_a) + \vec{r}_0(s_b)] + x_c \hat{e}_c, \quad x_c \in \mathbb{R} \quad (6)$$

Further, one may refer to the segment on the chord-line between points $\vec{r}_0(s_a)$ and $\vec{r}_0(s_b)$ as the chord. A point $\vec{r}$ on the chord may thus be expressed as:

$$\vec{r} = \frac{1}{2}[\vec{r}_0(s_a) + \vec{r}_0(s_b)] + x_c \hat{e}_c, \quad x_c \in [-l, l], \quad (7)$$

where $l = \frac{1}{2}|\vec{r}_0(s_b) - \vec{r}_0(s_a)|$ denotes one half of the chord length. In the example of a helical trajectory, the path length s is proportional to the rotation angle $\lambda$, and when the $s_a$ and $s_b$ are within one turn, the chord-line and the chord can be understood as a PI-line and PI-line segment, respectively. Though, other types of trajectories may be used. And, other types of chords, such as multiple PI-lines, may be used.

Figure 6:
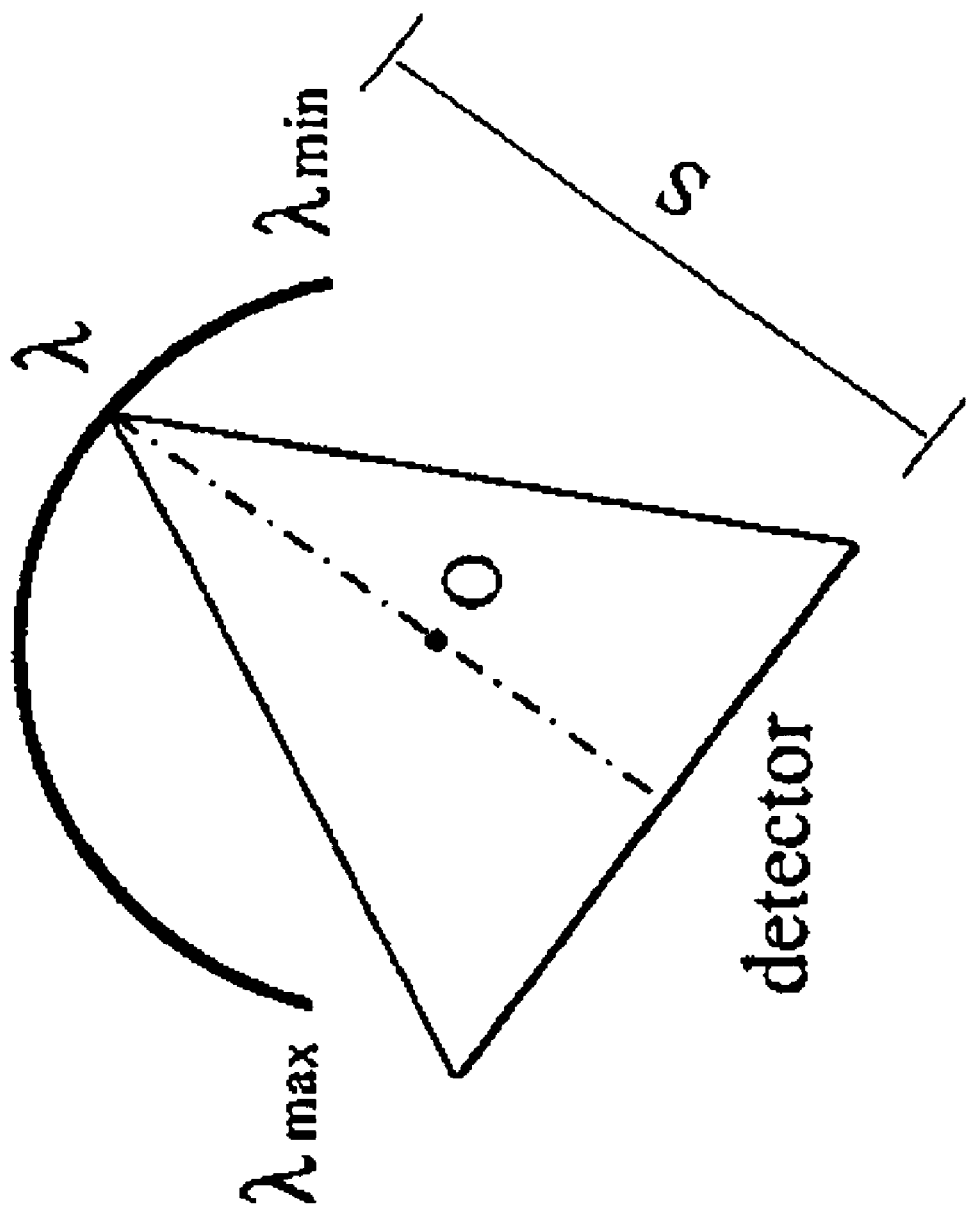
FIG. 6 is a schematic of a fan-beam configuration with the middle line of the fan-beam passing through a center of rotation O.

The concept of chords may be applied to specific trajectories. For example, PI-lines may be used for image reconstruction of a fan-beam scan over a portion of a circular source trajectory, as shown in FIG. 6. Specifically, FIG. 6 shows a schematic of a fan-beam configuration. The starting angle for the source trajectory is designated as $\lambda_{min}$ and the ending angle as $\lambda_{max}$. The middle line of the fan beam, shown in FIG. 6, passes through a center of rotation O and the distance between the source and the detector is designated as S.

The PI-line segment is a straight line segment joining two points labeled by the scanning angles $\lambda_1$ and $\lambda_2$, as shown in FIG. 7a. $x_\pi$ is used to denote the coordinate of a point on the PI-line segment with $(x_\pi, \lambda_1, \lambda_2)$ as the PI-line coordinates. The region $\Omega R$ enclosed by the source trajectory and the PI-line segment specified by $\lambda_{min}$ and $\lambda_{max}$, shown in FIG. 7b, may be completely filled by non-intersecting PI-line segments. One example of non-intersecting PI-line segments which completely fill region $\Omega R$ is displayed as a set of parallel lines in FIG. 7b. Therefore, each point within region $\Omega R$ may belong to one and only one of these parallel PI-line segments. Further, the relationship between the fixed coordinates (x, y) and the PI-line coordinates $(x_\pi, \lambda_1, \lambda_2)$ is determined by:

$$x = R[(1-t)\cos \lambda_1 + t \cos \lambda_2] \quad (8)$$

$$y = R[(1-t)\sin \lambda_1 + t \sin \lambda_2] \quad (9)$$

where $t \in [0, 1]$ is related to $x_\pi$ through:

$$x_\pi = (t-\tfrac{1}{2})|\vec{r}_0(\lambda_1) - \vec{r}_0(\lambda_2)| \quad (10)$$

Therefore, $x_\pi = 0$ indicates the middle point of the PI-line segment. In the fixed-coordinate system, the source trajectory $\vec{r}_0(\lambda)$ may be expressed as:

$$\vec{r}_0(\lambda) = (R \cos \lambda, R \sin \lambda)^T \quad (11)$$

It may also be beneficial to introduce a rotation-coordinate system $\{u, w\}$ for the present example, for characterizing data on the detector. It may be assumed that $\vec{r}_0(\lambda)$ is the origin of the rotation-coordinate system. Referring to FIG. 7c, there is shown a fixed-coordinate system (x, y) with its origin on the center of rotation of the source, the rotation-coordinate system $\{u, w\}$ with its origin on the source point, and a radius R of the source trajectory. For a rotation angle $\lambda$ in the fixed-coordinate system, as shown in FIG. 7c, the unit vectors along the u- and w-axis may be written as $\hat{e}_u(\lambda) = (-\sin \lambda, \cos \lambda)^T$ and $\hat{e}_w(\lambda) = (\cos \lambda, \sin \lambda)^T$. Furthermore, the fixed and rotation coordinates, (x, y) and $\{u, w\}$, of a point within $\Omega R$ are related through:

$$x = -u \sin \lambda + (w+R)\cos \lambda. \quad (12)$$

$$y = u \cos \lambda + (w+R)\sin \lambda. \quad (13)$$

Without loss of generality, considering a line detector that is always parallel to $\hat{e}_u(\lambda)$ and that is at a distance S from the source, $u_d$ as the coordinate of a point on the detector may be expressed as:

$$u_d = -(S/w)u \quad (14)$$

Referring back to the general trajectory example shown in FIGS. 5a-b, one may assume that the trajectory satisfies two conditions: (1) $\rho(s) > \rho_s$ or $R(s) > R_s$; and (2) $\vec{r}_0(s)$ is continuous and piece-wise (first order) differentiable with respect to the arc length s. Condition (1) indicates that the trajectory never intersects with the support cylinder (or, equivalently, the image support). Moreover, using path length to parameterize the source trajectory avoids coordinate singularities in evaluating the derivative along the source trajectory. Condition (2) is rather general in that it may be satisfied by a wide variety of trajectories, including those that may be potentially usefully in imaging, such as practical CT-imaging applications. One example of a trajectory which satisfies condition (2) is shown in FIG. 5b.

As discussed above, many trajectories may be suitable for imaging. One possible family of source trajectories includes generalizations of the helical trajectory described as follows:

$$\vec{r}_0(s[\lambda])=(R(\lambda)\cos\lambda, R(\lambda)\sin\lambda, Z(\lambda)) \quad (15)$$

where $\lambda$ denotes the rotation angle, and the path length $s(\lambda)$ is related to the rotation angle $\lambda$ through $$s(\lambda)=\int_0^\lambda \left|\frac{d\vec{r}_0(\lambda')}{d\lambda'}\right| d\lambda' \quad (16)$$

With this parameterization, the helical trajectory has a variable radius $R(\lambda)$ and a variable pitch $$\frac{dZ(\lambda)}{d\lambda}.$$

As long as $d\vec{r}_0(s)/ds(=d\vec{r}_0(s[\lambda])/d\lambda \cdot d\lambda/ds)$ exists almost everywhere, the chord reconstruction methodology, discussed below, may be applied to reconstructing the image on chords from data acquired with this trajectory. When $R(\lambda)=R_0$ and $$Z(\lambda)=\frac{h}{2\pi}\lambda,$$

the equation for $\vec{r}_0(s[\lambda])$ specifies the conventional helical trajectory with a constant radius $R_0$ and constant pitch length h. Also, both saddle and tilted helical trajectories may fit within this general helix parameterization. In particular, the saddle trajectory may be determined by:

$$\vec{r}_0(s[\lambda])=(R_0\cos\lambda, R_0\sin\lambda, h\cos 2\lambda) \quad (17)$$

and wherein the tilted helical trajectory can be expressed as:

$$\vec{r}_0(s[\lambda])=\left(R_0\cos\lambda, R_0\sin\lambda, \cos\mu, R_0\sin\lambda\sin\mu+\frac{h}{2\pi}\lambda\right) \quad (18)$$

where $\mu$ is a constant indicating the angle between the z-axis and the actual rotation axis of the tilted CT gantry. For both saddle and tilted helical trajectories, $$\frac{d\vec{r}_0(s)}{ds}$$

exists. Therefore, the reconstruction methodology may be applied to reconstructing the image on chords from data acquired with these trajectories.

Figure 8C:
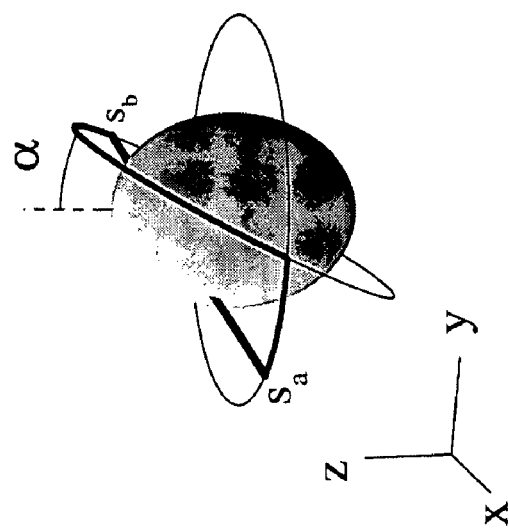
FIGS. 8a-c shows examples of different possible source trajectories, including, respectively, a generalized helix trajectory, a circle-line trajectory, and a two-circle line trajectory.
Figure 8B:
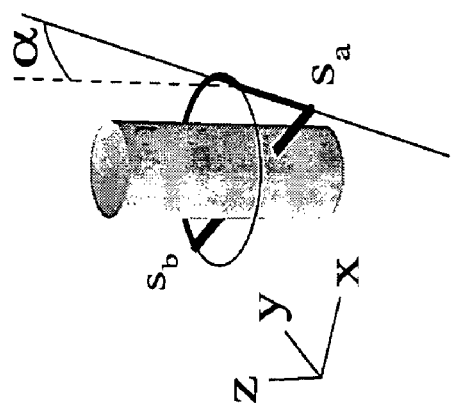
Figure 8A:
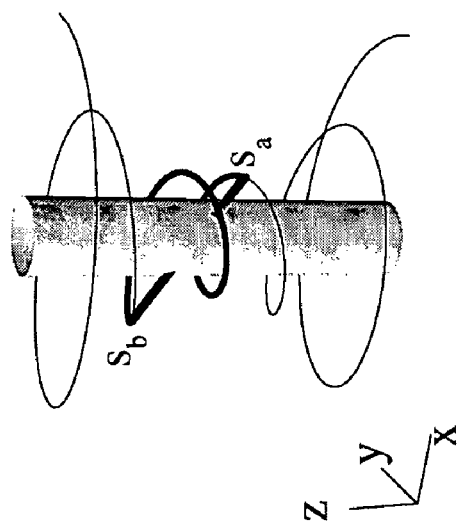

Referring to FIGS. 8a-c, there are shown examples of different possible source trajectories for the chord reconstruction discussed below. FIG. 8a shows a generalized helix trajectory, FIG. 8b shows a circle-line trajectory, and FIG. 8c shows a two-circle trajectory. The trajectories in FIGS. 8b and 8c are only piecewise differentiable. The chord reconstruction methodology, discussed in more detail below, may support trajectories that have a finite number of kinks in them. Specifically, these are trajectories where $dr_0(s)/ds$ does not exist at a finite number of isolated points on the trajectories. The source may traverse the trajectory segment (the thick curve shown in the figures) in order to obtain the image on the chord (thick line).

The circle-line trajectory can be expressed in terms of path length as follows:

$$\vec{r}_0(s)=\begin{cases} (0, s\sin(\alpha), s\cos(\alpha)) & s\leq 0 \\ \rho_{cl}\left(\cos\frac{s}{\rho_{cl}}-1, \sin\frac{s}{\rho_{cl}}, 0\right) & 0<s<2\pi\rho_{cl} \\ (0, (s-2\pi\rho_{cl})\sin(\alpha), (s-2\pi\rho_{cl})\cos(\alpha)) & 2\pi\rho_{cl}<s \end{cases} \quad (19)$$

where $\rho_{cl}$ may indicate the radius of the circle, and the line is $\alpha$ radians from vertical in the y-z plane. Similarly the two-circle trajectory may be expressed as:

$$\vec{r}_0(s)=\begin{cases} \rho_{cc}\left(\cos\frac{s}{\rho_{cc}}, \sin\frac{s}{\rho_{cc}}, 0\right) & -2\pi\rho_{cc}<s<0 \\ \rho_{cc}\left(\cos\frac{s}{\rho_{cc}}, \sin(\alpha)\sin\frac{s}{\rho_{cc}}, \cos(\alpha)\sin\frac{s}{\rho_{cc}}\right) & 0\leq s<2\pi\rho_{cc} \end{cases} \quad (20)$$

where $\rho_{cc}$ denotes the radius of the circles. In each case, the indicated chord may be reconstructed when the source follows the corresponding trajectory segment. Moreover, there maybe more than one path that connects the endpoints of the chord in which case either path may be utilized to reconstruct the chord. For the circle-line trajectory shown in FIG. 8b, the derivative with respect to path length does not exist where the circle and line join, but as long as the trajectory is continuous at that point, the chord reconstruction methodology discussed below may be applied. The situation is the same for the two-circles trajectory, shown in FIG. 8c, at the joint of both circles.

Modifying the Source During Data Acquisition

As discussed above, typical imaging systems require that data be acquired for an entire section of an object and that all the acquired data be processed, even if an image of only a subsection of the object is sought. In one aspect of the invention, if an ROI is a portion of an object support, such as a part of a contiguous cross-section or a part of a volume, at least one characteristic of the source may be selected which acquires data that is less than that sufficient to image the entire object support, but which acquires data that is at least sufficient to image the ROI. For example, the control of the at least one characteristic of the source may enable illumination of support segments which fill the ROI.

As discussed above, source 312 may comprise any device which generates a signal (or a combination of signals) that may be received from detector 320. Characteristics of the source that may be controlled include any aspect of the source which may affect the signal received by the detector including, but not limited to: illumination coverage (e.g., aperture setting of beam, width of beam, modification of cone beam coverage, etc.); intensity of beam; and spectral distribution of beam. Typically, the characteristics of the source, such as the illumination coverage, remain fixed during imaging.

In another aspect of the invention, at least one characteristic of the source may be modified so that the data generated is less than that sufficient to image an object support. The characteristic may be changed so that it is constant as the source moves relative to the object. Or, the characteristic may be changed at least once as the source moves relative to the object. In one embodiment, the characteristic or characteristics of the source may be modified based on the ROI. For example, the characteristic of the source which is modified may comprise illumination coverage of the source. Specifically, the illumination coverage of the source may be modified so that the coverage is substantially directed to the ROI and substantially reduced for the non-ROI (or substantially not directed to the non-ROI). In this manner, exposure of the source to non-ROI may be reduced or minimized and exposure of the source to the ROI is sufficient to image the object (such as by generating support segments). This is advantageous when one may wish to reduce or limit exposure to the source, such as an x-ray source. Modification of the illumination coverage enables reduction of exposure to non-ROI areas or volumes while still maintaining illumination coverage to ROI areas or volumes.

As a general matter, illumination coverage may be modified based on the type of source used in the imaging system. If the source generates a fan beam, the aperture setting of source may be modified to change the angle of the fan beam, as discussed in more detail below. If the source generates a parallel beam, the width of beam may be modified. If the source generates a cone beam, the spread of the cone beam may be modified.

Moreover, modification of the characteristic or characteristics of the source may be dynamic, changing at any one or multiple points as the source travels relative to the object (e.g., the source moving with the object stationary, the source stationary and the object moving, or the source and object moving relative to one another). For example, an initial illumination coverage of the source may be selected as the source is initially directed at the object. The initial illumination coverage may be selected so that illumination to non-ROI areas is reduced or minimized. As the source travels relative to the object, the characteristic of the source (such as the illumination coverage) may be modified. The modification may be performed at discrete points along the trajectory. Or, the modification may be performed so that the characteristic is constant as the source travels relative to the object.

The following is an example of modifying a characteristic of the source during CT image scanning. Fan beam scanning is widely used in clinical CT systems for data acquisition. However, other types of scanning may be used for CT systems. As merely one example, cone-beam scanning (such as helical cone-bean scanning) may also be used in CT systems. In fan beam scanning, when the fan beam scan covers an angular range of $2\pi$ or $\pi$ plus the fan-beam angle, it is referred to as the full- or short-scan, respectively. A fan-beam scan over an angular range smaller than that in a short scan may be referred to as a reduced scan.

The fan-beam geometry with a circular trajectory is most widely used configuration in practice. However, other configurations may be used. In this configuration, the field of view (FOV) is determined by the open-angle of the fan beam and the radius R of the trajectory. Because certain image reconstruction methodologies for an ROI reconstruction, such as filtered-backprojection (FBP) discussed below, do not allow data truncations at any of the scanned views, the entire support of the image must be within the FOV. The following presents two situations in which data truncations occur in the data acquisition, and show that other image reconstruction methodologies, such as the backprojection-filtration (BPF) methodology discussed below, can exactly reconstruct images within an ROI in both situations in which data truncations occur. It is assumed that the scan includes a suitable trajectory over an angular range $\lambda_{min}$ and $\lambda_{max}$. As discussed above, a suitable trajectory may include one wherein a set of segments of chords defined by the trajectory fills the ROI. It is also assumed that at each view, $\lambda \in [\lambda_{min}$ and $\lambda_{max}]$ data are available on and only on the projection range of the support section, discussed in more detail below.

In the first situation, the open-angle of the fan-beam, and thus the FOV, remains fixed, whereas, in the second situation, the open-angle of the fan-beam at different views over the scanning angular range can change. As shown below, both situations generate sufficient data to satisfy $\lambda \in [\lambda_{min}$ and $\lambda_{max}]$ data are available on and only on the projection range of the support section. In the first situation, the open-angle of the fan-beam at the scanned views remains fixed. Because the fan-beam has a fixed open-angle, data in $[-u_{dm}, u_{dm}]$ can always be collected, where $\pm u_{dm}$ depict the points at which the two out-most rays in the fan-beam intersect with the detector array. It is assumed that the ROI is covered completely by the FOV and that a set of PI-lines exists, which fill the ROI and do not intersect the support outside the ROI. Under this assumption, it can be seen that, for all of the support-sections on the PI-lines within the ROI, their projection ranges on the detector satisfy $[u_{d1}, u_{d2}] \subseteq [-u_{dm}, u_{dm}]$. Therefore, for each of the support-sections, data are available in $[u_{d1}, u_{d2}]$ and thus sufficient data are generated. Even if the image support is larger than the FOV, meaning that measurements contain truncations, data in $[-u_{dm}, u_{dm}]$ and thus in $[u_{d1}, u_{d2}]$ are always available. Consequently, the image on the PI-line segment can exactly be reconstructed from data containing truncations by use of the fan-beam BPF methodology. Because this can be done for each of the selected PI-line segments that fill the ROI, the image within the ROI can thus be obtained. The following are two examples to illustrate a sufficient trajectory and sufficient amount of data.

Figures 9A, 9B, 9C:
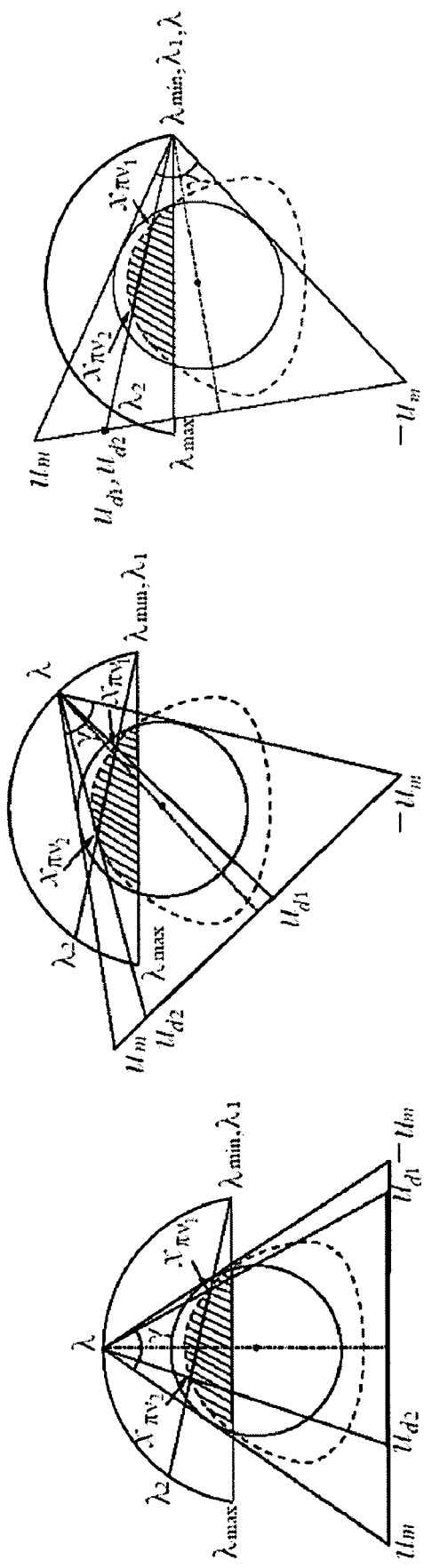
FIGS. 9a-c illustrate three views of data acquisition in a fan-beam scan with a fixed open angle.

Referring to FIGS. 9a-c, a fan-beam scan is shown over $[\lambda_{min}, \lambda_{max}]$ in which the open-angle of the fan-beam remains fixed and the FOV is enclosed by the solid circle. The scanned trajectory over $[\lambda_{min}, \lambda_{max}]$ is indicated by the thick curve, with the regions enclosed by the solid circle and by the dashed curve showing the FOV and the image support, respectively. The ROI considered is depicted as the shadow region and the support-section $[x_{\pi 1}, x_{\pi 2}]$, shown as the thick line segment between $x_{\pi 1}$ and $x_{\pi 2}$, denotes the intersection between the image support and a PI-line segment, specified by $\lambda_1$ and $\lambda_2$, that intersects with the image support. FIGS. 9a-c display, at three views $\lambda \in [\lambda_1, \lambda_2]$, the projection ranges of the support-section onto the detector, which are the thick segments between $[u_{d1}, u_{d2}]$ on the detector. $\pm u_m$ depict the points at which the two outmost rays in the fan-beam intersect with the detector, and the open-angle is formed by the two lines connecting $-u_m$ and $u_m$ respectively, to the source at $\lambda$.

As shown in FIGS. 9a-c, the entire support of the image, indicated by the dashed curve, is larger than the FOV. Therefore, projection data acquired at most of the views $\lambda \in [\lambda_{min}, \lambda_{max}]$ would contain truncations. Consider image reconstruction in the ROI, indicated as shaded region, that is confined within the FOV. A set of PI-line segments may be selected, each of which is specified by $\lambda_1$ and $\lambda_2$, where $\lambda_1 = \lambda_{min}$ and $\lambda_2 \in [\lambda_{min}, \lambda_{max}]$. Therefore, the ROI can completely be filled by these PI-line segments, and is thus a suitable trajectory. Specifically, for a PI-line segment specified by $\lambda_1$ and $\lambda_2$ in the set, it is observed that, for image reconstruction on this PI-line segment, $[\lambda_1, \lambda_2] \in [\lambda_{min}, \lambda_{max}]$ and thus that the scanning angular range is suitable.

In FIGS. 9a-c, displayed are the support-section of the PI-line segment specified by $\lambda_1$ and $\lambda_2$ and its projection ranges at three different views $\lambda \in [\lambda_1, \lambda_2]$. It can be seen that, despite the fact that the projections of the full image at these views contain truncations, data collected in $[-u_{dm}, u_{dm}]$ contain the necessary data in $[u_{d1}, u_{d2}]$ (i.e., on the projection range of the support-section) because $[u_{d1}, u_{d2}] \subseteq [-u_{d1}, u_{dm}]$. This means that an exact image may be reconstructed on the support-section (or, equivalently, on its PI-line segment) by use of the fan-beam BPF methodology. The above analysis also applies to all of the PI-line segments that fill completely the ROI. Therefore, images on these PI-line segments and, consequently, in the ROI can be reconstructed exactly by use of the fan-beam BPF algorithm.

In the second situation, the open-angle of the fan beam may change at different views. As discussed above, a characteristic of the source, such as the open angle of the fan-beam, may be modified as the source travels relative to the object. It is assumed that the support-sections on the selected PI-line segments are within the ROI and that the open-angle of the fan beam changes in such a way that the fan-beam at each view contains (or substantially contains) only rays that intersect with the ROI. This assumption allows data to be collected on and only on the projection ranges (i.e., in and only in $[u_{d1}, u_{d2}]$) of the support-sections of the PI-line segments that fill completely the ROI. Therefore, even though data so collected may contain severe truncations, they contain the necessary data to support exact reconstruction. Consequently, the image on the PI-line segment can be reconstructed exactly from these data by use of the fan-beam BPF methodology.

Figures 10A, 10B, 10C:
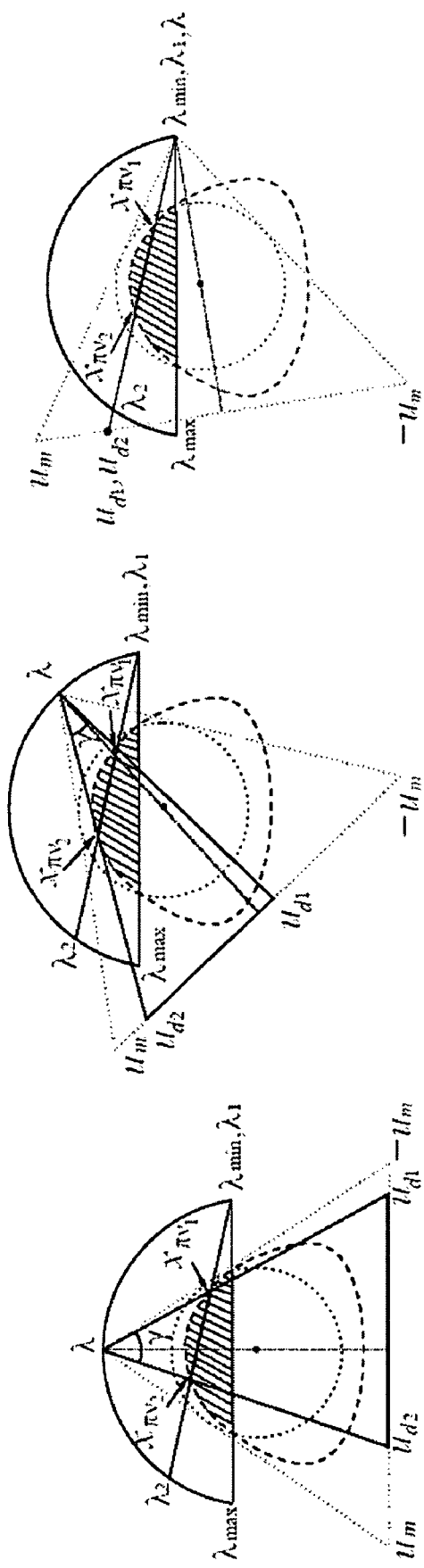
FIGS. 10a-c illustrate three views of data acquisition in a fan-beam scan, similar to the views shown in FIGS. 9a-c, with a varying open angle.

Referring to FIGS. 10a-c, there is shown data acquisition in a fan-beam scan, similar to FIGS. 9a-c. The notations and symbols are identical to those in FIGS. 9a-c except that the open-angle of the fan-beam can vary at different views $\lambda \in [\lambda_1, \lambda_2]$. In particular, the open-angle is now formed by the two lines connecting $u_{d1}$ and $u_{d2}$, respectively, to the source at $\lambda$. The original FOV and fan-beam are indicated by the dotted curves. As shown in FIGS. 10a-c, displayed are the projection ranges of the support-section on a PI-line segment, specified by $[\lambda_1, \lambda_2]$, at three different views $\lambda \in [\lambda_1, \lambda_2]$. The open-angles at the three views: (1) are smaller than the open-angle covering the FOV; (2) are substantially different than the three open-angles shown in FIGS. 9a-c, and (3) cover the support-section completely. For example, the open-angle in FIG. 10c is zero because only one ray is needed to cover the support-section on this PI-line segment at this view. Consequently, data can be collected at $u_d \in [u_{d1}, u_{d2}]$ (i.e., on the projection ranges of the support-section of the PI-line segment). Therefore, even in limiting the output of the source, such as by narrowing the fan beam, sufficient data may be collected to reconstruct an exact image on the PI-line segment by use of the fan-beam BPF algorithm. Moreover, the above analysis applies to all of the PI-line segments in the selected set of PI-line segments covering the ROI. Therefore, the image on these PI-line segments and, consequently, in the ROI can be reconstructed exactly by use of the fan-beam BPF algorithm. The varying open-angle in FIGS. 10a-c was shown for a single support-section. When the entire ROI (i.e., the shaded region in FIGS. 10a-c) is considered, the open-angle may be varied so that the fan-beam only covers the ROI at all of the views $\lambda \in [\lambda_1, \lambda_2]$.

Figure 11B:
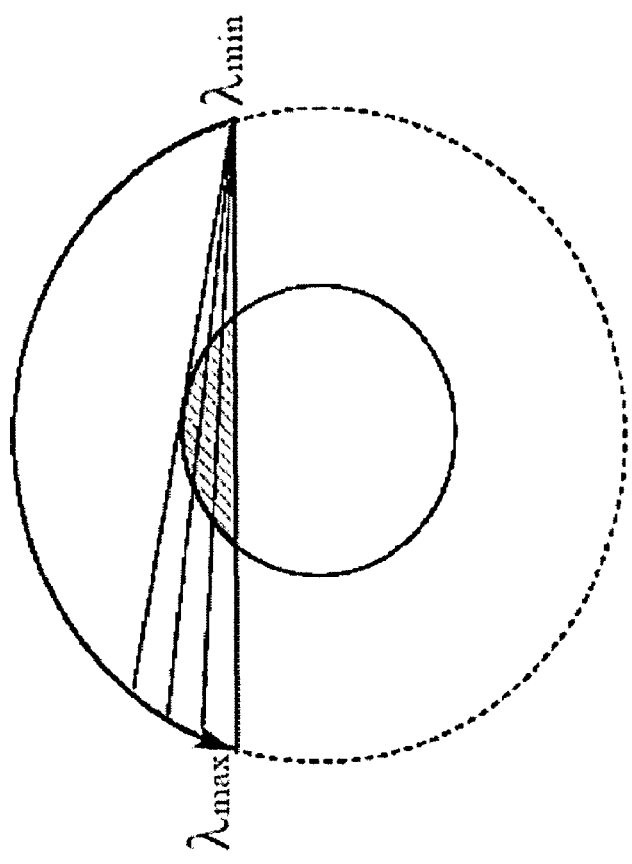
FIGS. 11a-b illustrate two scanning trajectories that cover angular ranges $[\pi, 2\pi]$ and $[1.2\pi, 1.8\pi]$, with the shaded areas designating the regions of interest to be reconstructed.
Figure 11A:
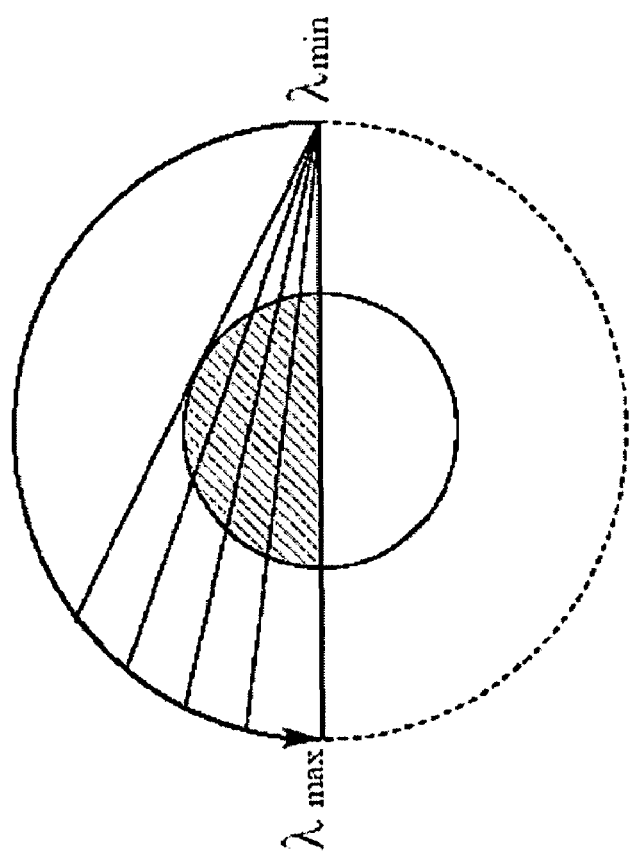

The following is a computer-simulation study to demonstrate and verify quantitatively the proposed fan-beam BPF methodology. In the numerical study, a circular fan-beam configuration is considered in which the trajectory has a radius of R=27.0 cm and the (virtual) one-dimensional (1-D) detector array is at the center of rotation. In this case, S=R=27.0 cm. The 1D detector array consists of 512 square-shape elements each of which has a size of 0.55 mm. The fan-beam configuration thus admits a FOV with a radius of 12.5 cm when the open-angle of the fan-beam remains a fixed for all projection views. The 2D head phantom is used, having an elliptical support with half axes of 9.6 cm and 12.0 cm, along the x- and y-axis, respectively. Two scanning trajectories are considered, shown in FIGS. 11a and 11b. Specifically, FIG. 11a covers an angular range of $[\pi, 2\pi]$ and FIG. 11b covers an angular range of $[1.2\pi, 1.8\pi]$. The shaded areas in FIGS. 11a-b are the ROIs to be reconstructed. Further, as shown in FIGS. 11a-b, a converging set of PI-line segments is used to fill the ROI. Each PI-line segment in the set is specified by $\lambda_1$ and $\lambda_2$, where $\lambda_1 = \lambda_{min}$ and $\lambda_2 \in [\lambda_{min}, \lambda_{max}]$.

Figure 12A:
FIG. 12a illustrates data collected over $[\pi, 2\pi]$ in FIG. 11a by use of a fan-beam with a fixed open angle.
Figure 12B:
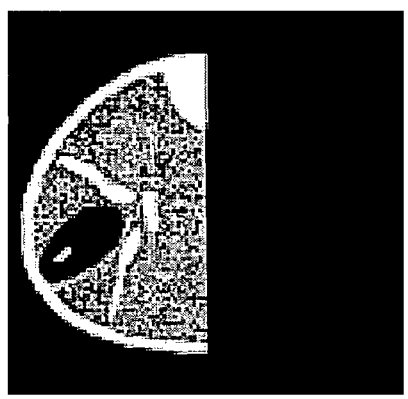
FIG. 12b illustrates an image reconstructed on PI-line segments using the data illustrated in FIG. 12a and a filtered-backprojection methodology.
Figure 12C:
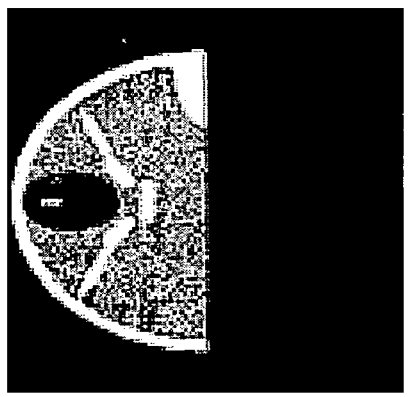
FIG. 12c illustrates a reconstructed image displayed in terms of fixed coordinates, which is converted from the image reconstructed in FIG. 12b.
Figure 12D:
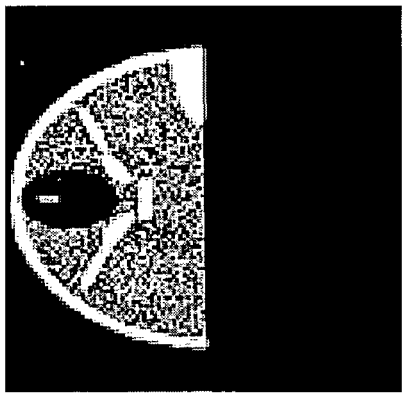
FIG. 12d illustrates a reconstructed noisy image for the image reconstructed in FIG. 12c.

For the scanning trajectory in FIG. 11a, using the fan-beam configuration with a fixed open-angle and the head phantom described above, data is generated at 512 projection views uniformly distributed over $[\pi, 2\pi]$, which are shown in FIG. 12a. In this case, it is assumed that data contain no truncations at each view. Because data contain no truncations, the FBP-based methodology may be used for reconstructing an exact image within the ROI on the PI-line segments intersecting with the ROI. This reconstructed image is shown in FIG. 12b in which each horizontal line represents a PI-line segment. Using the relationship between the PI-line coordinates $(x_\pi, \lambda_1, \lambda_2)$ and the fixed coordinates $(x, y)$ which is discussed above, the image presented in terms of the PI-line coordinates in FIG. 12b can be converted to an image presented in terms of the fixed coordinates, as shown in FIG. 12c. In an attempt to demonstrate how the FBP-based algorithm respond to data noise, Gaussian noise is added to the generated noiseless data. The standard deviation of the Gaussian noise is 2% of the maximum value of the fan-beam data. From the noisy data, a "noisy" image is reconstructed within the ROI, which is shown in FIG. 12d. Images similar to those in FIG. 12c and 12d may also be reconstructed from data displayed in FIG. 12a by use of the fan-beam BPF methodology. Moreover, data in FIG. 12a contain more information than what is needed for exact image reconstruction in that ROI by use of the fan-beam BPF algorithm.

Figure 13A:
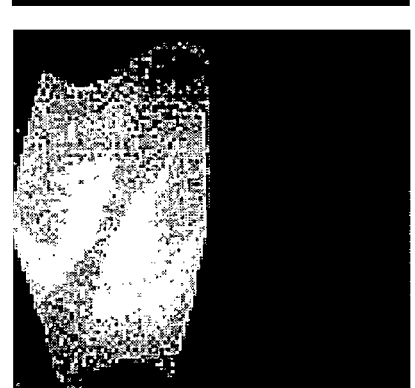
FIG. 13a illustrates data collected over $[\pi, 2\pi]$ in FIG. 11a by use of a fan-beam with a varying open angle.
Figure 13B:
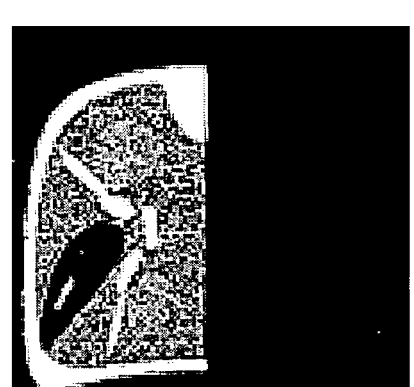
FIG. 13b illustrates an image reconstructed on PI-line segments using the data illustrated in FIG. 13a and a backprojection-filtration methodology.
Figure 13C:
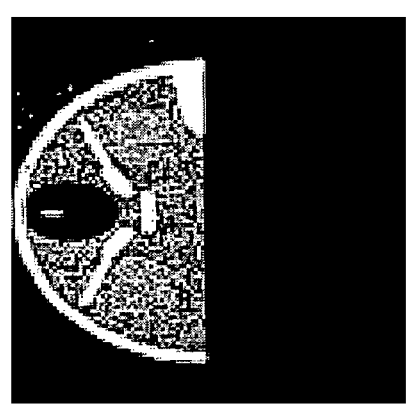
FIG. 13c illustrates a reconstructed image displayed in terms of fixed coordinates, which is converted from the image reconstructed in FIG. 13b.
Figure 13D:
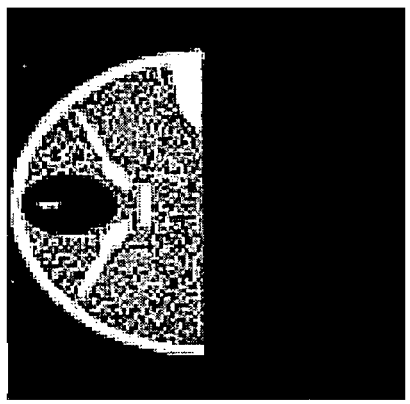
FIG. 13d illustrates a reconstructed noisy image for the image reconstructed in FIG. 13c.

For the scanning trajectory in FIG. 11a, using the fan-beam configuration with a varying open-angle and the head phantom described above, data is generated at 512 projection views uniformly distributed over $[\lambda, 2\pi]$, which are displayed in FIG. 13a. The open-angle was varied such that data were acquired at and only at $u_d \in [u_{d1}, u_{d2}]$ (i.e., on the projection range of the support-section on the PI-line segments) for the scanned views. Therefore, this set of data is sufficient to reconstruct the image. Comparison of FIGS. 13a and 13b indicates that data acquired with the varying open-angle contain truncations. Therefore, the FBP-based algorithms cannot reconstruct exactly an image within the ROI from this set of truncated data. However, as mentioned above, PI-line segments that intersect with the ROI can exactly (or substantially exactly) be reconstructed by use of the fan-beam BPF methodology or the MFBP methodology. FIG. 13b displays the reconstructed image on PI-line segments. The PI-line coordinate is normalized to the length of each PI-line segment. Again, using the relationship between the PI-line coordinates and the fixed coordinates, discussed in more detail below, the image presented in terms of the PI-line coordinates in FIG. 13b is converted to an image presented in terms of the fixed coordinates, which is shown in FIG. 13c. The fan-beam BPF algorithm was also used to reconstruct an image from data containing Gaussian noise, and the reconstructed noisy image is displayed in FIG. 13d.

Figure 14D:
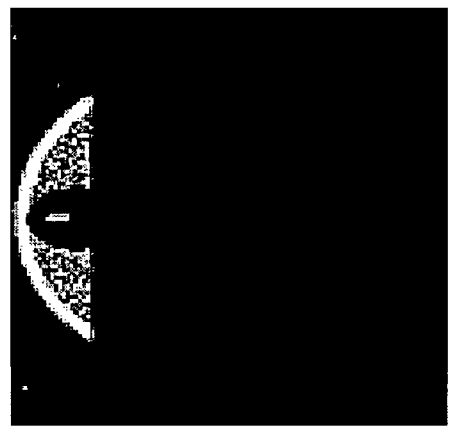
FIG. 14d illustrates a reconstructed noisy image for the image reconstructed in FIG. 14c.
Figure 14C:
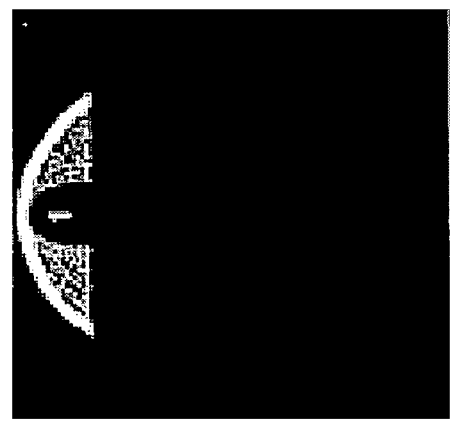
FIG. 14c illustrates a reconstructed image displayed in terms of fixed coordinates, which is converted from the image reconstructed in FIG. 14b.
Figure 14B:
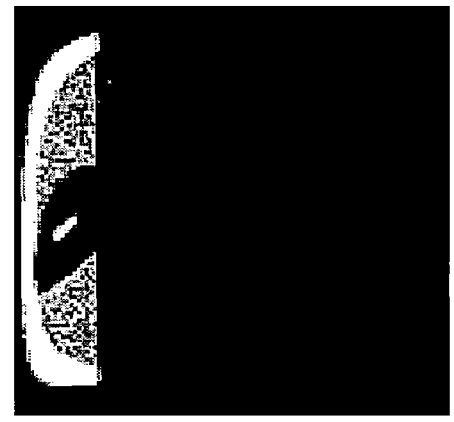
FIG. 14b illustrates an image reconstructed on PI-line segments using the data illustrated in FIG. 14a and a backprojection-filtration methodology.
Figure 14A:
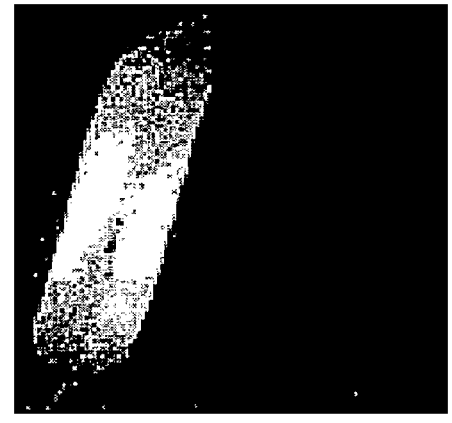
FIG. 14a illustrates data collected over $[1.09\pi, 1.91\pi]$ in FIG. 11a by use of a fan-beam with a varying open angle.

For the scanning trajectory in FIG. 11b, using the fan-beam configuration with a varying open-angle and the head phantom described above, data is also generated data at 416 projection views uniformly distributed over [1.09π, 1.91π], which are displayed in FIG. 14a. Again, the open-angle was varied such that data were acquired at and only at $u_d \in [u_{d1}, u_{d2}]$ (i.e., on the projection range of the support-section on the PI-line segments) for the scanned views. Therefore, this set of data is sufficient to reconstruct an image. Comparison of FIGS. 12a and 14a clearly indicates that this set of data contains severe truncations. In fact, data at all of the scanned views in [1.09π, 1.91π] contain truncations. The truncations occur only on one end of the detector array for some views such as the views near $\lambda_{min}=1.09\pi$. However, data truncations take place on both ends of the detector array for the rest of the scanned views. The FBP-based methodologies cannot reconstruct exactly an image within the ROI from this set of severely truncated data. However, as mentioned above, an exact image on PI-line segments that intersect with the ROI can be reconstructed by use of the fan-beam BPF methodology or the MFBP methodology. FIG. 14b demonstrates the reconstructed image on such PI-line segments. Based upon the relationship between the PI-line and fixed coordinates, discussed below, the image in FIG. 14b may be converted to an image in FIG. 14c, which is presented in terms of the fixed coordinates. The fan-beam BPF algorithm was also used to reconstruct an image from data containing Gaussian noise, and the reconstructed noisy image is displayed in FIG. 14d.

Modifying the Detector During Data Acquisition

As discussed above, detector 320 may comprise any device which senses a signal (or a combination of signals). The signal may originate from source 312 or may originate object 316. In another aspect of the invention, at least one characteristic of the detector may be modified during acquisition of the data for imaging. In one embodiment, the characteristic or characteristics of the detector may be modified based on the ROI. For example, the characteristic of the detector that is modified may comprise activation or deactivation of sections of the detector. Sections 322 of detector 320 may be enabled or disabled so that data sensed by detector 320 is substantially for the ROI and substantially not for non-ROI. In this manner, extraneous data may be reduced or minimized. In another embodiment, the data generated by the detector may be accepted or rejected based on the ROI. Data generated by sections 322 of detector 320 may be accepted or rejected so that data sensed by detector 320 is substantially for the ROI and substantially not for non-ROI. In this manner, extraneous data may be reduced or minimized. Detector 320 may determine whether data from a section is accepted or rejected. Alternatively, processing unit 304 may determine whether data from a section is accepted or rejected.

Generating an Image Based on Chords

After data acquisition, the data may be processed to generate a reconstructed image of a portion, or all, of the object. The reconstruction may be based on chords that fill at least a portion (such as all) of a region of interest (ROI). The chords used for reconstruction may be a connection between two points, such as a straight line or a section of a curve.

The chords may be based on any aspect of imaging, such as a non-fixed coordinate system. One such non-fixed coordinate system may be defined, at least in part, by the source trajectory or how the source travels relative to the object (e.g., the source moving with the object stationary, the source stationary and the object moving, or the source and object moving relative to one another). After the image is reconstructed on the non-fixed coordinate system, the image may be converted into a fixed coordinate system, such as a Cartesian coordinate system. Alternatively, the chords may be based on a fixed coordinate system, such as the Cartesian coordinate system.

For example, image reconstruction may be based, at least in part, on chords defined by the source trajectory. As discussed above, two points along the source trajectory may define a chord. Points along the chord may further be defined by a third point. Thus, the chords may be defined with a first point along the source path, a second point along the source path which is different from the first point, and a third point on a chord formed between the first point and the second point. The first and second points may be defined by scalars or may be defined by arc lengths along the source path. The entire ROI, either for a 2-Dimensional or 3-Dimensional ROI, may be defined by points along the chords defined by the source trajectory. Further, the image may be reconstructed using the chords. As merely one example, discussed in more detail below, the image may be reconstructed by identifying a set of chords that connect pairs of points along the source path, wherein the set of chords fill a volume for a region of interest in the body, calculating image densities on the chords from the collected data, and constructing a three-dimensional image based on the image densities and on the source path. Therefore, when using chords for reconstruction defined by the source trajectory, the reconstruction of the image may be based on a coordinate system defined by the source trajectory.

Figure 15C:
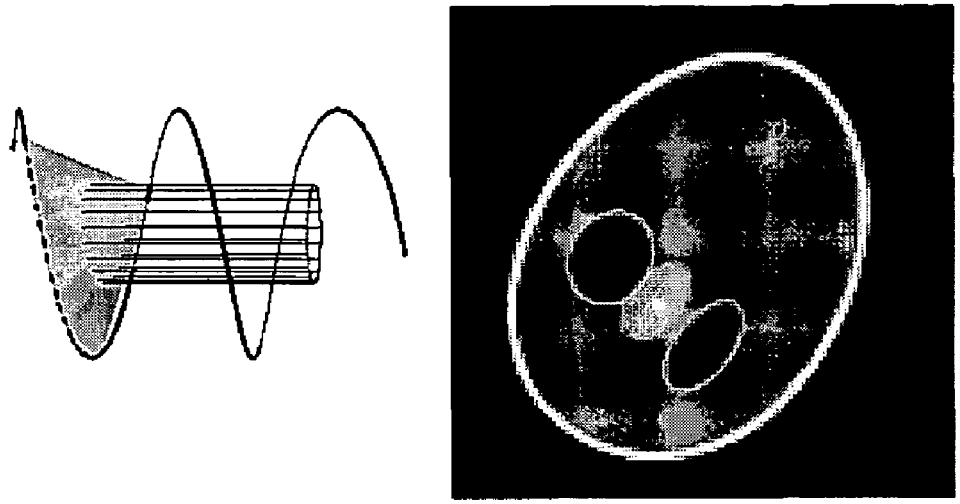
FIGS. 15a-c show an object which is cylindrical in shape being scanned with a helical source trajectory and corresponding reconstructed images.
Figure 15B:
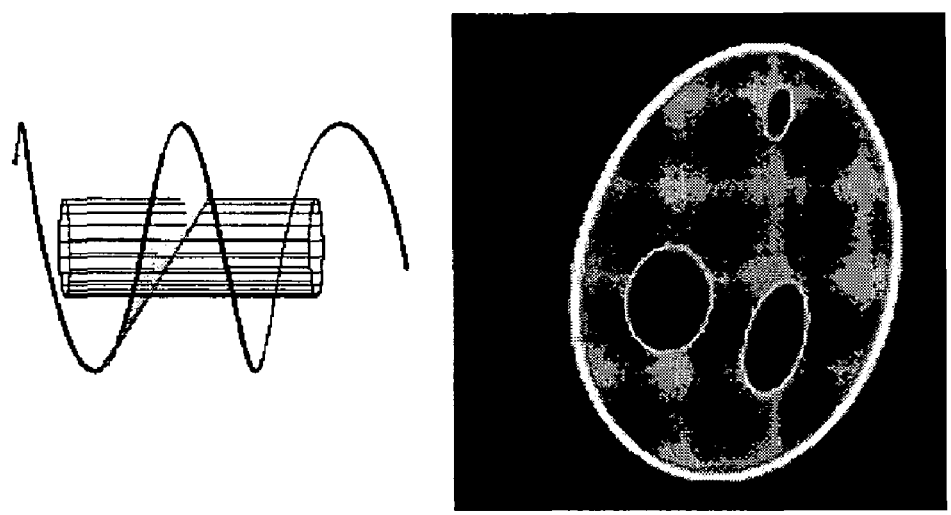
Figure 15A:
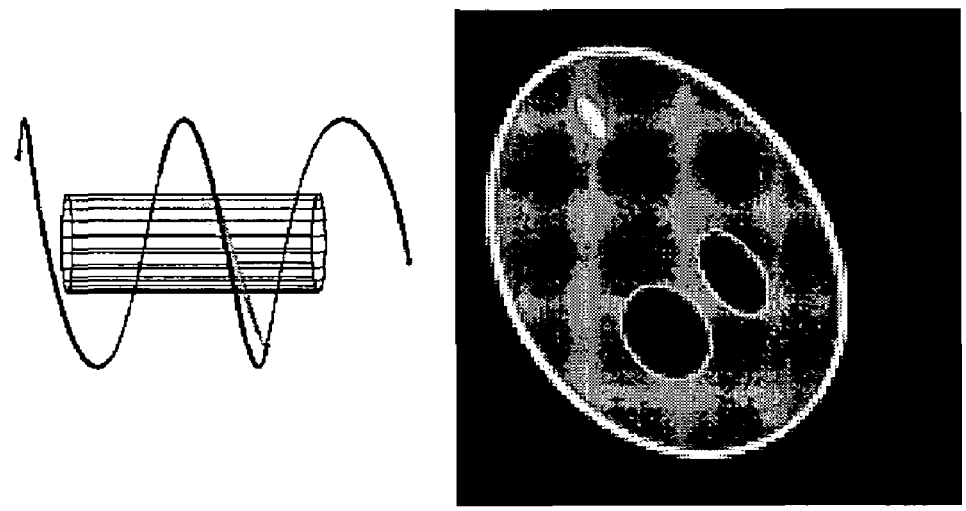

For example, FIGS. 4a and 4b, discussed above, define points along the chords for an entire area of an ROI. As another example, FIGS. 15a-c show an object which is cylindrical in shape being scanned with a helical source trajectory. The shape of the object and the type of trajectory are merely exemplary. Other objects may be scanned, and other trajectories may be used. Each point within an object may be defined by points on chords. For example, the chords defined by the source trajectory in FIGS. 15a-c may fill the entire volume of the cylindrical object by defining a series of planes which fill the object. Three of the planes are shown in FIGS. 15a-c with corresponding reconstructed images.

Since an ROI may be defined by at least a part of the chords, the image may therefore be reconstructed using the chords. Specifically, the image may be reconstructed on at least a part of the chords to generate the image for the ROI. In the example shown in FIGS. 4a and 4b, the image may be constructed on a segment of the chord which overlaps the ROI, or may be constructed over the entire chord. In the example shown in FIGS. 15a-c, the image may be constructed over surface areas which make up the volume of the ROI, or may be constructed over the entire surface area defined by the chords. Alternatively, the image may be constructed point by point to make up the volume of the ROI. A variety of methodologies may be used to reconstruct the image based on chords. Three methodologies, including filtered-backprojection (FBP), backprojection-filtration (BPF), and Minimum Filtration Backprojection (MFBP), are described in the following example to reconstruct the image. However, other methodologies may be used. Further, the example uses a cone-beam projection. Other projections may be used, including a fan-beam projection. Or, a projection may not be needed at all, such as in the case of PET scanning.

A cone-beam projection of the object function or density distribution may be defined as:

$$D(\vec{r}_0(s), \hat{\beta}) = \int_0^\infty dt f(\vec{r}_0(s) + t\hat{\beta}) \tag{21}$$

where the unit vector $\hat{\beta}$, indicating the projection direction of an individual x-ray passing through the point $\vec{r}'$, may be written as:

$$\hat{\beta} = \frac{\vec{r}' - \vec{r}_0(s)}{|\vec{r}' - \vec{r}_0(s)|} \quad (22)$$

and $\vec{r}' \in R^3$. $D(\vec{r}_0(s), \hat{\beta})$ may be referred to as physical data because they are assumed to be measurable. Assume that $\vec{r}$ is on a chord determined by $s_a$ and $s_b$ (two points on the source trajectory). For a generalized trajectory, suppose that there are N-1 kinks on the trajectory segment specified by $s \in [s_a, s_b]$, dividing it into N connected pieces. The N-1 kinks may be denoted by $s_i$, $i \in [2, N]$, and $s_1 = s_a$ and $s_{N+1} = s_b$. For $\vec{r}$ on a chord-line, the object function $f(\vec{r})$ may be reconstructed exactly as:

$$f(\vec{r}) = \int_{R^3} d\vec{r}' K(\vec{r}, \vec{r}') g(\vec{r}') \quad (23)$$

where the integral kernel $K(\vec{r}, \vec{r}')$ in the above equation may be represented by:

$$K(\vec{r}, \vec{r}') = \frac{1}{2\pi j} \int_{R^3} d\vec{v} \, sgn[\vec{v} \cdot \hat{e}_c] e^{2\pi j \vec{v} \cdot (\vec{r} - \vec{r}')} \quad (24)$$

the generalized backprojection $g(\vec{r}')$ may be expressed as:

$$g(\vec{r}') = \int_{s_a}^{s_b} \frac{ds}{|\vec{r}' - \vec{r}_0(s)|} \frac{\partial}{\partial q} \overline{D}(\vec{r}_0(q), \hat{\beta}) \bigg|_{q=s} \quad (25)$$

$$= \sum_{i=1}^{N} \int_{s_i}^{s_{i+1}} \frac{ds}{|\vec{r}' - \vec{r}_0(s)|} \frac{\partial}{\partial q} \overline{D}(\vec{r}_0(q), \hat{\beta}) \bigg|_{q=s}$$

and the extended data function may be defined as:

$$\overline{D}(\vec{r}_0(s), \hat{\beta}) = D(\vec{r}_0(s), \hat{\beta}) - D(\vec{r}_0(s), -\hat{\beta}) \quad (26)$$

As discussed above, reconstruction of an image using chords may be achieved in a variety of manners. As shown below, exact reconstruction of the object function $f(\vec{r})$ may be performed based on filtered-backprojection (FBP), back-projection-filtration (BPF), and Minimum Filtration Back-projection (MFBP). Other methodologies may also be used to reconstruct the image based on chords.

The explicit form of a reconstruction algorithm may depend generally upon the selection of the coordinate systems. For each point s on the trajectory, let $\{u, v, w\}$ denote the rotation-coordinate system. It is assumed that its origin is at $\vec{r}_0(s)$ and that its unit vectors are given by:

$$\hat{e}_u(s) = (-\sin(s), \cos(s), 0), \hat{e}_v(s) = (0, 0, 1), \hat{e}_w(s) = (\cos(s), \sin(s), 0) \quad (27)$$

Let (x, y, z) and (u, v, w) denote the coordinates of a point within the support cylinder in the fixed- and rotation-coordinate systems, respectively, which can be shown to satisfy:

$$x = -u \sin(s) + w \cos(s) + x_0(s)$$

$$y = u \cos(s) + w \sin(s) + y_0(s)$$

$$z = v + z_0(s) \quad (28)$$

It can be seen that the u-w plane and the y-axis of the rotation-coordinate system are parallel to the x-y plane and to the z-axis, respectively, of the fixed-coordinate system.

One may use a two-dimensional (2D) detector that has a normal vector $\hat{e}_w(s)$ and is at a distance $S(s) > 0$ from a point $\hat{r}_0(s)$ on the trajectory. On the detector plane, $\{u_d, v_d\}$ may be used to denote the cone-beam projection of the 2D coordinate system $\{u, v\}$. Therefore, the $u_d$- and $v_d$-axis are along $\hat{e}_u(s)$ and $\hat{e}_v(s)$, respectively, and the origin of the detector-coordinate system $\{u_d, v_d\}$ is at the projection of $\vec{r}_0(s)$ onto the detector plane. Any point on the detector plane can now be specified completely in terms of $(u_d, v_d)$. It can readily be shown that:

$$u = -\frac{w}{S(s)} u_d \text{ and } v = -\frac{w}{S(s)} v_d \quad (29)$$

In the context of CT scanning, because an individual x-ray within the cone-beam from a source point at $\vec{r}_0(s)$ can be specified completely by the detector coordinates $u_d$ and $v_d$, we can also use P $(u_d, v_d, s)$ to denote the data $D(\vec{r}_0(s), \hat{\beta})$:

$$P(u_d, v_d, s) = D(\vec{r}_0(s), \hat{\beta}) \text{ and } \frac{\partial}{\partial q} D(\vec{r}_0(q), \hat{\beta}) \bigg|_{q=s} \quad (30)$$

$$= \frac{dP(u_d, v_d, s)}{ds} \bigg|_{\hat{\beta}}$$

where $\hat{\beta}$ also satisfies:

$$\hat{\beta} = \frac{1}{A(u_d, v_d)} [u_d \hat{e}_u(s) + v_d \hat{e}_v(s) - S(s) \hat{e}_w(s)] \quad (31)$$

$$A(u_d, v_d) = \sqrt{u_d^2 + v_d^2 + S^2(s)} \quad (32)$$

One existing methodology for reconstructing images is called filtered-backprojection (FBP). FBP-based methodologies reconstruct images by performing a shift-invariant filtering of the modified data followed by a weighted backprojection of the filtered data. The following reconstructs the image on a chord using the FBP methodology by exploiting data on the cone-beam projection of the chord-line onto the detector plane.

Under conditions (1) and (2) discussed above, Equation (23), in combination with Equations (24)-(26), yields an exact image function on an entire chord-line, and thus on the chord as well. The following provides an exact expression of the image $f(\vec{r})$, $$f_R(\vec{r}) = \int_{R^3} d\vec{v} \, sgn[\vec{v} \cdot \hat{e}_c]$$

$$\sum_{i=1}^{N} \int_{s_i}^{s_{i+1}} ds \left[ \vec{v} \cdot \frac{d\vec{r}_0(s)}{ds} \right] F(\vec{v}) e^{2\pi j \vec{v} \cdot \vec{r}_0(s)} \delta(\vec{v} \cdot \vec{r} - \vec{v} \cdot \vec{r}_0(s)).$$

in which the δ-function implies the condition $\vec{v} \cdot (\vec{r} - \vec{r}_0(s)) = 0$, where $\vec{r}$ is on the chord-line. Further, $\hat{e}'_c$ may be defined as:

$$\hat{e}'_c = \frac{1}{\alpha}[\hat{e}_c \times (\vec{r} - \vec{r}_0(s))] \times \hat{e}_w \text{ and } \vec{v}_d = \hat{e}_w \times [\vec{v} \times \hat{e}_w] \quad (34)$$

where $\alpha = |[\hat{e}_c \times (\vec{r} - \vec{r}_0(s))] \times \hat{e}_w|$ is the normalization factor. Unit vector $\hat{e}'_c$ indicates the direction of the cone-beam projection of the chord-line onto the detector plane.

For $\vec{r}$ on the chord-line, one can readily conclude that $\hat{e}_w \cdot (\vec{r} - \vec{r}_0(s)) < 0$. Using this result and $\vec{v} \cdot (\vec{r} - \vec{r}_0(s)) = 0$, it may be shown that:

$$\text{sgn}[\vec{v} \cdot \hat{e}_c] = \text{sgn}[\vec{v}_d \cdot \hat{e}'_c] = \text{sgn}[v'_c] \quad (35)$$

where $v'_c = \vec{v}_d \cdot \hat{e}'_c$. Therefore, a portion of Equation (24) may be rewritten as:

$$K(\vec{r}, \vec{r}') = \frac{1}{2\pi j} \frac{S^2(s)}{w^2} \int_R dv'_c \text{sgn}[v'_c] e^{2\pi j(u_c - u'_c)v'_c} \delta(u_\perp - u'_\perp) \delta(w - w') \quad (36)$$

where $u_c$ and $u'_c$ denote the coordinates on the conebeam projection of the chord-line onto the detector plane, and the $u\perp$-axis is perpendicular to the $u_c$-axis. For $\vec{r}$ on the chord-line, $u\perp = 0$. Therefore, one can express this portion of the equation as:

$$K(\vec{r}, \vec{r}') = \frac{1}{2\pi^2} \frac{S^2(s)}{w^2} \frac{1}{(u_c - u'_c)} \delta(u'_\perp) \delta(w - w') \quad (37)$$

Because of the δ(w−w') function in Equation (37), only the first term (i.e., the physical data $D(\vec{r}_0(s), \hat{\beta})$) of the extended data function in Equation (26) contributes to the backprojection image $g_c(x_c, s_a, s_b)$. Therefore, the derivation below considers the contribution only from the physical data term $D(\vec{r}_0(s), \hat{\beta})$.

Since $$d\vec{r}' = \frac{w'^2}{S^2(a)} du'_c du'_\perp dw',$$

substituting Equations (26) and (37) into Equation (23), and changing the orders of the integrations over $u'_c$ and s, one obtains:

$$f(x_c, s_a, s_b) = \frac{1}{2\pi^2} \int_{s_a}^{s_b} ds \int_R \frac{du'_c}{u_c - u'_c} \frac{1}{|\vec{r}' - \vec{r}_0(s)|^2} \frac{dP(u'_d, v'_d, s)}{ds}\bigg|_{\hat{\beta}} \quad (38)$$

Equation (38) is referred to as the filtered backprojection (FBP) algorithm because it performs a 1D Hilbert transform (i.e., the integration over u'C) before backprojecting the filtered data (i.e., the integration over s) onto the chord. Non-truncated data are necessary when the FBP algorithm is used for reconstructing the image on a chord because the filtration in the FBP algorithm requires knowledge of data over $u'_c \in R$.

Reconstructing an Image Based on Back-Projection Filtration

Another methodology for reconstructing images is the backprojection-filtration (BPF) methodology. Unlike the existing FBP-based methodology, the BPF methodology reconstructs an image within an ROI by first backprojecting the data (such as weighted data) and then performing filtering (such as shift-invariant filtering) of the backprojection. Generally speaking, backprojection involves transforming measured data from data space into image space. When backprojecting, the data may further be modified. For example, the data may be weighted or the derivative of the data may be taken. However, modifying the data when backprojecting is not necessarily required.

When backprojecting, the measured data may first be selected, and then transformed from data space into image space. With backprojecting using chords, one may select the data on the projection of the segment of the chord in the ROI onto the detector. Referring to FIG. 2a as an example, if the segment of the chord (shown as line 208) in the ROI for reconstruction is the flat line at the bottom of portion 204 (shown as line 210), the projection of that segment onto the detector is the data from point "C" to point "D." These data in the range from "C" to "D" may be backprojected onto the segment of the chord. Alternatively, if the segment of the chord is longer than segment 208 (such as a segment which includes 208 and additional segments 212, the projection of this segment onto the detector is the data from point "E" to point "F." These data in the range from "E" to "F" may be backprojected onto the segment of the chord. Thus, data corresponding to any segment of the chord, or the entire chord, may be backprojected onto the segment. The backprojection may be performed for all of the views onto that specific segment. After backprojection, filtration may be performed on the backprojections onto the specific segment. The segments used to reconstruct the ROI using the BPF methodology may comprise support segments. Depending on the type of image sought to be reconstructed, various filtration methodologies may be used. For example, if a substantially exact reconstruction is sought, one example of a filtration methodology is using a Hilbert transform. As another example, if a substantially exact reconstruction is not sought, other filtration methodologies may be used.

A variety of data acquisition methodologies may be used to generate data for the BPF methodology. The BPF methodology may exactly reconstruct an image within a given ROI directly from reduced-scan data that contain truncations or from data that does not contain truncations. For example, the data acquisition methodology discussed above wherein at least one characteristic of the source is modified (such as the illumination coverage of the source) may be used to generate data for the BPF methodology.

The following is an example using the BPF methodology in the context of reconstructing an image based on chords. However, the BPF methodology is not limited to reconstructing an image using chords, and may reconstruct images generally. For example, the BPF methodology may be used in traditional reconstruction outside of the chord context.

For a given chord specified by $s_a$ and $s_b$ (points on the source trajectory), a coordinate system $\{x_c, y_c, z_c\}$ is considered that has its origin at the middle point of the chord. In this system, the $x_c$-axis coincides with the chord-line and has a unit vector $\hat{e}_c$, whereas the $y_c$- and $z_c$-axis are perpendicular to the $x_c$-axis. Therefore, any point on the chord-line specified by $s_a$ and $s_b$ can be denoted as $(x_c, s_a, s_b)$, and $f_c(x_c, s_a, s_b)$ and $g_c(x_c, s_a, s_b)$ may be used to denote the image function and the backprojection on the chord-line, which satisfy:

$$f(\vec{r}) = f_c(x_c, s_a, s_b) \text{ and } g_c(\vec{r}) = g_c(x_c, s_a, s_b) \quad (39)$$

where $\vec{r}$ and $x_c$ are related through Equation (6). In terms of $P(u_d, v_d s)$, the backprojection image on a chord specified by $s_a$ and $s_b$ is:

$$g_c(x_c, s_a, s_b) = \int_{s_a}^{s_b} \frac{sgn(-\hat{\beta} \cdot \hat{e}_w) ds}{|\vec{r}(x_c) - \vec{r}_0(s)|} \frac{\partial}{\partial s} P(u_d, v_d, s) \bigg|_{\hat{\beta}} \quad (40)$$

The signum factor in the integral derives from the extension of the data function in Equation (26). For $\vec{r}$ on the chord-line, the kernel $K(\vec{r}, \vec{r}')$ in Equation (24) may be rewritten as:

$$K(\vec{r}, \vec{r}') = \frac{1}{2\pi j} \int_R d\nu_c sgn[\nu_c] e^{2\pi j \nu_c (x_c - x'_c)} \delta(y'_c) \delta(z'_c) \quad (41)$$

$$= \frac{1}{2\pi^2 (x_c - x'_c)} \delta(y'_c) \delta(z'_c)$$

where $\vec{r}' \in R^3$, and $\nu_c$ denotes the spatial frequency with respect to $x_c$. Applying Equation (34) to Equation (23) yields:

$$f_c(x_c, s_a, s_b) = \frac{1}{2\pi^2} \int_R \frac{dx'_c}{x_c - x'_c} g_c(x'_c, s_a, s_b) \quad (42)$$

where $x_c \in R$. Therefore, the image $f_c(x_c, s_a, s_b)$ on the chord-line is the Hilbert transform, along the chord-line, of the backprojection image $g_c(x'_c, s_a, s_b)$. The result in Equation (42) provides a methodology for reconstructing the image on a chord from knowledge of the backprojection image over the entire chord-line. As discussed in more detail below, by exploiting the condition that the image support is confined on the chord, it is shown that the image on the chord can be reconstructed from knowledge of the backprojection image only on the chord.

Figure 16:
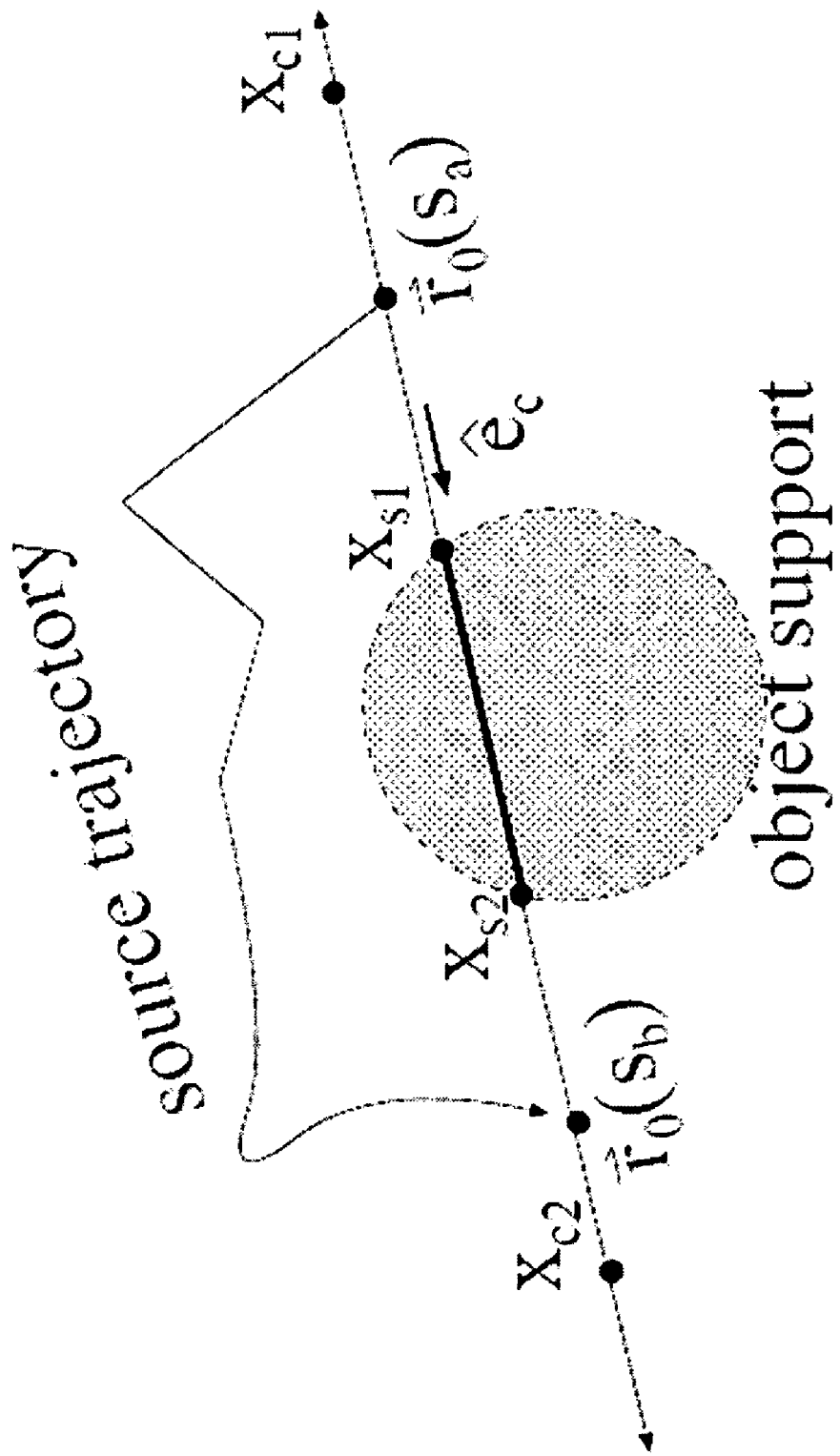
FIG. 16 illustrates an object support and source trajectory, illustrating the support segment ($x_c \in [x_{s1}, x_{s2}]$) and backprojection segment ($x_c \in [x_{c1}, x_{c2}]$).

$x_{s1}$ and $x_{s2}$ are denoted as the endpoints of the intersection of the chord with the support cylinder, and referred to as the support segment on the chord. Without loss of generality, it is assumed that $x_{s1} \leq x_{s2}$. Considering condition (1) on the trajectory, $[x_{s1}, x_{s2}] \in [-1, 1]$, i.e., the support segment is always within the chord as shown in FIG. 16. Specifically, FIG. 16 depicts an object support and source trajectory, illustrating the support segment ($x_c \in [x_{s1}, x_{s2}]$) and backprojection segment ($x_c \in [x_{c1}, x_{c2}]$). Performing the Hilbert transform with respect to $x_c$ on both sides of Equation (42), results in:

$$g_c(x_c, s_a, s_b) = 2 \int_R \frac{dx'_c}{x'_c - x_c} f_c(x'_c, s_a, s_b) \quad (43)$$

$$= 2 \int_{x_{c1}}^{x_{c2}} \frac{dx'_c}{x'_c - x_c} f_c(x'_c, s_a, s_b),$$

where $x_c \in R$, and parameters $x_{c1}$ and $x_{c2}$ satisfy $x_{c1} \in (-\infty, x_{s1}]$ and $x_{c2} \in [s_{s2}, \infty)$, respectively. $[x_{c1}, c_{c2}]$ is referred to as the backprojection segment. The last part of Equation (43) is determined by observing that $f_c(x_c, s_a, s_b) = 0$ for $x_c \in [x_{s1}, x_{s2}]$.

The result in Equation (43) represents a Hilbert transform on a finite interval, and its inversion can be obtained as:

$$f_c(x_c, s_a, s_b) = \frac{1}{2\pi^2} \frac{1}{\sqrt{(x_{c2} - x_c)(x_c - x_{c1})}} \times \left[ \int_{x_{c1}}^{x_{c2}} \frac{dx'_c}{x'_c - x_c} \right. \quad (44)$$

$$\left. \sqrt{(x_{c2} - x'_c)(x'_c - x_{c1})} g_c(x'_c, s_a, s_b) + C \right],$$

where $x_c \in [x_{s1}, x_{s2}]$, the relationship between $x_c$ and $\vec{r}$ is determined by Equation (6), and the constant C is given by:

$$C = 2\pi \int_{x_{c1}}^{x_{c2}} f_c(x_c, s_a, s_b) dx_c = 2\pi D(\vec{r}_0(s_a), \hat{e}_c) \quad (45)$$

Because the second term in Equation (44) is only a constant that can readily be obtained directly from data, the computation load required for reconstructing the image on a chord is determined by the compilation load required by the first term in Equation (44).

By modifying the form of the first term, Equation (44) may be rewritten as:

$$f_c(x_c, s_a, s_b) = \frac{1}{2\pi} \frac{1}{\sqrt{(x_{c2} - x_c)(x_c - x_{c1})}} \left[ \int_R \frac{dx'_c}{x_c - x'_c} g_\pi(x'_c, s_a, s_b) + \right. \quad (46)$$

$$\left. 2\pi D(\vec{r}_0(s_a), \hat{e}_c) \right]$$

where $$g_\pi(x'_c, s_a, s_b) = \prod_c (x'_c) \sqrt{(x_{c2} - x'_c)(x'_c - x_{c1})} g_c(x'_c, s_a, s_b) \quad (47)$$

and $\Pi_c(x'_c) = 1$ if $x'_c \in [x_{c1}, x_{c2}]$ and 0 if $x'_c \in [x_{c1}, x_{c2}]$. Unlike the first term (i.e., the Hilbert transform over a finite interval) in Equation (44) that does not appear to represent explicitly a shift-invariant filtration on the $x'_c$-axis, Equation (46) indicates explicitly a shift-invariant filtering (i.e., the Hilbert transform) over the entire $x'_c$-axis. Such a change may have practical significance in terms of performing the calculations because the Hilbert transform may now be calculated efficiently by use of the fast-Fourier-transform (FFT) technique.

Analyzing Equation (47), it is observed that the image on the chord may be obtained exactly from knowledge of the backprojection image on a support segment, specified by $x_c \in [x_{s1}, x_{s2}]$, on the chord. This provides the basis for exact image reconstruction on a chord possibly from projections containing transverse truncation. Equation (47) is referred to as the backprojection-filtration (BPF) algorithm because it backprojects the modified data (i.e., the integration over s in obtaining $g_c(x'_c, s_a, s_b)$) before performing the 1D Hilbert transform of the weighted backprojection image (i.e., the integration over $x'_c$).

Generating an Image Based on Minimum Filtration Backprojection

Still another methodology for reconstructing images is the minimum filtration backprojection (MFBP) methodology. The MFBP methodology differs fundamentally from existing FBP methodologies because, like the BPF methodology, the MFBP methodology admits reconstruction from minimum data. Specifically, the MFBP methodology may exactly reconstruct an image within a given ROI directly from reduced-scan data that contain truncations. The data acquisition methodology discussed above wherein at least one characteristic of the source is modified (such as the illumination coverage of the source) may be used to generate data for the MFBP methodology. The MFBP methodology may also exactly reconstruct an image from data that does not contain truncations.

When using the MFBP methodology with chords, filtration may be performed on data based on a projection of the segment or chord onto the detector. Any segment of the chord, or the entire chord, may be used. Using the example shown in FIG. 2a, the projection of segment 210 corresponds to the data from point "C" to point "D" on the detector. Filtration may be performed on this data. Then, the filtered data may be backprojected onto the segment 210. As discussed above, the type of filtration may depend on the image sought, such as a Hilbert transform if a substantially exact image is sought, or other methodologies if a substantially exact image is not sought. Similarly, segments other than segment 210 may be used. For example, a segment which includes segment 210 and additional segments 212 may be used. The segments used to reconstruct the ROI using the MFBP methodology may comprise support segments.

The following is an example using the MFBP methodology in the context of reconstructing an image based on chords. However, the MFBP methodology is not limited to reconstructing an image using chords, and may reconstruct images generally. For example, the MFBP methodology may be used in traditional reconstruction outside of the chord context.

The BPF methodology described in the above example reconstructs the image on a chord by performing a 1D filtration of the backprojection along the chord-line. It is also possible to reconstruct the image on a chord by performing the ID-data-filtration on the detector prior to their backprojection onto the chord. The MFBP algorithm described below may reconstruct images on chords for any general trajectory. Therefore, the below MFBP methodology may be applied to any of the exemplary trajectories discussed herein.

Using Equations (26), (30), and (47) in Equation (46) and changing the order of the integrations over $x'_c$ and s, we obtain $$f_c(x_c, s_a, s_b) = \frac{1}{2\pi^2} \frac{1}{\sqrt{(x_{c2}-x_c)(x_c-x_{c1})}} \times \left[ \int_{s_a}^{s_b} ds \int_R \frac{dx'_c}{x_c - x'_c} \right. \tag{48}$$

$$\left. \frac{\sqrt{(x_{c2}-x'_c)(x'_c-x_{c1})}}{|\vec{r}'-\vec{r}_0(s)|} sgn[-\hat{\beta} \cdot \hat{e}_w] \frac{dP(u'_d, v'_d, s)}{ds} \bigg|_{\hat{\beta}} + C \right],$$

where $\vec{r}$ and $x_c$ are related through Equation (6); the relationship between $\vec{r}'$ and $x'_c$ can be obtained from Equation (6) by simply replacing $\vec{r}$ and $x_c$ with $\vec{r}'$ and $x'_c$, respectively; and C is given by Equation (45).

For a given $s \in [s_a, s_b]$, letting $u_c$ denote the cone-beam projection of $x_c \in [c_{c1}, x_{c2}]$ onto the detector, it can then be shown that:

$$u_c = \frac{w_2(x_c - x_{c1})}{w_1(x_{c2} - x_c) + w_2(x_c - x_{c1})} \tag{49}$$

where $w_1 = -[\vec{r}_0(s_a) - \vec{r}_0(s_a)] \cdot \hat{e}_w$, and $w_2 = -[\vec{r}_0(s_b) - \vec{r}_0(s)] \cdot \hat{e}_w$. In particular, $u_{c1}$ and $u_{c2}$ is used to denote the values of $u_c$ that are obtained when using $x_c = x_{c1}$ and $x_{c2}$ in Equation (49), respectively. Replacing $x_c$ by $u_c$ in Equation (48) yields:

$$f_c(x_c, s_a, s_b) = \tag{50}$$

$$\int_{s_a}^{s_b} ds [w_2(x_{c2} - u_c) + w_1(u_c - x_{c1})] \left[ \int_R \frac{du'_c}{u_c - u'_c} P_\pi(u'_c, s_a, s_b) + C \right]$$

where, for a given $u'_c$, one determines $x'_c$ by use of Equation (49), $\vec{r}$ and $x'_c$ are related through Equation (30), $x'_c$ and $u'_c$ are related through Equation (49), and $$(u'_d, v'_d, -S(s)) = \vec{r}_0(s) - (\vec{r}' - \vec{r}_0(s)) \frac{S(s)}{(\vec{r}' - \vec{r}_0(s)) \cdot \hat{e}_w} \tag{51}$$

$$P_\pi(u'_c, s_a, s_b) =$$

$$\frac{\sqrt{(x_{c2} - x'_c)(x'_c - x_{c1})}}{w_2(x_{c2} - u'_c) + w_1(u'_c - x_{c1})} \frac{\Pi_c(x'_c)}{|\vec{r}' - \vec{r}_0(s)|} sgn[-\hat{\beta} \cdot \hat{e}_w] \frac{dP(u'_d, v'_d, s)}{ds} \bigg|_{\hat{\beta}}$$

It can be seen that the first term in Equation (50) represents a Hilbert transform over the $u'_c$-axis, thus allowing an efficient computation of the data filtering in Equation (50) by use of the FFT technique. Therefore, the algorithm expressed in Equation (50) may reconstruct the image on a chord by performing a filtering of the weighted data (i.e., the 1D Hilbert transform) over $u'_c$-axis on the detector followed by the backprojection of the filtered data (i.e., the integration over s) onto the chord. Because this new methodology was derived from the BPF methodology, it may also exactly reconstruct the image on a chord from truncated data, similar to the BPF methodology. This is unlike the FBP methodology which cannot reconstruct exactly the image on a chord from truncated data.

Numerical Studies Applying BPF, MFBP, and FBP

Figure 17A:
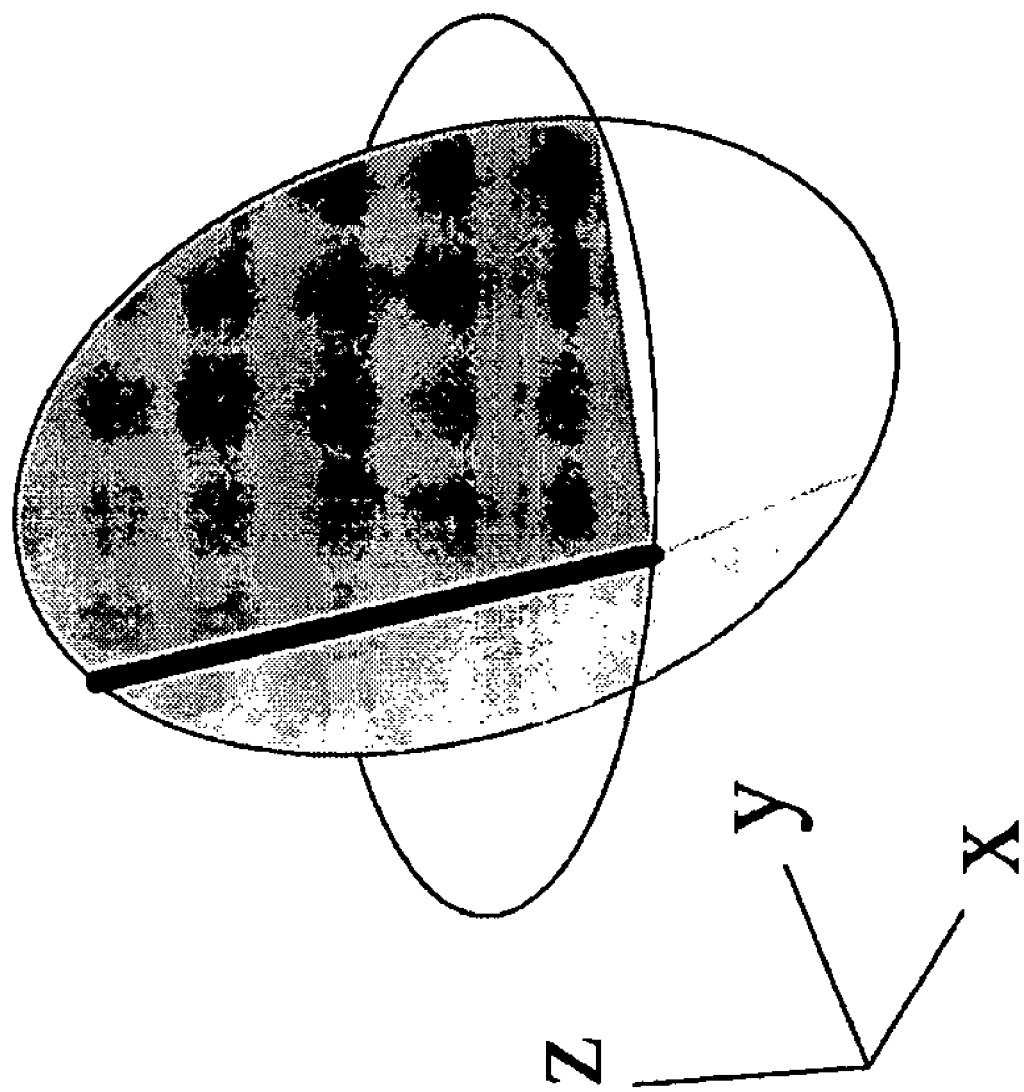
FIG. 17a illustrates the two-circle trajectory with the surface being generated by fixing $s_a=0.04 \, \pi p_{cc}$ and by sweeping $s_b$ through the interval $[0,3 \, \pi p_{cc}/2]$.

Quantitative results of the numerical studies are presented for demonstrating the theory and methodologies developed above. First, image reconstruction is performed on individual chords from data acquired with a two-circle trajectory, as shown in FIGS. 8c and 17a. Subsequently, image reconstruction is conducted within a 3D region of interest (ROI) from n-PI data acquired with a helical trajectory.

The three methodologies described above, FBP in Equation (38), BPF in Equation (46), MFBP in Eq. (50), involve determining the data derivative:

$$\frac{\partial}{\partial q} D(\vec{r}_0(q), \hat{\beta}) \bigg|_{q=s} \tag{53}$$

or equivalently:

$$\frac{dP(u_d, v_d, s)}{ds} \bigg|_{\hat{\beta}} \tag{54}$$

For a helical scan, the direct computation of the data derivative with respect to λ (or, equivalently, s) may be susceptible to aliasing artifacts due to the relatively sparse angular sampling. Instead, an alternative expression for computation of the data derivative may be derived:

$$\frac{\partial}{\partial q}D(\vec{r}_0(q), \hat{\beta})\bigg|_{q=s} = \frac{dP(u_d, v_d, s)}{ds}\bigg|_{\hat{\beta}}$$

$$= \left[\frac{d\vec{r}_0(s)}{ds} \cdot \hat{e}_u(s) + \frac{u_d}{S(s)}\frac{d\vec{r}_0(s)}{ds} \cdot \hat{e}_w(s)\right]$$

$$\frac{A(u_d, v_d)}{\vec{r}' - \vec{r}_0(s)}\frac{\partial P(u_d, v_d, s)}{\partial u_d} +$$

$$\left[\frac{d\vec{r}_0(s)}{ds} \cdot \hat{e}_v(s) + \frac{v_d}{S(s)}\frac{d\vec{r}_0(s)}{ds} \cdot \hat{e}_w(s)\right]$$

$$\frac{A(u_d, v_d)}{\vec{r}' - \vec{r}_0(s)}\frac{\partial P(u_d, v_d, s)}{\partial u_d} +$$

$$\frac{dP(u_d, v_d, s)}{ds}\bigg|_{\vec{r}},$$

where $A(u_d, v_d)$ is defined in Equation (32). In practical cone-beam imaging, data are measured generally on discrete grids uniformly distributed on axes $u_d$ and $v_d$. Therefore, using the expression in Equation (55), data derivatives with respect to $u_d$ and $v_d$ may be computed directly from the measured data without invoking additional interpolation, whereas the data derivative in the last term of Equation (55) may be computed analytically through the integration over s in the backprojection step, yielding the boundary terms at $s_a$ and $s_b$, respectively.

In the present numerical study, the scanning of the Shepp-Logan phantom is considered by use of two trajectories. The central point of the largest ellipsoid of the Shepp-Logan phantom is assumed to be on the origin of the fixed-coordinate system. For scan one, the two-circles trajectory described with respect to FIG. 6c is employed in which the two circles are perpendicular to each other ($\alpha=\pi/2$) and the trajectory segment is $s \in [-p_{cc}\pi/2, 3 p_{cc}\pi/2]$. For scan two, the standard helical trajectory is used and images are reconstructed on chords that correspond to the so-called 3-PI lines; namely, $s_a \in [-2\pi R_0, 0]$ and $s_b \in [s_a+2\pi R_l, s_a+4\pi R_l]$ and $R_l^2 = R_0^2 + (h/2\pi)^2$. Condition (2) is satisfied by the two trajectories considered. From the Shepp-Logan phantom, the two trajectories are used to generate two sets of cone-beam data. For the two-circles trajectory, the arc length interval of $2\pi p_{cc}$ is divided into 1024 points, where $p_{cc}$ is taken to be 570 mm. The spacing along the helical trajectory is $2\pi R_l/1200$, where $R_0$ is 570 mm and the pitch h is 40 mm per turn. The source-detector distance is taken to be constant at S=1005 mm. A 2D detector plane is used consisting of 512×256 square detector-elements. The short side of the rectangle detector plane is along the z-axis, and the size of square detector element is 0.78 mm by 0.78 mm.

Figures 17B, 17C:
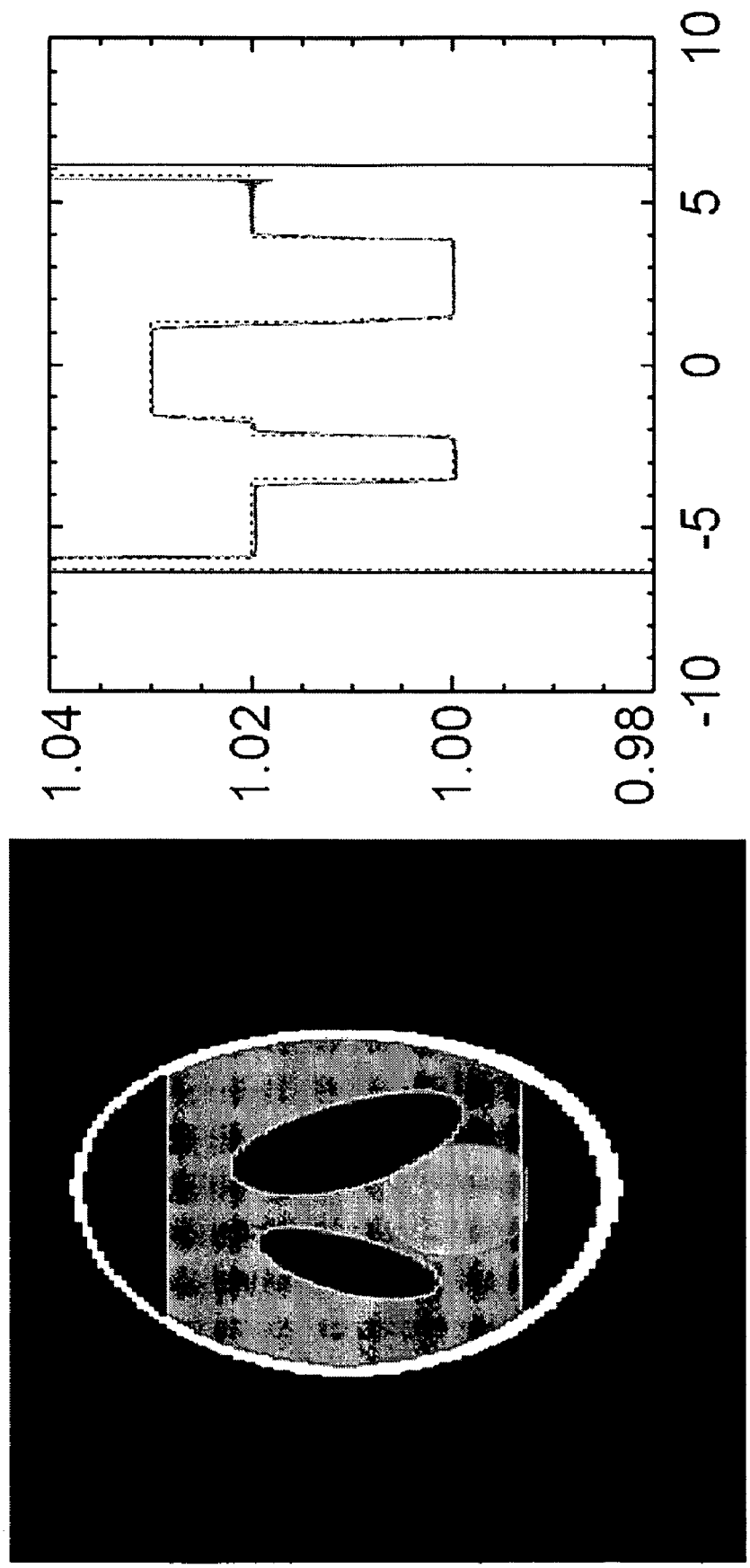

To demonstrate the flexibility of the chord reconstruction methodology, the two-circle source trajectory is used. For this example, only the results obtained by employing the BPF methodology are shown. Similar results may also be obtained by use of the MFBP and FBP methodologies. FIG. 17a shows the two-circle trajectory with the surface being generated by fixing $s_a=0.04$ $\pi p_{cc}$ and by sweeping $s_b$ through the interval $[0, 3 \pi p_{cc}/2]$. The thick line segment in FIG. 17a depicts the chord specified by $s_a=-0.04$ $\pi p_{cc}$ and $s_b=0.98$ $\pi p_{cc}$. FIG. 17b is the reconstruction image of the Shepp-Logan phantom on chords comprising the surface shown in FIG. 17a. Quantitative agreement is shown in FIG. 17c. Specifically, FIG. 17c shows a profile of the reconstructed (solid line) and true (dashed line) images of the chord indicated in FIG. 17a, comparing the reconstructed image with the corresponding true image on a chord and demonstrating the accuracy of the proposed algorithms for image reconstruction on chords.

An ROI within any three dimensional object, such as a support cylinder, may be decomposed into a family of straight line segments. When these line segments are on chords of a trajectory satisfying conditions (1) and (2), the reconstruction methodologies may be used for exactly reconstructing images on the chords and, consequently, for reconstructing an exact image within the ROI. For the conventional helical trajectory, chords are the n-PI-line segments specified by $(n-1) \pi R_l \leq s_b - s_a \leq (n+1) \pi R_l$, where n is an odd integer. In particular, for n=1, the chords become the PI-line segments.

As an example, the image reconstruction within an ROI is illustrated below using the BPF and MFBP methodologies from 3-PI data acquired with a conventional helical trajectory. To simulate the 3-PI reconstruction problem, the cone-beam data were sampled at 2400 views along the source trajectory within two turns. Noisy data is also generated by adding Gaussian noise to the noiseless data. The standard deviation of the Gaussian noise is chosen to be 0.1% of the maximum value of the noiseless data so that the very low contrast structures within the Shepp-Logan phantom are not completely overwhelmed by data noise.

Figure 18A:
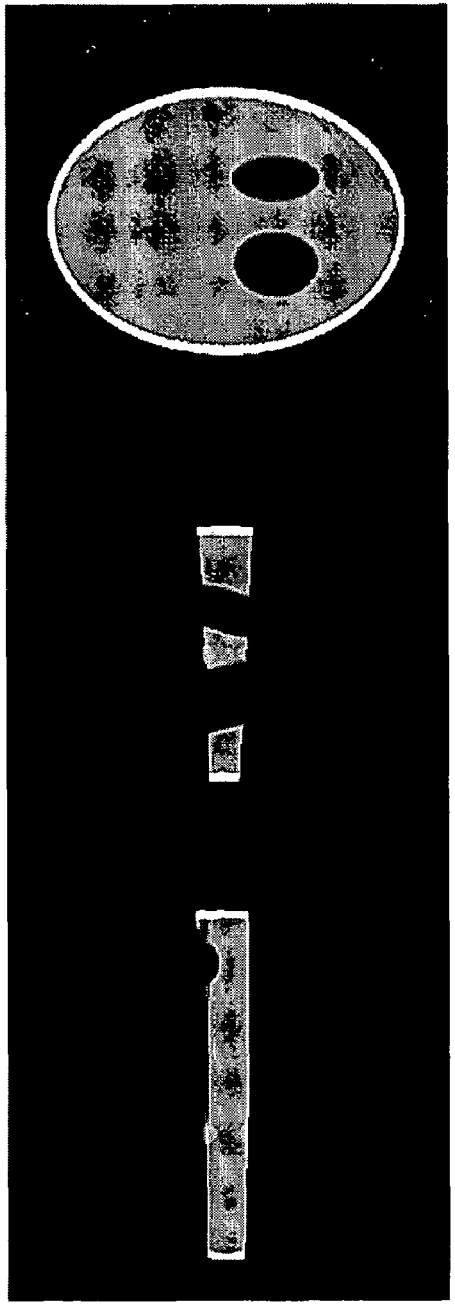
FIGS. 18a-b illustrate images of the Shepp-Logan phantom reconstructed using a backprojection-filtration methodology from the generated noiseless (in FIG. 18a) and noisy (in FIG. 18b) 3-PI data using chords, respectively.
Figure 18B:
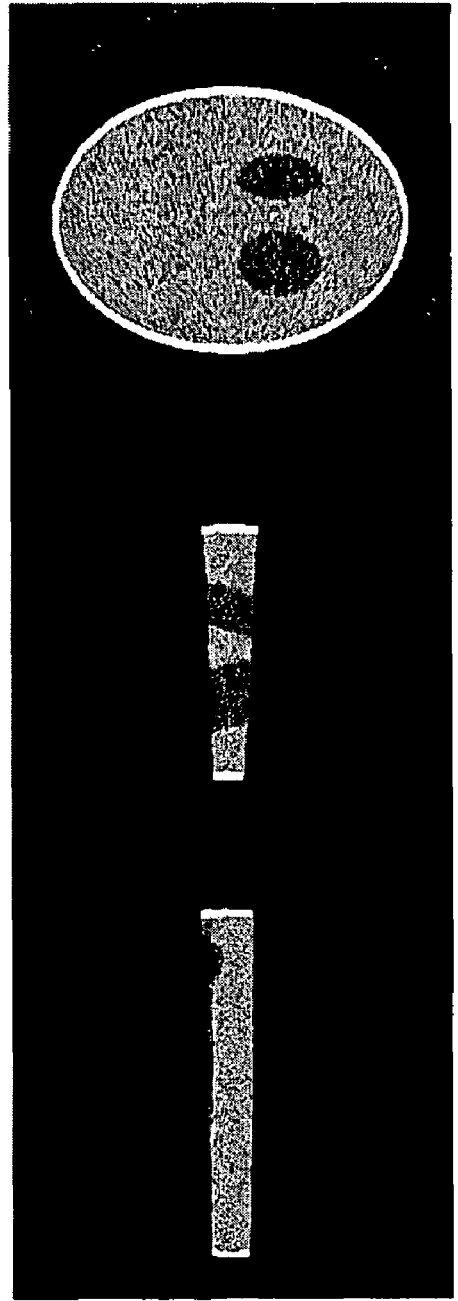

Referring to FIGS. 18a-b, there are shown images of the Shepp-Logan phantom reconstructed using the BPF methodology from the generated noiseless (in FIG. 18a) and noisy (in FIG. 18b) 3-PI data using chords, respectively. Images in the left, middle, and right columns in FIGS. 18a and 18b are on 2D slices specified by x=0 cm, y=-2.7 cm, and z=0 cm, respectively. The display window is [1.0,1.05]. Referring to FIGS. 19a-b, there are shown images of the Shepp-Logan phantom reconstructed using the MFBP methodology from the generated (in FIG. 19a) and noisy (in FIG. 19b) 3-PI data using chords, respectively. Images in the left, middle, and right columns in (a) and (b) are on 2D slices specified by x=0 cm, y=-2.7 cm, and z=0 cm, respectively. The display window is [1.0, 1.05]. Similar results, though not shown here, may also be obtained using the FBP methodology. These results indicate that the proposed algorithms can accurately reconstruct images on 3-PI-lines (i.e., chords).

Figure 20A:
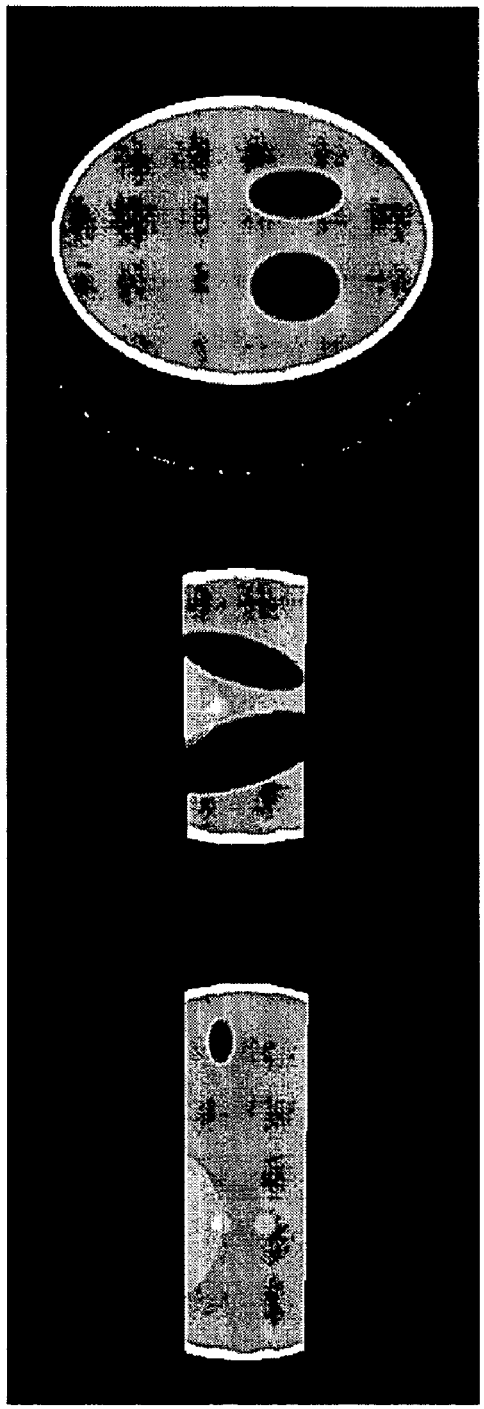
FIGS. 20a-b illustrate images of the Shepp-Logan phantom reconstructed using the backprojection-filtration methodology from the generated (in FIG. 20a) and noisy (in FIG. 20b) data on PI-line segments, respectively.
Figure 20B:
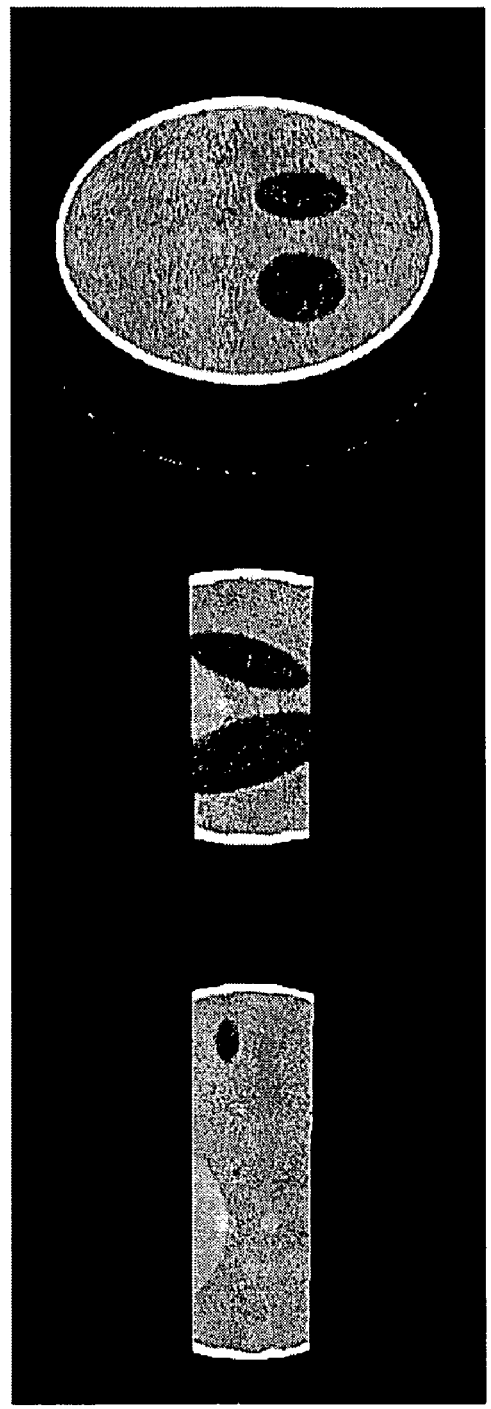
Figure 21B:
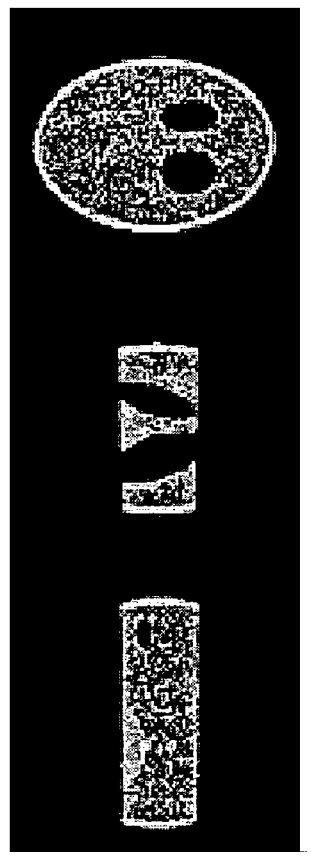
FIGS. 21a-b illustrate images of the Shepp-Logan phantom reconstructed using the minimum filtration backprojection methodology from the generated (in FIG. 21a) and noisy (in FIG. 21b) data on PI-line segments, respectively.
Figure 21A:
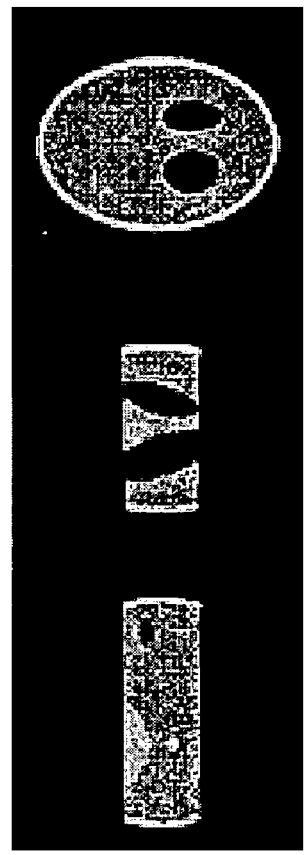

For comparison, the BPF and MFBP methodologies are also applied to reconstructing images on PI-line segments from the generated data over two turns, which are displayed in FIGS. 20a-b and 21a-b, respectively. Again, the images in FIGS. 20a and 21a and FIGS. 20b and 21b were obtained from the noiseless and noisy data, respectively. Images in the left, middle, and right columns in FIGS. 20a and 20b are on 2D slices specified by x=0 cm, y=-2.7 cm, and z=0 cm, respectively. The display window is [1.0,1.05]. Images in the left, middle, and right columns in FIGS. 21a and 21b are on 2D slices specified by x=0 cm, y=-2.7 cm, and z=0 cm, respectively. The display window is [1.0,1.05]. Reviewing the figures, it is apparent that the methodologies can accurately reconstruct images on PI-line segments (i.e., chords). For a fixed number of turns, it appears the 3D ROI is reconstructable based only upon the 3-PI-line segments is smaller than that reconstructable based upon the PI-line segments. This may be understood by recognizing that more 3-PI-line segments (i.e., more turns) than the PI-line segments are generally required to fill a given ROI.

PET Imaging

As discussed above, PET imaging is a diagnostic imaging procedure that may assess the level of metabolic activity and perfusion in various organ systems of an object, such as a human body. Some present PET imaging systems adopt a cylindrical configuration in which discrete detection elements are employed and arranged to form a stack of circular detector rings. Analytic PET reconstruction methods are also designed to work with this geometry. However, configurations other than a cylindrical configuration may be used.

PET systems based on detector panels have also been investigated and developed. For example, the PENN-PET systems consist of six hexagonally arranged flat, single-crystal NaI(Tl) detectors. In an exemplary C-PET scanner, these flat panels are replaced with curved NaI(Tl) plates. Other types of detectors may also be used. In addition, coincidence imaging by use of conventional gamma cameras have been considered. Detector panels may be used in small-animal and application-specific PET imagers. For example, dedicated PEM (positron emission mammography) systems and prostate imagers are often based on using two opposite flat or curved detector panels.

One advantage to using detector panels in a PET system is its cost-effectiveness. Large-area panels having high packing fraction can be built at a relatively low cost for obtaining PET systems with considerable axial extensions and hence increased detection sensitivity and imaging-volume coverage. The use of detector panels also allows for modular PET system designs, thereby offering flexible configurations that can be exploited for achieving optimal imaging under varying imaging conditions. Large-area detector panels may be used for providing high-performance imaging of objects, such as small-animal and application-specific PET imaging.

Image reconstruction for panel-based PET systems is accomplished by use of either iterative techniques or conventional analytic algorithms. Iterative techniques for 3D PET imaging are typically computationally extensive; on the other hand, analytic algorithms are generally more efficient. However, the conventional analytic algorithms are developed for working with cylindrical PET systems; therefore, it is necessary to interpolate the acquired data onto cylindrical coordinates before reconstruction for panel-based systems. This process can result in significant resolution loss in high-resolution imagers, such as in small-animal PET systems. Furthermore, the effectiveness and accuracy of existing analytical algorithms rely on the satisfaction of considerable restrictive imaging conditions. These conditions are often difficult to satisfy by panel-based PET systems. (For example, significant gaps may often exist between adjacent panels, resulting in missing data in the sinogram and leading to streak artifacts in images.)

Chord-based reconstruction may improve PET imaging. For example, for cone-beam reconstruction, the methodologies disclosed above allow for the use of general source trajectories and permit exact or substantially exact ROI reconstructions from reduced data. This ROI imaging capability may be useful for application-specific imaging in which small field of view scanners are used for acquiring data at various positions and views. Conversely, with these general reconstruction methods, one can study imaging configurations for producing images of certain prescribed ROIs while reducing radiation dose or avoiding exposure to critical organs.

The reconstruction methods discussed above, such as the x-ray cone-beam reconstruction techniques, may be extended to PET systems for producing an entirely new class of analytic reconstruction methods. Because the source trajectory may be any continuous path that is piecewise $C^1$ smooth, these techniques may be applied to work with the native data coordinates of PET systems, such as panel-based PET systems, without requiring interpolation of the data onto certain preferred coordinates. Therefore, one source of resolution loss in the conventional analytic PET reconstruction may be eliminated. In addition, because the methodologies allow for exact ROI reconstruction from reduced data that satisfy certain conditions, the reconstruction problems due to failed detection elements and detector gaps may be avoided for certain ROIs. The performance of these methods, such as image noise characteristics and spatial resolution, is discussed below.

Furthermore, the new techniques may be used to investigate the idea of modular design in which a PET system's configuration is flexible for yielding optimized performance under varying imaging conditions. For example, the reconstruction methodology may allow one to examine whether a given configuration can generate exact reconstructions for prescribed ROIs before reconstruction is performed. Given an imaging task, one can therefore develop suitable configurations for use and select among them those that can meet certain conditions, such as maximized sensitivity.

In PET, every pair of detection elements may define a line of response (LOR), which is conventionally defined as the line connecting the center of the front faces of the two detection elements. Assuming ideal spatial resolution, the expected coincidence counts measured by a PET scanner are equal to the line integrals of the activity distribution along the scanner's LORs. In comparison, the line integrals generated in x-ray cone-beam imaging are defined by the lines connecting the x-ray source to x-ray detectors. Therefore, every detection element in a PET system may be treated as the "source" or a virtual source in the cone-beam geometry, with the others as the detectors. By making this connection, which is discussed in more detail below, the reconstruction techniques discussed above may be readily extended to generate an entirely new class of analytic 3D PET reconstruction algorithms.

Figure 22B:
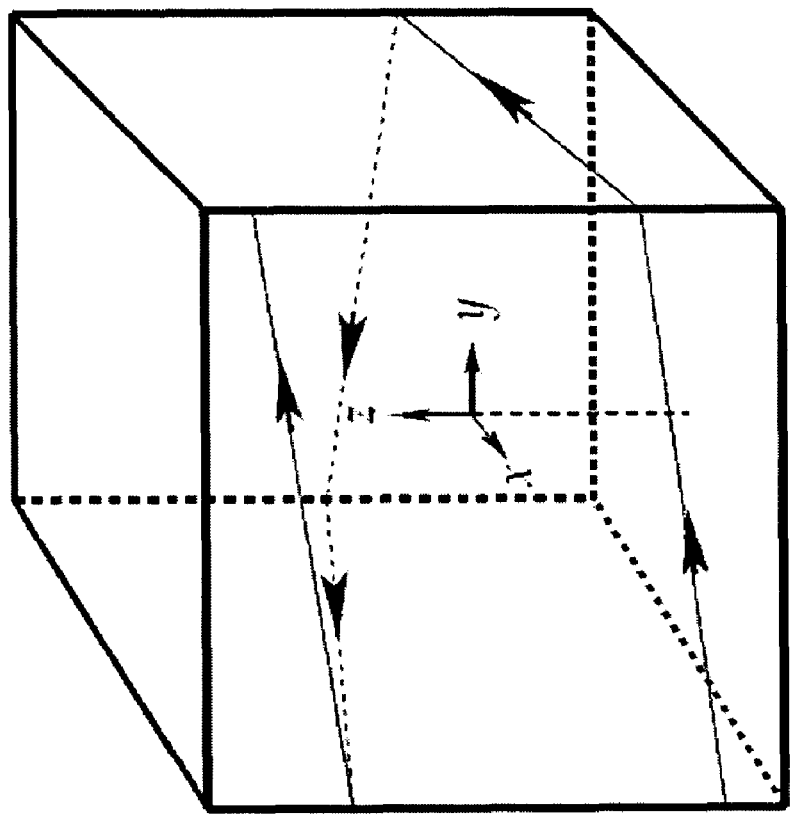
FIG. 22b illustrates a trajectory obtained by projecting a helical path onto the detector faces of a PET system.

As merely one example, the x-ray cone-beam reconstruction methods discussed above may be extended to work with any PET scanner configuration. As a specific example, however, a PET system that consists of four flat detector panels is considered, as shown in FIG. 22b. The LORs generated by this scanner configuration do not provide convenient sampling on the native coordinates assumed in analytic methods developed for reconstructing data generated by cylindrical PET systems. Although data can be rebinned, the process can be quite involved in order to avoid resolution degradation.

Figure 22A:
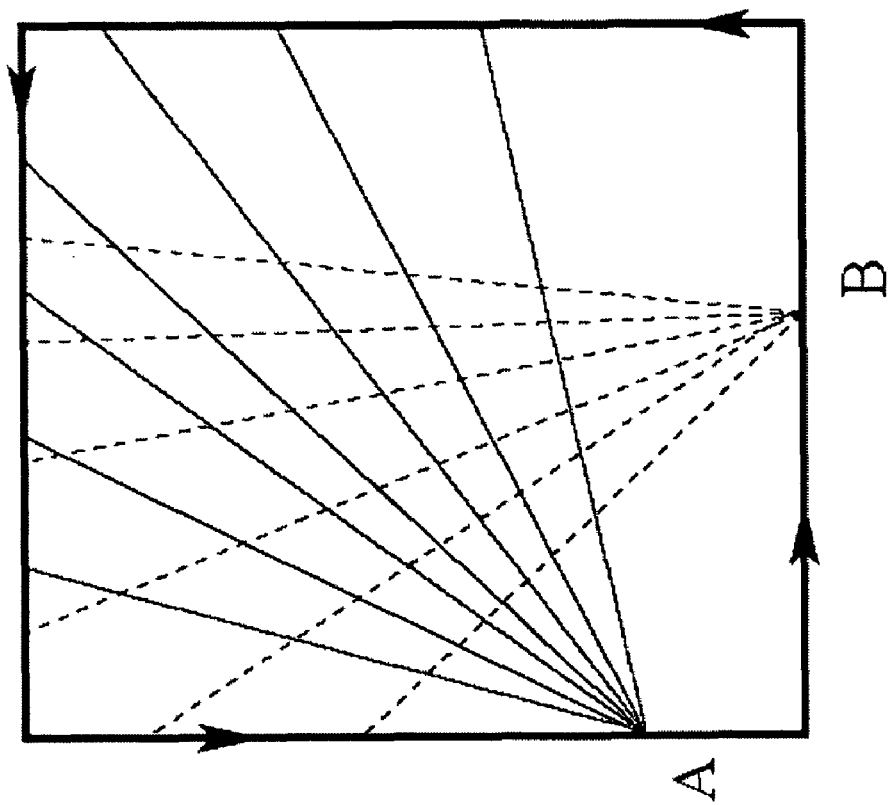
FIG. 22a illustrates two examples of fan-beam data generated by grouping the lines of response (LORs) associated with a given detection element (A or B) in a 2D rectangular PET system.

FIG. 22a illustrates an example of fan-beam data generated by grouping the LORs associated with a given detection element (A or B) in a 2D rectangular PET system. By advancing the detection element along the detector faces (indicated by arrows), an effective virtual source trajectory may be obtained. In this case, there is a unique non-trivial source trajectory. Thus, FIG. 22a illustrates how 2D PET data may be regrouped or organized into fan-beam data. The LORs associated with a given detection element form the fan-beam data with the detection element acting as the "source." A "source trajectory" or a virtual source trajectory can be obtained by advancing the source position on the detector faces. With the 2D rectangular system the only non-trivial trajectory consists of the four connected straight lines. When extending to 3D four-panel rectangular PET systems, the LORs associated with a given detection element may now form the cone-beam data. In this case, however, the source trajectory is no longer unique. In fact, any continuous path defined on the four detector panels is a valid path. FIG. 22b illustrates a virtual source trajectory obtained by projecting a helical path onto the detector panels. The pitch of the helical path may be varied for defining different trajectories. Different trajectories of this kind may also be generated by translating a trajectory along the scanner's axis. Trajectories as shown in FIG. 22b are different from the usual helical trajectories that are widely considered in x-ray cone-beam imaging: they contain connected linear segments with kinks. Regardless, the analytic cone-beam reconstruction techniques discussed above may be directly applied to work with such trajectories.

With the cone-beam reconstruction techniques, different paths result in different reconstruction algorithms and in general yield different regions that permit exact reconstruction (up to statistical uncertainties). For example, algorithms obtained with large-pitch helical trajectories may correspond to reconstructions obtained by including larger ring-difference coincidence data. Conversely, exact reconstruction for a given ROI may be obtained by employing different source trajectories, and hence from non-identical subsets of the acquired data. By appropriately defining multiple virtual source trajectories and averaging results generated by using these trajectories, all measured data may be considered in reconstruction for reducing noise. As shown below, reconstructions with the trajectory are illustrated in FIG. 22b. However, the reconstruction algorithm is applicable for general trajectories.

Chord-based reconstruction may be used for image reconstruction. For example, backprojection filtration (BPF) and the minimum-data filtered backprojection (MFBP) methodologies may be used for image reconstruction from cone-beam data acquired with a general trajectory. These methodologies may accommodate projection data collected with a trajectory with kinks. As FIGS. 22a and b above show, data acquired with a panel-based PET system may be interpreted as cone-beam data acquired with a virtual trajectory with singularities. Therefore, the methodologies for image reconstruction from cone-beam data may readily be applied to image reconstruction in the panel-based PET system.

As shown in FIG. 22b, an effective virtual trajectory $\vec{r}_0(\lambda)$ may be designed for a four-panel PET system. Such an effective virtual trajectory is a piecewise smooth function of λ with multiple singularities at the junctions of two neighboring panels. For the designed trajectory, a chord-line may be defined as a straight line intersecting with the effective virtual trajectory at two points $\vec{r}_0(\lambda_a)$ and $\vec{r}_0(\lambda_b)$. Alternatively, a chord may be defined as a curve intersecting with the effective virtual trajectory at two points $\vec{r}(\lambda_a)$ and $\vec{r}_0(\lambda_b)$. As discussed above, the segment on the chord-line with $\vec{r}_0(\lambda_a)$ and $\vec{r}_0(\lambda_b)$ as the ending points may be a type of chord. One can use:

$$\hat{e}_c = \frac{\vec{r}_0(\lambda_b) - \vec{r}(\lambda_a)}{|\vec{r}_0(\lambda_b) - \vec{r}(\lambda_a)|} \tag{56}$$

to denote the direction of the chord-line. Equation (56) is similar to equation (5). The cone-beam projection of an object function $f(\vec{r})$ may be expressed mathematically as:

$$P(u_d, v_d, \lambda) = \int_0^\infty dt f(\vec{r}_0(\lambda) + t\hat{\beta}) \tag{57}$$

where the unit vector $\hat{\beta}$ denotes the direction of a specific x-ray intersecting with the detector plane at $(u_d, v_d)$. The distance between the source and the projection point $(u_d, v_d)$ can be calculated by $A(u_d, v_d) = \sqrt{u_d^2 + v_d^2 + S^2}$ where S is the distance from the source to the detector.

Methodologies discussed above may reconstruct an image on a chord. Examples of the methodologies comprise BPF and MFBP. Similar to the discussion above for the BPF methodology, let $x_{c1}$ and $x_{c2}$ denote two ending points of a chord, and let $[x_A, X_B] \supset [x_{c1}, x_{c2}]$. Further, the modified data function may be defined as:

$$P'(u'_d, v'_d, \lambda) = -\left[\frac{d\vec{r}_0}{d\lambda} \cdot \hat{\beta}\right] P(u'_d, v'_d, \lambda) + \tag{58}$$

$$A(u'_d, v'_d)\frac{d\vec{r}_0}{d\lambda} \nabla_{u_d v_d} P(u'_d, v'_d, \lambda)$$

The BPF methodology may be given mathematically by:

$$f(\vec{r}) = \frac{f_{bp}(\vec{r}) + f_{bc}(\vec{r})}{2\pi^2 \sqrt{(x_B - x_c)(x_c - x_A)}} \quad \text{where} \tag{59}$$

$$f_{bp}(\vec{r}) = \tag{60}$$

$$\int_{x_A}^{x_B} \frac{dx'_c}{x_c - x'_c} \sqrt{(x_B - x'_c)(x'_c - x_A)} \times \int_{\lambda_1}^{\lambda_2} \frac{1}{|\vec{r}' - \vec{r}_0|^2} P'(u'_d, v'_d, \lambda),$$

$$f_{bc}(\vec{r}) = P(u_{d0}, v_{d0}, \lambda_1) \times \left[\frac{\pi\sqrt{2l - x_B)(2l - x_A)}}{2l - x_c} + \frac{\pi\sqrt{x_B x_A}}{x_c}\right] \tag{61}$$

with $l = |\vec{r}(\lambda_b) - \vec{r}(\lambda_a)|/2$, $$\vec{r}' = \vec{r}_0(\vec{r}) + x'_c \hat{e}_c, \, x'_c \in [0, 2l], \tag{62}$$

denoting the point on the chord identified by the coordinate $x'_c$, and $u_{do}$ and $v_{do}$ denote the location on the detector the cone-beam projection of the point $\vec{r}$ at the rotation angle $\lambda_1$. Equation (59) may be valid for any point $\vec{r}$ satisfying $x_c \in (x_A, x_B)$.

Moreover, Similar to the discussion above for the MFBP methodology, the methodology may be expressed as:

$$f(\vec{r}) = \int_{\lambda_1}^{\lambda_2} d\lambda [(1 - u_c)w_2 + u_c w_1] \times \tag{63}$$

$$\int_{x_A}^{x_B} \frac{du'_c}{u_c - u'_c} \frac{\sqrt{(x_B - x'_c)(x'_c - x_A)}}{(1 - u'_c)w_2 + u'_c w_1} \times$$

$$\frac{1}{|\vec{r}' - \vec{r}_0|^2} P'(u'_d, v'_d, \lambda) +$$

$$\frac{1}{2\pi^2} \frac{1}{\sqrt{(x_B - x_c)(x_c - x_A)}} f_{bc}(\vec{r}),$$

where $u_c$ denotes the cone-beam projection of $x_c$ onto the detector, and it can be related to $x_c$ by $$u_c = \frac{w_2 x_c}{w_1(1-x_c) + w_2 x_c},$$

with $w_1 = -[\vec{r}_0(\lambda_1) - \vec{r}_0(\lambda)] \cdot \hat{e}_w$ and $w_2 = -[\vec{r}_0(\lambda_2) - \vec{r}_0(\lambda)] \cdot \hat{e}_w$. The unit vector $\hat{e}_w$ indicates the direction from the source pointing to the middle point of the detector.

The following are numerical studies to demonstrate the ROI-image reconstruction in a four-panel PET system by use of the BPF and MFBP methodologies. Other types of PET systems and other types of methodologies may be used. For a PET system with four panels, as shown in FIG. 22*b*, one can devise a "square" virtual helical trajectory. This effective virtual trajectory may be parameterized as:

$$\vec{r}_0(\lambda) = \begin{cases} (R_0, 2R_0\lambda - R_0, h\lambda)^t & \lambda \in [0, 1], \\ (-2R_0\lambda + 3R_0, R_0, h\lambda)^t & \lambda \in [1, 2], \\ (-R_0, -2R_0\lambda + 5R_0, h\lambda)^t & \lambda \in [2, 3], \\ (2R_0\lambda - 7R_0, -R_0 h\lambda)^t & \lambda \in [3, 4], \end{cases} \quad (64)$$

where $R_0$ is the distance from a plane to the z-axis and h is similar to the pitch in a helical trajectory that determines the increase rate of the trajectory along the z-axis. With this trajectory, cone-beam projection data may be generated for Shepp-Logan phantom for 1024 views uniformly distributed in $\lambda \in [0, 4]$ by using $R_0 = 26.5$ cm and $h = 12.8$ cm.

Figure 23B:
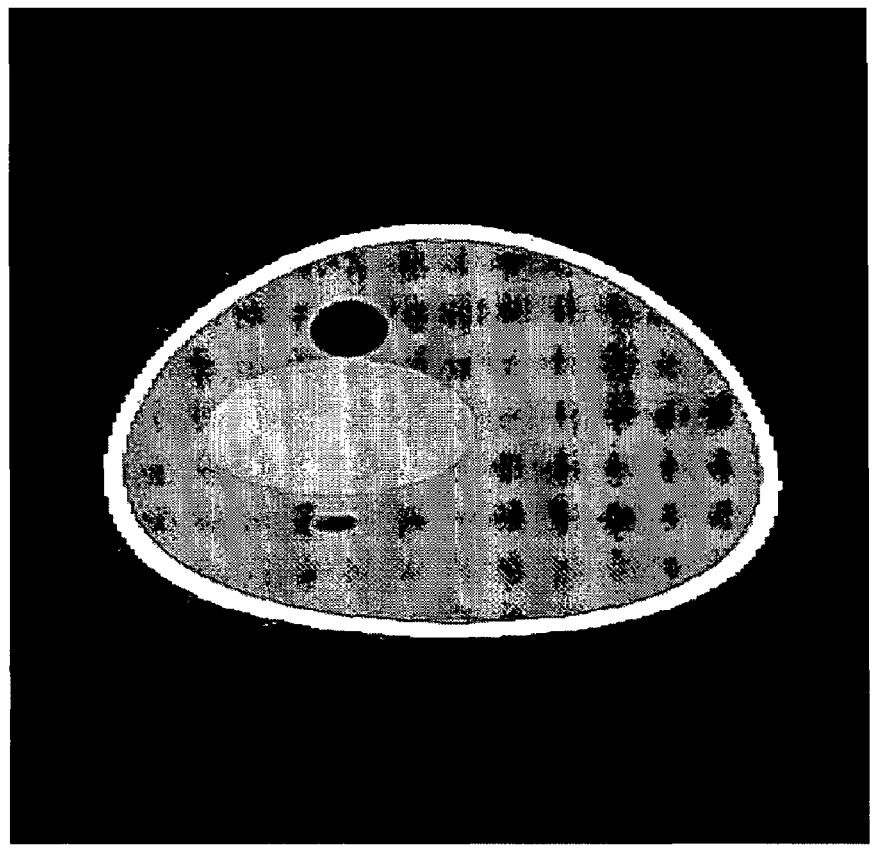
FIG. 23b illustrates a reconstructed image of the Shepp-Logan phantom on chords specified by $s_1=0.5$ and $s_2 \in (2, 3)$, with a display window of [1.0, 1.05].
Figure 23A:
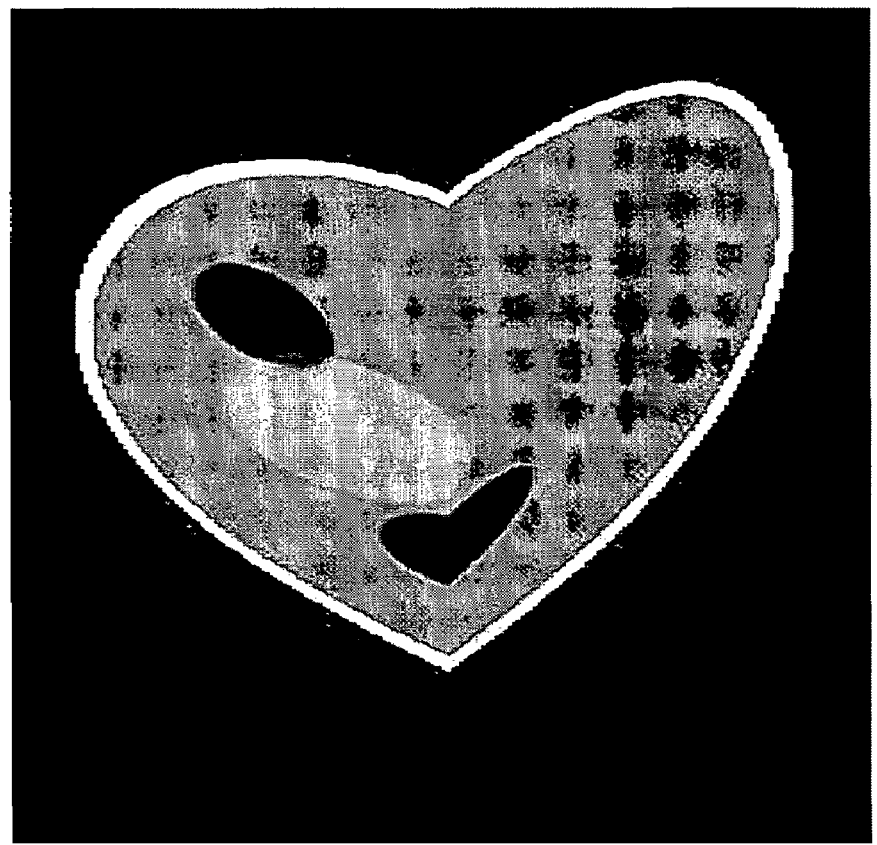
FIG. 23a illustrates a reconstructed image of the Shepp-Logan phantom on chords specified by $s_1=0$ and $s_2 \in (1, 3)$, with a display window of [1.0, 1.05].
Figures 24A, 24B, 24C:
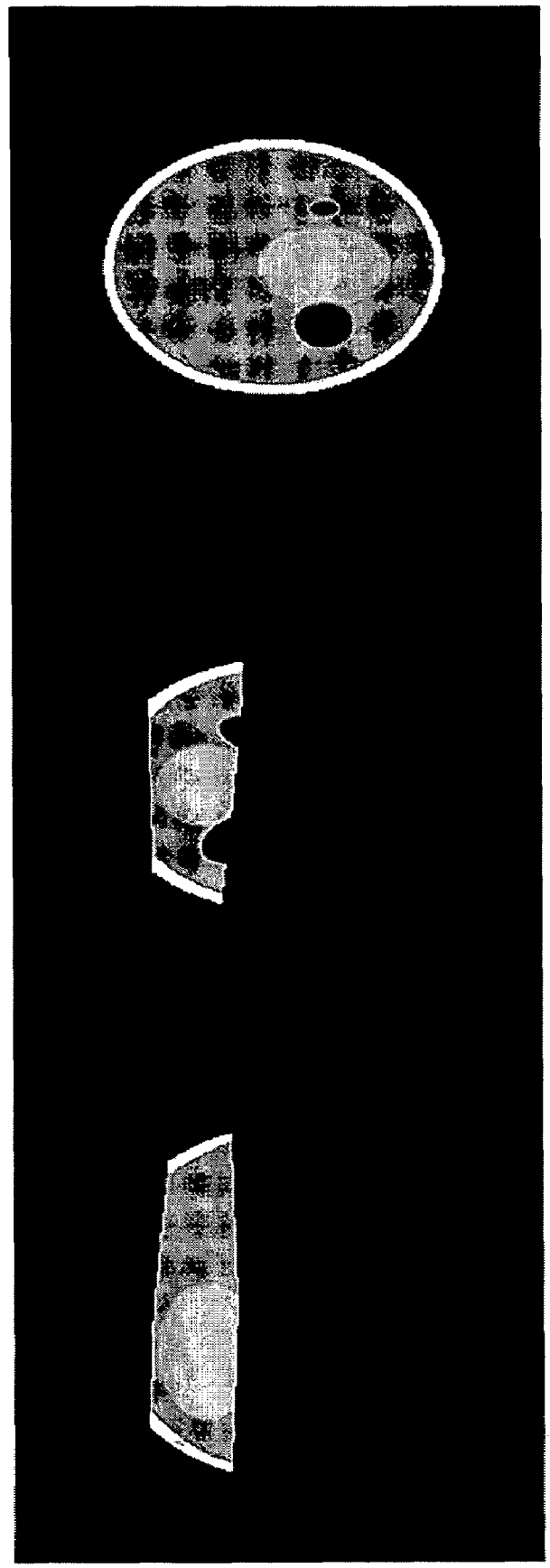
FIGS. 24a-c illustrate images in the planes at x=0 cm, y=−2.7 cm, and z=2.5 cm, respectively, with a display window of [1.0, 1.05].

From the simulated data, by use of the "square" virtual helical trajectory, images may be reconstructed using the BPF and MFBP methodologies. The following only displays results generated by the BPF methodology; however, the MFBP methodology may similarly be used. FIGS. 23*a* and *b* display images obtained on two selected sets of chords of the "square" virtual helical trajectory. In these images, the horizontal axis denotes the coordinate on each chord, $x'_c$ in Equation (62), whereas the vertical axis indicates different chords. When displaying results on these native chord coordinates, the images may appear substantially different from the original phantom defined on the Cartesian coordinates. In FIG. 23*a*, the image on the set of chords specified by $\lambda_1 = 0$ and $\lambda_2 \in (1, 3)$ is shown. The image appears to consist of two distinct parts. By inspecting the trajectory in FIG. 22*b*, it is observed that there is a kink at $\lambda = 2$, which forms the boundary of the two apparently distinct parts in the image. FIG. 23*b* also shows the image on the set of chords specified by $\lambda_1 = 0.5$ and $\lambda_2 \in (2, 3)$. Because the effective trajectory is smooth for $\lambda \in (2, 3)$, the image does not show distinct parts as observed in the previous case. Images obtained on the native chord coordinates may be readily transformed to obtain images on the Cartesian coordinates. FIGS. 24*a-c* shows the reconstructed images on the Cartesian coordinates. Specifically, FIGS. 24*a-c* represent the images in the planes at x=0 cm, y=−2.7 cm, and z=2.5 cm, respectively, with a display window of [1.0, 1.05].

Redundant Information

As discussed above, trajectories may be selected so that there are sufficient data generated to image the ROI. There are instances where data may be redundant in that the data are duplicative of other data already obtained. Data may be considered redundant if the source trajectory generates chords which are unnecessary to reconstruct the ROI (e.g., chords that do not fill the region of interest). Instead of simply discarding the redundant data, the redundant data may be used to modify, such as improve, a selected characteristic of the image. Any characteristic of the image may be modified using the redundant data including, but not limited to: noise, bias, texture, resolution, and variance.

The redundant information may first be identified, either qualitatively or quantitatively. For example, the redundant information may be identified qualitatively to determine whether the chords overfill the region of interest. Specifically, if a set of chords may be compiled which not only fill the ROI, but additional regions, redundant data may be present. Once it is determined that redundant data are present, the redundant data may be factored into modifying the at least one characteristic. For example, weights may be used to factor in the redundant data, as discussed in more detail below. Alternatively, the redundant data may be discarded if one wishes to accelerate the processing of the image.

Figure 25B:
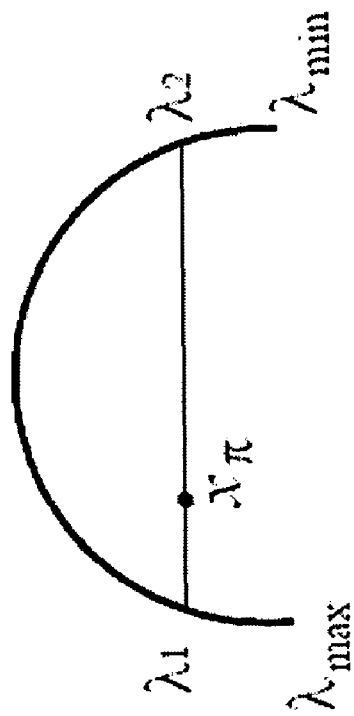
FIG. 25b illustrates an actual scanning angular range of $\lambda_{min}$ to $\lambda_{max}$ indicating redundant information.
Figure 25A:
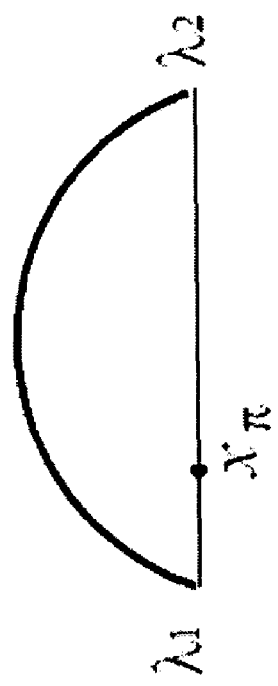
FIG. 25a illustrates a scanning angular range of $\lambda_1$ to $\lambda_2$ necessary for exact reconstruction of an image.

The following is an example using the scan from FIGS. 7*a-c*. Though a 2-dimensional ROI is used in the example, redundant information may likewise be used when imaging a 3-dimensional ROI. If the ROI may be contained within the region bounded by the PI-line segment specified by $\lambda_1$ and $\lambda_2$ and the fan beam scan, the necessary scanning angular range is $[\lambda_1, \lambda_2]$, as shown in FIG. 25*a*. Considering an actual scanning angular range $[\lambda_{min}, \lambda_{max}]$, as shown in FIG. 25*b*, if $[\lambda_1, \lambda_2] \in [\lambda_{min}, \lambda_{max}]$, data acquired over the angular ranges $[\lambda_{min}, \lambda_1)$ and $(\lambda_2, \lambda_{max}]$ contain redundant information with respect to the image reconstruction on the PI-line segment specified by $\lambda_1$ and $\lambda_2$.

The chord reconstruction methodology may reconstruct the image on this PI-line segment by use of data only over $[\lambda_1, \lambda_2]$. Data over $[\lambda_{min}, \lambda_{max})$ and $(\lambda_2, \lambda_{max}]$ need not be utilized.

Such redundant information may readily be incorporated into the reconstruction methodology. To factor in the redundant information, data acquired over the actual scanning angular range $[\lambda_{min}, \lambda_{max}]$ may be appropriately weighted so that the contribution to the image on the PI-line segment from the redundant portions of the acquired data may be adequately normalized.

The backprojection that exploits the redundant information inherent in data may be given by:

$$g_\pi^{(w)}(x'_\pi, \lambda_1, \lambda_2) = \qquad (65)$$

$$\int_{\lambda_{min}}^{\lambda_{max}} \frac{d\lambda}{|\vec{r}' - \vec{r}_0(\lambda)|^2} \left\{ -\left[\frac{d\vec{r}_0(\lambda)}{d\lambda} \cdot \hat{\beta}(u'_d, \lambda)\right] [w(u'_d, \lambda) P(u'_d, \lambda)] + \right.$$

$$\left. \left[\frac{d\vec{r}_0(\lambda)}{d\lambda}\right] \cdot \hat{e}_u(\lambda) \sqrt{u_d'^2 + S^2} \, \frac{\partial [w(u'_d, \lambda) P(u_d^{1,\lambda})]}{\partial u'_d} \right\} +$$

$$\left. \frac{[w(u'_d, \lambda) P(u'_d, \lambda)]}{|\vec{r}' - \vec{r}_0(\lambda)|} \right|_{\lambda_{min}}^{\lambda_{max}}$$

where the weighting function $w(u_d, \lambda)$ is given by:

$$\omega(u_d, \lambda) - \omega(u'_d, \lambda') = 1.0 \qquad (66)$$

$$\omega(u_d, \lambda) = 0 \text{ if } \lambda < \lambda_{min} \text{ or } \lambda < \lambda_{max} \qquad (67)$$

Therefore, Equation (65) comprises a new methodology capable of exploiting the data redundancy. As shown in Equation (65), the integration is from $\lambda_{min}$ to $\lambda_{max}$. Further, the choice of $\omega$ depends on the characteristic sought to be modified. For example, if variance is sought to be improved, one may take the derivative of Equation (65) with respect to ω, set it to zero, and solve for ω. As another example, if bias may be represented as a function of ω, the bias may be improved by taking the derivative of the bias function with respect to ω, set it to zero and solve for ω.

As discussed above, there are numerous ways in which to reconstruct the image based on the collected data. One method and apparatus of imaging an ROI in an object support, with the ROI being a portion of the object support, comprises collecting data which is less than that sufficient to substantially exactly reconstruct an image for the object support, and generating a substantially exact reconstruction of the ROI based on the collected data. The object support, as discussed above, may comprise a domain in space within which the object may be non-zero and outside of which is certainly zero. For example, the data collected may comprise truncated data for the object support. Further, to collect the data, a source may be moved in a trajectory relative to the object support so that data less than that sufficient to substantially reconstruct an image for the object support is collected. The trajectory may be one in which a set of segments of chords defined by the trajectory fill the ROI. Moreover, to collect the data, a source may be controlled so that the data, which is less than that sufficient to substantially reconstruct an image for the object support, is collected. For example, controlling the source may comprise moving the source relative to the object support, and modifying at least one characteristic of the source as the source moves relative to the object support. The modifying of the source may be based on the ROI, such as reducing illumination of the object support outside of the ROI. Moreover, modifying of the source may change the illumination coverage of the source so that the ROI is substantially illuminated and outside of the ROI illumination is reduced, such as not substantially illuminated. Generating a substantially exact reconstruction of the ROI may comprise filtering the collected data, and backprojecting the filtered data to generate a density distribution. Backprojecting may comprise backprojecting onto at least a portion of a chord defined by a path of a source used for collecting data on the ROI. Alternatively, generating a substantially exact reconstruction of the ROI may comprise backprojecting based on the collected data to generate an intermediate density distribution, and filtering the intermediate density distribution to create a substantially exact image of the ROI, such as a volume filling image.

Another method and apparatus for imaging a region of an object may comprise irradiating the region with a radiation source traveling along a source path relative to the object, collecting data on radiation transmitted through the region of interest, and constructing an image of the region from the collected data based at least in part on a coordinate system defined by the source path. Constructing the image of the region from the collected data may comprise identifying a set of chords that connect pairs of points along the source path, wherein the set of chords fill a volume for a region of interest in the object, calculating image densities on the chords from the collected data, and constructing a three-dimensional image based on the image densities and on the source path. The coordinate system may be defined by a first point relating to the source path, a second point relating to the source path which is different from the first point, and a third point on a chord formed between the first point and the second point. An additional step may include transforming the constructed image into Cartesian coordinates. Or, the constructed image may already be in Cartesian coordinates.

Another method and apparatus for imaging a region of an object may comprise irradiating the region with a radiation source traveling along a source path relative to the object, collecting data on radiation transmitted through the object, and constructing an image on a plurality of chords defined by the source path. The chords may comprise PI-lines. And the construction of the image may include identifying a set of chords that connect pairs of points along the source path, where the set of chords fill a volume for a region of interest in the object, calculating image densities on the chords from the collected data, and constructing a three-dimensional image based on the image densities and on the source path.

Still another method and apparatus for imaging a region of an object comprises collecting data on radiation emitted from the object and organizing the data according to detection locations that form a path, where the path defines chords with segments that fill a volume of the region of the object. Any type of radiation may be emitted such as positron emission. Moreover, a method and apparatus for imaging an ROI using positron emission tomography may include collecting data emitted from the object and organizing the data in order to reconstruct the ROI based on chords. The organizing of the data may be based on selecting a virtual source external to the object traveling along a virtual source trajectory. Further, reconstructing the ROI may include identifying a set of chords that connect pairs of points along the virtual source trajectory, wherein the set of chords fill a volume for the ROI, calculating image densities on the chords from collected data; and constructing a three-dimensional image based on the image densities.

Still another method and apparatus for imaging a region of interest for an object may include collecting data on the region of interest, backprojecting based on the data to generate an intermediate object function, and filtering the intermediate object function to create a substantially exact image of the region of interest. The backprojecting may include backprojecting onto at least a portion of a chord defined by a path of a source used for collecting data on the region of interest. And, the filtering may comprise using a Hilbert transform. Further, backprojecting may be based on modified data (such as weighted data) to generate the intermediate object function or may be based on unmodified data.

Another method and apparatus for imaging a region of interest in an object may include collecting truncated data on the region of interest and generating a substantially exact reconstruction of an image based on the truncated data. There are various methods for generating the substantially exact reconstruction, such as filtering the truncated data and backprojecting the filtered truncated data to generate a density distribution, or such as backprojecting the data to generate an intermediate object function and filtering the intermediate object function to create a substantially exact image of the region of interest. Further, the backprojection may include backprojecting onto at least a portion of a chord defined by a path of a source used for collecting data on the region of interest.

It is intended that the foregoing detailed description be regarded as illustrative, rather than limiting, and that it be understood that the following claims, including all equivalents, are intended to define the scope of this invention.

The invention claimed is:

1. A method of imaging at least a part of a region of interest (ROI) comprising:
   decomposing the at least a part of the ROI into chords; and
   reconstructing the at least a part of the ROI based on the chords using data,
   wherein an object support comprises a domain in space within which the object may be non-zero and outside of which is certainly zero;

wherein the ROI is a portion of and smaller than the object support;

wherein a trajectory of a source relative to the object defines a coordinate system; and wherein the source illuminates the ROI during at least a part of the trajectory resulting in the data being acquired, the data comprising projections containing truncations along at least two axes of said coordinate system.

2. The method of claim 1, wherein the trajectory comprises a helical trajectory.

3. A computer-readable medium containing program code for:

imaging at least part of a region of interest (ROI);

decomposing the at least a part of the ROI into chords; and reconstructing the at least a part of the ROI based on the chords using data, wherein an object support comprises a domain in space within which the object may be non-zero and outside of which is certainly zero;

wherein the ROI is a portion of and smaller than the object support;

wherein a trajectory of a source relative to the object defines a coordinate system; and wherein the source illuminates the ROI during at least a part of the trajectory resulting in the data being acquired, the data comprising projections containing truncations along at least two axes of said coordinate system.

4. The computer-readable medium of claim 3, wherein the trajectory comprises a helical trajectory.

5. A method of imaging at least a part of a region of interest (ROI), the ROI being a portion of and smaller than an object support comprising a domain in space within which the object may be non-zero and outside of which is certainly zero, the method comprising:

controlling at least one of a source and the object support so that the source and the object support move relative to one another in a trajectory that defines a rotation axis;

acquiring data at least partly when the source and the object support move relative to one another; and generating a substantially exact reconstruction of the ROI based on the data, the data being less than that required to substantially exactly reconstruct an image of the entire object support, wherein the data comprises projections, such projections containing truncations parallel and perpendicular to the rotation axis.

6. The method of claim 5, wherein the data that is used to generate a substantially exact reconstruction excludes data in at least a part of object support that is outside of the ROI.

7. The method of claim 6, wherein the data that is used to generate a substantially exact reconstruction completely excludes the data in the part of the object support that is outside of the ROI.

8. The method of claim 5, wherein the data is acquired using an imaging system; and wherein acquiring the data for imaging the ROI comprises selecting at least one parameter for the imaging system so that the data acquired by the imaging system is less than that required to substantially exactly reconstruct an image of the entire object support.

9. The method of claim 8, wherein the at least one parameter comprises a parameter of the trajectory of the source relative to the object support.

10. The method of claim 8, wherein the at least one parameter comprises an illumination parameter for the source.

11. The method of claim 10, wherein the source generates a beam with a beam size; and wherein the illumination parameter comprises the beam size.

12. The method of claim 11, further comprising modifying the beam size of the source in order to acquire the data that is less than that required to substantially exactly reconstruct an image of the entire object support.

13. The method of claim 12, wherein the trajectory of the source relative to the object support comprises a helical trajectory.

14. The method of claim 5, wherein generating a substantially exact reconstruction of the ROI comprises:

decomposing the ROI into chords; and substantially exactly reconstructing the ROI based on the chords.

15. The method of claim 14, wherein the chords comprise PI-lines.

16. The method of claim 14, wherein the chords are defined by the trajectory of a source relative to the object support.

17. The method of claim 16, wherein generating a substantially exact reconstruction of the ROI comprises:

identifying a set of chords that connect pairs of points along the trajectory, wherein the set of chords fill a volume for the ROI;

calculating image densities on the chords from the acquired data; and constructing a three-dimensional image based on the image densities.

18. The method of claim 5, wherein generating a substantially exact reconstruction of the ROI comprises:

backprojecting based on the acquired data to generate an intermediate density distribution; and filtering the intermediate density distribution to create a substantially exact image of the ROI.

19. The method of claim 5, wherein generating a substantially exact reconstruction of the ROI comprises:

filtering the acquired data; and backprojecting the filtered data to generate a density distribution.

20. The method of claim 5, wherein generating a substantially exact reconstruction of the ROI comprises rebinning the data.

21. The method of claim 5, wherein the ROI is 2-dimensional.

22. The method of claim 5, wherein the ROI is 3-dimensional.

23. The method of claim 5, wherein the imaging comprises computed tomography.

24. The method of claim 5, wherein the trajectory comprises a helical trajectory or a circular trajectory.

25. The method of claim 24, wherein the source comprises a beam angle; and wherein the trajectory, during which the source illuminates the ROI, covers an angular range less than a range of $\pi$+the beam angle.

26. The method of claim 25, wherein the ROI comprises at least a portion of a breast.

27. The method of claim 25, wherein the ROI comprises at least a portion of an internal organ.

28. An apparatus for imaging at least a part of a region of interest (ROI), the ROI being a portion of and smaller than an object support comprising a domain in space within which the object may be non-zero and outside of which is certainly zero, the apparatus comprising:

a source for illuminating the ROI;

at least one motor to control at least one of the source or the object support in order to move the source relative to the object support in a trajectory that defines a rotation axis;

at least one sensor to acquire data at least partly when the source and the object support move relative to one another; and a processor to generate a substantially exact reconstruction of the ROI based on the data, the data being less than that required to substantially exactly reconstruct an image of the entire object support, wherein the data comprises projections, such projections containing truncations parallel and perpendicular to the rotation axis.

29. The apparatus of claim 28, wherein the data that is used to generate a substantially exact reconstruction excludes data in at least a part of object support that is outside of the ROI.

30. The apparatus of claim 29, wherein the data that is used to generate a substantially exact reconstruction completely excludes the data in the part of object support that is outside of the ROI.

31. The apparatus of claim 28,
wherein the processor selects at least one parameter for the apparatus so that the data acquired by the at least one sensor is less than that required to substantially exactly reconstruct an entire image of the object support.

32. The apparatus of claim 31,
wherein the at least one parameter comprises a parameter of the trajectory of the source relative to the object support.

33. The apparatus of claim 31,
wherein the at least one parameter comprises an illumination parameter for the source.

34. The apparatus of claim 33, wherein the source generates a beam with a beam size; and
wherein the illumination parameter comprises the beam size.

35. The apparatus of claim 34, wherein the processor modifies the beam size of the source in order to acquire the data that is less than that required to substantially exactly reconstruct an image of the entire object support.

36. The apparatus of claim 35, wherein the trajectory of the source relative to the object support comprises a helical trajectory.

37. The apparatus of claim 28, wherein generating a substantially exact reconstruction of the ROI comprises:
decomposing the ROI into chords; and
substantially exactly reconstructing the ROI based on the chords.

38. The apparatus of claim 37, wherein the chords comprise PI-lines.

39. The apparatus of claim 37, wherein the chords are defined by a trajectory of a source relative to the object support.

40. The apparatus of claim 39, wherein generating a substantially exact reconstruction of the ROI comprises:
identifying a set of chords that connect pairs of points along the trajectory, wherein the set of chords fill a volume for the ROI;
calculating image densities on the chords from the acquired data; and
constructing a three-dimensional image based on the image densities.

41. The apparatus of claim 28, wherein generating a substantially exact reconstruction of the ROI comprises:
backprojecting based on the acquired data to generate an intermediate density distribution; and
filtering the intermediate density distribution to create a substantially exact image of the ROI.

42. The apparatus of claim 28, wherein generating a substantially exact reconstruction of the ROI comprises:
filtering the acquired data; and
backprojecting the filtered data to generate a density distribution.

43. The apparatus of claim 28, wherein generating a substantially exact reconstruction of the ROI comprises rebinning the data.

44. The apparatus of claim 28, wherein the ROI is 2-dimensional.

45. The apparatus of claim 28, wherein the ROI is 3-dimensional.

46. The apparatus of claim 28, wherein the imaging comprises computed tomography.

47. The apparatus of claim 28, wherein the trajectory comprises a helical trajectory or a circular trajectory.

48. The apparatus of claim 47, wherein the source comprises a beam angle; and
wherein the trajectory, during which the source illuminates the ROI, covers an angular range less than a range of π+the beam angle.

49. The apparatus of claim 48, wherein the ROI comprises at least a portion of a breast.

50. The apparatus of claim 48, wherein the ROI comprises at least a portion of an internal organ.

* * * * *